(12) United States Patent
Brookings et al.

(10) Patent No.: US 9,227,984 B2
(45) Date of Patent: Jan. 5, 2016

(54) THERAPEUTICALLY ACTIVE FUSED PYRIMIDINE DERIVATIVES

(75) Inventors: Daniel Christopher Brookings, Slough (GB); Daniel James Ford, Slough (GB); Anant Ramrao Ghawalkar, Hyderabad (IN); Jean Herman, Heverlee (BE); Qiuya Huang, Leuven (BE); Claire Louise Kulisa, Slough (GB); Thierry Louat, Heverlee (BE); Judi Charlotte Neuss, Slough (GB); James Thomas Reuberson, Slough (GB); Bart Vanderhoydonck, Diest (BE)

(73) Assignees: UCB Pharma S.A., Brussels (BE); Katholieke Universiteit Leuven, K.U.Leuven R&D, Leuven (BE)

(*) Notice: Subject to any disclaimer, the term of this patent is extended or adjusted under 35 U.S.C. 154(b) by 26 days.

(21) Appl. No.: 14/239,406

(22) PCT Filed: Aug. 15, 2012

(86) PCT No.: PCT/GB2012/051992
§ 371 (c)(1),
(2), (4) Date: Jul. 1, 2014

(87) PCT Pub. No.: WO2013/024291
PCT Pub. Date: Feb. 21, 2013

(65) Prior Publication Data
US 2014/0309222 A1    Oct. 16, 2014

(30) Foreign Application Priority Data
Aug. 18, 2011   (GB) .................................. 1114212.2

(51) Int. Cl.
*A01N 43/90*    (2006.01)
*A61K 31/519*   (2006.01)
*C07D 471/00*   (2006.01)
*C07D 487/00*   (2006.01)
*C07D 491/00*   (2006.01)
*C07D 495/04*   (2006.01)
*C07D 513/04*   (2006.01)
*C07D 519/00*   (2006.01)

(52) U.S. Cl.
CPC ............ *C07D 495/04* (2013.01); *A61K 31/519* (2013.01); *C07D 513/04* (2013.01); *C07D 519/00* (2013.01)

(58) Field of Classification Search
None
See application file for complete search history.

(56) References Cited

FOREIGN PATENT DOCUMENTS

| DE | 22 00 764 A1 | 7/1973 |
|---|---|---|
| WO | 01/46200 A1 | 6/2001 |
| WO | 03/022214 A2 | 3/2003 |
| WO | 2006/079916 A1 | 8/2006 |
| WO | 2006/100591 A1 | 9/2006 |
| WO | 2006/103544 A2 | 10/2006 |
| WO | 2006/103545 A1 | 10/2006 |
| WO | 2006/103555 A1 | 10/2006 |
| WO | 2007/146284 A2 | 12/2007 |
| WO | 2010/103130 A2 | 9/2010 |
| WO | 2011/029054 A1 | 3/2011 |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Darias, et. al., Chimica Therapeutica (1972), 7(3), 224-7.*
Kortum et al., "Thienopyrimidine-based P2Y12 platelet aggregation inhibitors", Bioorganic & Medicinal Chemistry Letters, 2009, 19(20), 5919-5923.
XP002685933, Database Registry Chemical Abstracts, 2004, 1 page.
XP002685934, Database Registry Chemical Abstracts, 2011, 1 page.
XP002685935, Database Registry Chemical Abstracts, 2011, 1 page.
XP002685936, Database Registry Chemical Abstracts, 2011, 1 page.
XP002685937, Database Registry Chemical Abstracts, 2011, 1 page.
XP002685938, Database Registry Chemical Abstracts, 2011, 1 page.
XP002685939, Database Registry Chemical Abstracts, 2011, 1 page.
XP002685940, Database Registry Chemical Abstracts, 2011, 1 page.
XP002685941, Database Registry Chemical Abstracts, 2011, 1 page.
XP002685942, Database Registry Chemical Abstracts, 2011, 1 page.
XP002685943, Database Registry Chemical Abstracts, 2011, 1 page.
XP002685944, Database Registry Chemical Abstracts, 2011, 1 page.
R. Böhm et al., Pharmazie, 1986, 41, 23-25 (Compounds in the figure at the bottom of the left column on p. 23, the compounds of Tables 1 and 2 on p. 24, and the figure at the top of p. 25).

* cited by examiner

*Primary Examiner* — Jeffrey H Murray
(74) *Attorney, Agent, or Firm* — McDonnell Boehnen Hulbert & Berghoff LLP

(57) ABSTRACT

A series of monocyclic or bicyclic diamine-substituted thieno [2,3-d]pyrimidine and isothiazolo[5,4-d]pyrimidine derivatives are beneficial in the treatment and/or prevention of various human ailments, including inflammatory, autoimmune and oncological disorders; viral diseases; and organ and cell transplant rejection.

11 Claims, No Drawings

THERAPEUTICALLY ACTIVE FUSED PYRIMIDINE DERIVATIVES

This application is a US national phase of International Application No. PCT/GB2012/051992 filed on Aug. 15, 2012, which claims priority to Great Britain Patent Application No. 1114212.2 filed on Aug. 18, 2011, the disclosures of which are incorporated herein by reference in their entirety.

The present invention relates to a class of fused pyrimidine derivatives, and to their use in therapy. More particularly, the present invention provides monocyclic or bicyclic diamine-substituted thieno[2,3-d]pyrimidine and isothiazolo[5,4-d] pyrimidine derivatives. These compounds are of benefit as pharmaceutical agents, especially in the treatment of adverse inflammatory, autoimmune and oncological disorders, in the treatment of viral diseases, and in the management of organ and cell transplant rejection.

In addition, the compounds in accordance with the present invention may be beneficial as pharmacological standards for use in the development of new biological tests and in the search for new pharmacological agents. Thus, the compounds of this invention may be useful as radioligands in assays for detecting pharmacologically active compounds.

WO 2010/103130 describes a family of oxazolo[5,4-d] pyrimidine, thiazolo[5,4-d]-pyrimidine, thieno[2,3-d]pyrimidine and purine derivatives that are active in a range of assays, including the Mixed Lymphocyte Reaction (MLR) test, and are stated to be effective for the treatment of immune and auto-immune disorders, and organ and cell transplant rejection. Copending international patent application PCT/EP2011/058276, published on 1 Dec. 2011 as WO 2011/147753, discloses the same family of compounds as having significant antiviral activity. Furthermore, copending international patent application PCT/IB2011/002248, published on 22 Mar. 2012 as WO 2012/035423 (claiming priority from GB patent application 1015411.0), discloses the same family of compounds as having significant anticancer activity.

None of the prior art available to date, however, discloses or suggests the precise structural class of fused pyrimidine derivatives as provided by the present invention.

The compounds in accordance with the present invention are active as inhibitors when subjected to the Mixed Lymphocyte Reaction (MLR) test. The MLR test is predictive of immunosuppression or immunomodulation. Thus, when subjected to the MLR test, the compounds of the present invention display an $IC_{50}$ value of 10 μM or less, generally of 5 μM or less, usually of 2 μM or less, typically of 1 μM or less, suitably of 500 nM or less, ideally of 100 nM or less, and preferably of 20 nM or less (the skilled person will appreciate that a lower $IC_{50}$ figure denotes a more active compound).

The present invention provides a compound of formula (I) or an N-oxide thereof, or a pharmaceutically acceptable salt or solvate thereof:

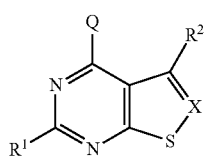

(I)

wherein
Q represents a group of formula (Qa) or (Qb):

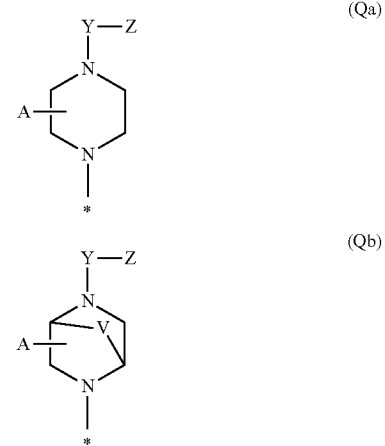

in which the asterisk (*) represents the point of attachment to the remainder of the molecule;

V represents —$CH_2$—, —$CH_2CH_2$— or —$CH_2CH_2CH_2$—;

X represents C—$R^3$ or N;

Y represents a covalent bond, or a linker group selected from —C(O)—, —S(O)—, —S(O)$_2$—, —C(O)O—, —C(O)N($R^4$)— and —S(O)$_2$N($R^4$)—;

Z represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents;

A represents hydrogen or trifluoromethyl; or $C_{1-6}$ alkyl, optionally substituted by one or more substituents independently selected from —$OR^a$ and —$NR^bR^c$;

$R^1$ and $R^2$ independently represent hydrogen, halogen, cyano, nitro, hydroxy, trifluoromethyl, trifluoromethoxy, —$OR^a$, —$SR^a$, —$SOR^a$, —$SO_2R^a$, —$NR^bR^c$, —$CH_2NR^bR^c$, —$NR^cCOR^d$, —$CH_2NR^cCOR^d$, —$NR^cCO_2R^d$, —$NHCONR^bR^c$, —$NR^cSO_2R^e$, —$N(SO_2R^e)_2$, —$NHSO_2NR^bR^c$, —$COR^d$, —$CO_2R^d$, —$CONR^bR^c$, —$CON(OR^a)R^b$ or —$SO_2NR^bR^c$; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents;

$R^3$ and $R^4$ independently represent hydrogen; or $C_{1-6}$ alkyl, optionally substituted by one or more substituents independently selected from —$OR^a$ and —$NR^bR^c$;

$R^a$ represents hydrogen; or $R^a$ represents $C_{1-6}$ alkyl, aryl, aryl($C_{1-6}$)alkyl, heteroaryl or heteroaryl($C_{1-6}$)alkyl, any of which groups may be optionally substituted by one or more substituents;

$R^b$ and $R^c$ independently represent hydrogen or trifluoromethyl; or $C_{1-6}$ alkyl, $C_{3-7}$ cycloalkyl, $C_{3-7}$ cycloalkyl($C_{1-6}$) alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents; or $R^b$ and $R^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;

$R^d$ represents hydrogen; or $C_{1-6}$ alkyl, $C_{3-7}$ cycloalkyl, aryl, $C_{3-7}$ heterocycloalkyl or heteroaryl, any of which groups may be optionally substituted by one or more substituents; and $R^e$ represents $C_{1-6}$ alkyl, aryl or heteroaryl, any of which groups may be optionally substituted by one or more substituents.

The present invention also provides a compound of formula (I) as depicted above, or an N-oxide thereof, or a pharmaceutically acceptable salt or solvate thereof, wherein Q represents a group of formula (Qa);

$R^1$ and $R^2$ independently represent hydrogen, halogen, cyano, nitro, hydroxy, trifluoromethyl, trifluoromethoxy, $-OR^a$, $-SR^a$, $-SOR^a$, $-SO_2R^a$, $-NR^bR^c$, $-CH_2NR^bR^c$, $-NR^cCOR^d$, $-CH_2NR^cCOR^d$, $-NR^cCO_2R^d$, $-NHCONR^bR^c$, $-NR^cSO_2R^e$, $-N(SO_2R^e)_2$, $-NHSO_2NR^bR^c$, $-COR^d$, $-CO_2R^d$, $-CONR^bR^c$, $-CON(OR^a)R^b$ or $-SO_2NR^bR^c$; or $C_{1-6}$ alkyl, aryl, aryl($C_{1-6}$)alkyl, heteroaryl or heteroaryl($C_{1-6}$)alkyl, any of which groups may be optionally substituted by one or more substituents;

$R^a$ represents $C_{1-6}$ alkyl, aryl, aryl($C_{1-6}$)alkyl, heteroaryl or heteroaryl($C_{1-6}$)alkyl, any of which groups may be optionally substituted by one or more substituents; and X, Y, Z, A, $R^3$, $R^4$, $R^b$, $R^c$, $R^d$ and $R^e$ are as defined above.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched $C_{1-6}$ alkyl groups, for example $C_{1-4}$ alkyl groups. Typical examples include methyl and ethyl groups, and straight-chained or branched propyl, butyl, pentyl and hexyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Specific $C_{3-7}$ cycloalkyl groups, which may comprise benzo-fused analogues thereof, include cyclopropyl, cyclobutyl, cyclopentyl, cyclohexyl, 1,2,3,4-tetrahydronaphthyl and cycloheptyl.

Suitable aryl groups include phenyl and naphthyl, preferably phenyl.

Suitable aryl($C_{1-6}$)alkyl groups include benzyl, phenylethyl, phenylpropyl, phenylbutyl and naphthylmethyl.

Suitable heterocycloalkyl groups, which may comprise benzo-fused analogues thereof, include azetidinyl, tetrahydrofuranyl, dihydrobenzofuranyl, pyrrolidinyl, indolinyl, thiazolidinyl, imidazolidinyl, tetrahydropyranyl, chromanyl, piperidinyl, 1,2,3,4-tetrahydroquinolinyl, 1,2,3,4-tetrahydroisoquinolinyl, piperazinyl, 1,2,3,4-tetrahydro-quinoxalinyl, homopiperazinyl, morpholinyl, benzoxazinyl and thiomorpholinyl.

Suitable heteroaryl groups include furyl, benzofuryl, dibenzofuryl, thienyl, benzothienyl, dibenzothienyl, pyrrolyl, indolyl, pyrrolo[2,3-b]pyridinyl, pyrrolo[3,2-c]pyridinyl, pyrazolyl, pyrazolo[1,5-c]pyridinyl, pyrazolo[3,4-d]pyrimidinyl, indazolyl, oxazolyl, benzoxazolyl, isoxazolyl, thiazolyl, benzothiazolyl, isothiazolyl, imidazolyl, benzimidazolyl, imidazo[1,2-c]pyridinyl, imidazo[4,5-b]pyridinyl, purinyl, imidazo[1,2-c]pyrimidinyl, imidazo[1,2-c]pyrazinyl, oxadiazolyl, thiadiazolyl, triazolyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$) ↔ enol (CH=CHOH) tautomers or amide (NHC=O) ↔ hydroxyimine (N=COH) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$.

Similarly, by way of example, each individual carbon atom present in formula (I), or in the formulae depicted hereinafter, may be present as a $^{12}C$, $^{13}C$ or $^{14}C$ atom, preferably $^{12}C$.

In a particular embodiment, Q represents a group of formula (Qa) as defined above. In another embodiment, Q represents a group of formula (Qb) as defined above.

In one embodiment, X represents C—$R^3$. In another embodiment, X represents N.

Particular sub-classes of compounds in accordance with the present invention are represented by the compounds of formula (IA), (IB), (IC) and (ID):

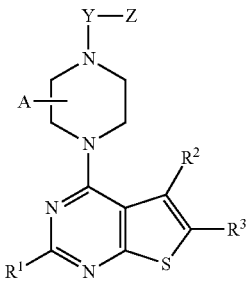
(IA)

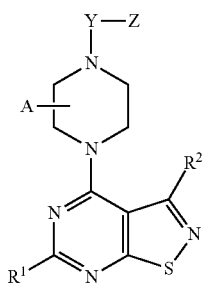
(IB)

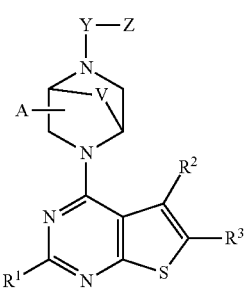
(IC)

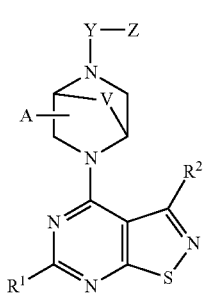
(ID)

wherein V, Y, Z, A, $R^1$, $R^2$ and $R^3$ are as defined above.

Specific sub-classes of compounds in accordance with the present invention are represented by the compounds of formula (IA) and (IB) as defined above.

Where Q represents a group of formula (Qa) as defined above, this may be a group of formula (Qa-1) or (Qa-2):

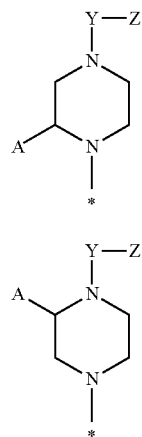

(Qa-1)

(Qa-2)

in which the asterisk (*) represents the point of attachment to the remainder of the molecule; and Y, Z and A are as defined above.

In a first embodiment, Q represents a group of formula (Qa-1) as defined above.

In a second embodiment, Q represents a group of formula (Qa-2) as defined above.

In a particular embodiment, V represents —CH$_2$—. Where V represents —CH$_2$—, the bicyclic moiety containing the integer V is a 2,5-diazabicyclo[2.2.1]heptane ring system.

In another embodiment, V represents —CH$_2$CH$_2$—. Where V represents —CH$_2$CH$_2$—, the bicyclic moiety containing the integer V is a 2,5-diazabicyclo[2.2.2]octane ring system.

In a further embodiment, V represents —CH$_2$CH$_2$CH$_2$—. Where V represents —CH$_2$CH$_2$CH$_2$—, the bicyclic moiety containing the integer V is a 6,8-diazabicyclo[3.2.2]-nonane ring system.

Typically, Y represents a covalent bond, or a linker group selected from —C(O)—, —S(O)$_2$—, —C(O)O—, —C(O)N(R$^4$)— and —S(O)$_2$N(R$^4$)—;

Suitably, Y represents a covalent bond, or a linker group selected from —C(O)— and —C(O)N(R$^4$)—.

Suitable values of Y include —C(O)—, —S(O)—, —S(O)$_2$—, —C(O)O—, —C(O)N(R$^4$)— and —S(O)$_2$N(R$^4$)—.

Particular values of Y include —C(O)—, —S(O)$_2$—, —C(O)O—, —C(O)N(R$^4$)— and —S(O)$_2$N(R$^4$)—.

Selected values of Y include —C(O)— and —C(O)N(R$^4$)—.

In a first embodiment, Y represents a covalent bond. In a second embodiment, Y represents —C(O)—. In a third embodiment, Y represents —S(O)—. In a fourth embodiment, Y represents —S(O)$_2$—. In a fifth embodiment, Y represents —C(O)—. In a sixth embodiment, Y represents —C(O)N(R$^4$)—. In a seventh embodiment, Y represents —S(O)$_2$N(R$^4$)—.

In one aspect, Z represents hydrogen. In an alternative aspect, Z represents C$_{1-6}$ alkyl, C$_{3-7}$ cycloalkyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$)alkyl, any of which groups may be optionally substituted by one or more substituents;

Suitably, Z represents hydrogen; or C$_{1-6}$ alkyl, C$_{3-7}$ cycloalkyl or aryl, any of which groups may be optionally substituted by one or more substituents.

In a first embodiment, Z represents hydrogen. In a second embodiment, Z represents $C_{1-6}$ alkyl, which group may be optionally substituted by one or more substituents. In a third embodiment, Z represents $C_{3-7}$ cycloalkyl, which group may be optionally substituted by one or more substituents. In a fourth embodiment, Z represents $C_{3-7}$ cycloalkyl($C_{1-6}$)alkyl, which group may be optionally substituted by one or more substituents. In a fifth embodiment, Z represents aryl, which group may be optionally substituted by one or more substituents. In a sixth embodiment, Z represents aryl($C_{1-6}$)-alkyl, which group may be optionally substituted by one or more substituents. In a seventh embodiment, Z represents $C_{3-7}$ heterocycloalkyl, which group may be optionally substituted by one or more substituents. In an eighth embodiment, Z represents $C_{3-7}$ heterocycloalkyl($C_{1-6}$)alkyl, which group may be optionally substituted by one or more substituents. In a ninth embodiment, Z represents heteroaryl, which group may be optionally substituted by one or more substituents. In a tenth embodiment, Z represents heteroaryl($C_{1-6}$)alkyl, which group may be optionally substituted by one or more substituents.

Selected values of Z include hydrogen; and methyl, cyclopropyl, 1,2,3,4-tetrahydronaphthyl, cyclopentylethyl, phenyl, benzyl, phenylethyl, phenylpropyl, phenylbutyl, pyrrolidinyl, piperidinyl, 1,2,3,4-tetrahydroisoquinolinyl, piperazinylmethyl, morpholinylmethyl, piperazinylethyl, morpholinylethyl, indolyl, pyrazolyl, indazolyl, imidazolyl, benzimidazolyl, imidazo[1,2-c]pyridinyl, pyridinyl, quinolinyl, isoquinolinyl, pyrazinyl, quinoxalinyl, thienylmethyl, pyridinylmethyl, furylethyl, indolylethyl, imidazolylethyl, benzimidazolylethyl or pyridinylethyl, any of which groups may be optionally substituted by one or more substituents.

Suitable values of Z include hydrogen; and methyl, cyclopropyl or phenyl, any of which groups may be optionally substituted by one or more substituents.

In a particular embodiment, Z is other than hydrogen.

In one embodiment, Z is unsubstituted. In another embodiment, Z is substituted by one or more substituents, typically by one or two substituents. In one aspect of that embodiment, Z is monosubstituted. In another aspect of that embodiment, Z is disubstituted.

Typical examples of optional substituents on Z include one or more substituents independently selected from halogen, cyano, nitro, $C_{1-6}$ alkyl, trifluoromethyl, hydroxy, oxo, $C_{1-6}$ alkoxy, difluoromethoxy, trifluoromethoxy, aryloxy, haloaryloxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, arylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aminocarbonyl, $C_{1-6}$ alkylamino carbonyl, di($C_{1-6}$)alkylaminocarbonyl, aminosulfonyl, $C_{1-6}$ alkylaminosulfonyl and di($C_{1-6}$)alkylaminosulfonyl. Additional examples include aryl, ($C_{1-6}$)alkoxyaryl, ($C_{1-6}$)alkyl($C_{3-7}$)heterocycloalkyl, ($C_{3-7}$)heterocycloalkyl($C_{1-6}$)alkyl, hydroxy($C_{1-6}$)alkyl, ($C_{1-6}$)alkoxyaryloxy, ($C_{1-3}$)alkylenedioxy and N—[($C_{2-6}$)-alkoxycarbonyl]-N—[($C_{1-6}$)alkyl] amino.

Selected examples of optional substituents on Z include one or more substituents independently selected from halogen, cyano, $C_{1-6}$ alkyl, aryl, ($C_{1-6}$)alkoxyaryl, ($C_{1-6}$)alkyl-($C_{3-7}$)heterocycloalkyl, ($C_{3-7}$)heterocycloalkyl($C_{1-6}$)alkyl, hydroxy, hydroxy($C_{1-6}$)alkyl, $C_{1-6}$ alkoxy, difluoromethoxy, trifluoromethoxy, aryloxy, haloaryloxy, ($C_{1-6}$)alkoxyaryloxy, ($C_{1-3}$)alkylenedioxy, $C_{1-6}$ alkylamino, di($C_{1-6}$)alkylamino, N—[($C_{2-6}$)-alkoxycarbonyl]-N—[($C_{1-6}$)alkyl]amino and $C_{2-6}$ alkoxycarbonyl.

Suitable examples of optional substituents on Z include one or more substituents independently selected from halogen, cyano, $C_{1-6}$ alkyl, $C_{1-6}$ alkoxy, haloaryloxy and di($C_{1-6}$) alkylamino.

Typical examples of specific substituents on Z include fluoro, chloro, bromo, cyano, nitro, methyl, isopropyl, trifluoromethyl, hydroxy, oxo, methoxy, difluoromethoxy, trifluoromethoxy, phenoxy, chlorophenoxy, methylthio, methylsulfinyl, methylsulfonyl, amino, methylamino, tert-butylamino, dimethylamino, phenylamino, acetylamino, methoxycarbonylamino, methylsulfonylamino, formyl, acetyl, cyclopropylcarbonyl, azetidinylcarbonyl, pyrrolidinylcarbonyl, piperidinylcarbonyl, piperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylaminosulfonyl. Additional examples include phenyl, methoxyphenyl, methylpiperazinyl, piperidinylmethyl, morpholinylmethyl, hydroxymethyl, ethoxy, methoxyphenoxy, methylenedioxy, N-(tert-butoxycarbonyl)-N-(methyl)amino and tert-butoxycarbonyl.

Selected examples of specific substituents on Z include fluoro, chloro, cyano, methyl, isopropyl, phenyl, methoxyphenyl, methylpiperazinyl, piperidinylmethyl, morpholinylmethyl, hydroxy, hydroxymethyl, methoxy, ethoxy, difluoromethoxy, trifluoromethoxy, phenoxy, chlorophenoxy, methoxyphenoxy, methylenedioxy, methylamino, dimethylamino, N-(tert-butoxycarbonyl)-N-(methyl)amino and tert-butoxycarbonyl.

Suitable examples of specific substituents on Z include chloro, cyano, methyl, isopropyl, methoxy, chlorophenoxy and dimethylamino.

Definitive values of Z include hydrogen, methyl, phenoxymethyl, chlorophenoxymethyl, methoxyphenoxymethyl, dimethylaminomethyl, cyclopropyl, phenylcyclopropyl, methoxyphenylcyclopropyl, 1,2,3,4-tetrahydronaphthyl, cyclopentylethyl, phenyl, fluorophenyl, difluorophenyl, chlorophenyl, cyanophenyl, methylphenyl, isopropylphenyl, methylpiperazinylphenyl, piperidinylmethylphenyl, morpholinylmethylphenyl, methoxy-phenyl, (chloro)(methoxy)phenyl, (methoxy)(methyl)phenyl, dimethoxyphenyl, ethoxy-phenyl, difluoromethoxyphenyl, trifluoromethoxyphenyl, methylenedioxyphenyl, dimethylaminophenyl, benzyl, methylbenzyl, methoxybenzyl, dimethoxybenzyl, methylaminobenzyl, dimethylaminobenzyl, N-(tert-butoxycarbonyl)-N-(methyl)amino-benzyl, phenylethyl, fluorophenylethyl, methylphenylethyl, hydroxyphenylethyl, methoxyphenylethyl, (chloro)(methoxy)phenylethyl, phenylpropyl, phenylbutyl, methyl-pyrrolidinyl, tert-butoxycarbonylpiperidinyl, 1,2,3,4-tetrahydroisoquinolinyl, tert-butoxy-carbonyl-1,2,3,4-tetrahydroisoquinolinyl, methylpiperazinylmethyl, morpholinylmethyl, methylpiperazinylethyl, morpholinylethyl, indolyl, pyrazolyl, methylpyrazolyl, indazolyl, methylimidazolyl, benzimidazolyl, imidazo[1,2-c]pyridinyl, pyridinyl, hydroxymethyl-pyridinyl, quinolinyl, isoquinolinyl, pyrazinyl, quinoxalinyl, thienylmethyl, pyridinylmethyl, furylethyl, indolylethyl, methylimidazolylethyl, benzimidazolylethyl and pyridinylethyl.

Specific values of Z include hydrogen, methyl, chlorophenoxymethyl, cyclopropyl, chlorophenyl, cyanophenyl, methylphenyl, isopropylphenyl, methoxyphenyl and dimethylaminophenyl.

A particular value of Z is chlorophenoxymethyl.

One selected value of Z is methoxyphenyl, especially 4-methoxyphenyl.

Another selected value of Z is (methoxy)(methyl)phenyl, especially 4-methoxy-2-methylphenyl.

Suitably, A represents hydrogen or trifluoromethyl; or $C_{1-6}$ alkyl, optionally substituted by —$OR^a$.

Appositely, A represents hydrogen; or $C_{1-6}$ alkyl, optionally substituted by —$OR^a$.

Illustrative values of A include hydrogen, methyl, hydroxymethyl and trifluoromethyl.

Suitable values of A include hydrogen, methyl and trifluoromethyl.

Selected values of A include hydrogen, methyl and hydroxymethyl.

In a particular embodiment, A represents hydrogen. In another embodiment, A represents trifluoromethyl. In a further embodiment, A represents $C_{1-6}$ alkyl, optionally substituted by one or more substituents independently selected from —$OR^a$ and —$NR^bR^c$. In a first aspect of that embodiment, A represents unsubstituted $C_{1-6}$ alkyl, especially methyl. In a second aspect of that embodiment, A represents $C_{1-6}$ alkyl monosubstituted by —$OR^a$ or —$NR^bR^c$. In a third aspect of that embodiment, A represents $C_{1-6}$ alkyl disubstituted by two substituents independently selected from —$OR^a$ and —$NR^bR^c$. In a particular feature of the second aspect, A represents $C_{1-6}$ alkyl monosubstituted by —$OR^a$, e.g. hydroxymethyl.

Generally, $R^1$ and $R^2$ independently represent hydrogen, halogen, cyano, nitro, hydroxy, trifluoromethyl, trifluoromethoxy, —$OR^a$, —$SR^a$, —$SOR^a$, —$SO_2R^a$, —$NR^bR^c$, —$CH_2NR^bR^c$, —$NR^cCOR^d$, —$CH_2NR^cCOR^d$, —$NR^cCO_2R^d$, —$NHCONR^bR^c$, —$NR^cSO_2R^e$, —$N(SO_2R^e)_2$, —$NHSO_2NR^bR^c$, —$COR^d$, —$CO_2R^d$, —$CONR^bR^c$, —$CON(OR^a)R^b$ or —$SO_2NR^bR^c$; or $C_{1-6}$ alkyl, aryl, aryl($C_{1-6}$)alkyl, heteroaryl or heteroaryl($C_{1-6}$) alkyl, any of which groups may be optionally substituted by one or more substituents.

Suitably, $R^1$ represents hydrogen, halogen, cyano, nitro, hydroxy, trifluoromethyl, trifluoromethoxy, —$OR^a$, —$SO_2R^a$, —$NR^bR^c$, —$CH_2NR^bR^c$, —$NR^cCOR^d$, —$CH_2NR^cCOR^d$, —$NR^cCO_2R^d$, —$NHCONR^bR^c$, —$NR^cSO_2R^e$, —$NHSO_2NR^bR^c$, —$COR^d$, —$CO_2R^d$, —$CONR^bR^c$, —$CON(OR^a)R^b$ or —$SO_2NR^bR^c$; or $C_{1-6}$ alkyl, aryl or heteroaryl, any of which groups may be optionally substituted by one or more substituents.

Typically, $R^1$ represents hydrogen, —$NR^bR^c$ or —$NR^cCOR^d$; or $C_{1-6}$ alkyl, which group may be optionally substituted by one or more substituents.

Suitable values of $R^1$ include hydrogen and —$NR^bR^c$.

In one embodiment, $R^1$ represents hydrogen. In another embodiment, $R^1$ represents —$NR^bR^c$. In a further embodiment, $R^1$ represents —$NR^cCOR^d$. In an additional embodiment, $R^1$ represents optionally substituted $C_{1-6}$ alkyl. In one aspect of that embodiment, $R^1$ represents optionally substituted methyl.

Examples of typical substituents on $R^1$ include one or more substituents independently selected from halogen, cyano, nitro, $C_{1-6}$ alkyl, trifluoromethyl, aryl($C_{1-6}$)alkyl, hydroxy, $C_{1-6}$ alkoxy, difluoromethoxy, trifluoromethoxy, aryloxy, $C_{1-4}$ alkylenedioxy, $C_{1-6}$ alkoxy($C_{1-6}$)alkyl, $C_{1-6}$ alkylthio, $C_{1-6}$ alkylsulphonyl, oxo, amino, $C_{1-6}$ alkylamino, di($C_{1-6}$) alkylamino, $C_{2-6}$ alkylcarbonylamino, $C_{2-6}$ alkoxycarbonylamino, aryl($C_{1-6}$)alkoxycarbonylamino, $C_{1-6}$ alkylaminocarbonylamino, arylaminocarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylamino sulphonyl and di($C_{1-6}$)alkylaminosulphonyl.

Specific examples of typical substituents on $R^1$ include one or more substituents independently selected from fluoro, chloro, bromo, cyano, nitro, methyl, ethyl, tert-butyl, trifluoromethyl, benzyl, hydroxy, methoxy, difluoromethoxy, trifluoromethoxy, phenoxy, methylenedioxy, ethylenedioxy, methoxymethyl, methylthio, methylsulphonyl, oxo, amino, methylamino, dimethylamino, acetylamino, methoxycarbonylamino, ethoxycarbonylamino, benzyloxycarbonylamino, ethylaminocarbonylamino, butylaminocarbonylamino, phenylaminocarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl.

Appositely, $R^2$ represents hydrogen, cyano, hydroxy, trifluoromethyl, —$NR^cCO_2R^d$, —$CO_2R^d$, —$CONR^bR^c$ or —$CON(OR^a)R^b$; or $C_{1-6}$ alkyl, $C_{3-7}$ cycloalkyl, aryl or heteroaryl, any of which groups may be optionally substituted by one or more substituents.

Typically, $R^2$ represents —$COR^d$, —$CO_2R^d$, —$CONR^bR^c$ or —$CON(OR^a)R^b$; or $C_{1-6}$ alkyl, aryl or heteroaryl, any of which groups may be optionally substituted by one or more substituents.

Suitably, $R^2$ represents —$CO_2R^d$, —$CONR^bR^c$ or —$CON(OR^a)R^b$; or $C_{1-6}$ alkyl, aryl or heteroaryl, any of which groups may be optionally substituted by one or more substituents.

In a first embodiment, $R^2$ represents hydrogen. In a second embodiment, $R^2$ represents cyano. In a third embodiment, $R^2$ represents hydroxy. In a fourth embodiment, $R^2$ represents trifluoromethyl. In a fifth embodiment, $R^2$ represents —$NR^cCO_2R^d$. In a sixth embodiment, $R^2$ represents —$COR^d$. In a seventh embodiment, $R^2$ represents —$CO_2R^d$. In an eighth embodiment, $R^2$ represents —$CONR^bR^c$. In a ninth embodiment, $R^2$ represents —$CON(OR^a)R^b$. In a tenth embodiment, $R^2$ represents optionally substituted $C_{1-6}$ alkyl. In a first aspect of that embodiment, $R^2$ represents unsubstituted $C_{1-6}$ alkyl. In a second aspect of that embodiment, $R^2$ represents monosubstituted $C_{1-6}$ alkyl. In a third aspect of that embodiment, $R^2$ represents disubstituted $C_{1-6}$ alkyl. In an eleventh embodiment, $R^2$ represents optionally substituted $C_{3-7}$ cycloalkyl. In a first aspect of that embodiment, $R^2$ represents unsubstituted $C_{3-7}$ cycloalkyl. In a second aspect of that embodiment, $R^2$ represents monosubstituted $C_{3-7}$ cycloalkyl. In a third aspect of that embodiment, $R^2$ represents disubstituted $C_{3-7}$ cycloalkyl. In a twelfth embodiment, $R^2$ represents optionally substituted aryl. In a first aspect of that embodiment, $R^2$ represents unsubstituted aryl. In a second aspect of that embodiment, $R^2$ represents monosubstituted aryl. In a third aspect of that embodiment, $R^2$ represents disubstituted aryl. In a thirteenth embodiment, $R^2$ represents optionally substituted heteroaryl. In a first aspect of that embodiment, $R^2$ represents unsubstituted heteroaryl. In a second aspect of that embodiment, $R^2$ represents monosubstituted heteroaryl. In a third aspect of that embodiment, $R^2$ represents disubstituted heteroaryl.

Where $R^2$ represents optionally substituted $C_{1-6}$ alkyl, suitable values include methyl, ethyl, n-propyl, isopropyl, n-butyl, isobutyl and tert-butyl, any of which groups may be optionally substituted by one or more substituents. Selected values include methyl, hydroxymethyl, chloropropyl and isobutyl. Particular values include methyl and isobutyl.

Where $R^2$ represents optionally substituted $C_{3-7}$ cycloalkyl, a suitable value is cyclohexyl, optionally substituted by one or more substituents.

Where $R^2$ represents optionally substituted aryl, a suitable value is phenyl, optionally substituted by one or more substituents. Selected values include phenyl, fluorophenyl, chlorophenyl and methoxyphenyl.

Where $R^2$ represents optionally substituted heteroaryl, suitable values include pyrrolyl, furyl, thienyl, imidazolyl, oxazolyl, isoxazolyl, thiazolyl, isothiazolyl, pyrazolyl, triazolyl, oxadiazolyl, thiadiazolyl, pyridinyl, pyrimidinyl, pyridazinyl, pyrazinyl, tetrazolyl and triazinyl, any of which groups may be optionally substituted by one or more substituents. Suitable values include oxadiazolyl and pyridinyl, either of which groups may be optionally substituted by one or more substituents. Selected values include methyloxadiazolyl, isopropyloxadiazolyl, tert-butyloxadiazolyl and pyridinyl.

In a selected embodiment, $R^2$ represents hydrogen, cyano, hydroxy, trifluoromethyl, —NR$^c$CO$_2$R$^d$, —CO$_2$R$^d$, —CONR$^b$R$^c$ or —CON(OR$^a$)R$^b$; or $C_{1-6}$ alkyl, cyclohexyl, phenyl, oxadiazolyl or pyridinyl, any of which groups may be optionally substituted by one or more substituents.

In a suitable embodiment, $R^2$ represents —CO$_2$R$^d$, —CONR$^b$R$^c$ or —CON(OR$^a$)R$^b$; or $C_{1-6}$ alkyl, phenyl or pyridinyl, any of which groups may be optionally substituted by one or more substituents.

Typical examples of optional substituents on $R^2$ include one or more substituents independently selected from halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Selected examples of optional substituents on $R^2$ include one or more substituents independently selected from halogen, $C_{1-6}$ alkyl, hydroxy and $C_{1-6}$ alkoxy.

A suitable example of an optional substituent on $R^2$ is halogen.

Typical examples of specific substituents on $R^2$ include one or more substituents independently selected from fluoro, chloro, bromo, cyano, nitro, methyl, ethyl, isopropyl, trifluoromethyl, hydroxy, methoxy, isopropoxy, difluoromethoxy, trifluoromethoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, aminocarbonyl, methylaminocarbonyl, dimethylaminocarbonyl, aminosulfonyl, methylaminosulfonyl and dimethylaminosulfonyl. An additional example is tert-butyl.

Selected examples of specific substituents on $R^2$ include one or more substituents independently selected from fluoro, chloro, methyl, isopropyl, tert-butyl, hydroxy and methoxy.

A suitable example of a specific substituent on $R^2$ is fluoro.

Selected values of $R^2$ include hydrogen, cyano, hydroxy, trifluoromethyl, —NR$^c$CO$_2$R$^d$, —CO$_2$R$^d$, —CONR$^b$R$^c$, —CON(OR$^a$)R$^b$, methyl, hydroxymethyl, chloropropyl, isobutyl, cyclohexyl, phenyl, fluorophenyl, chlorophenyl, methoxyphenyl, methyloxadiazolyl, isopropyloxadiazolyl, tert-butyloxadiazolyl and pyridinyl, any of which groups may be optionally substituted by one or more substituents.

Individual values of $R^2$ include —CO$_2$R$^d$, —CONR$^b$R$^c$, —CON(OR$^a$)R$^b$, methyl, isobutyl, phenyl, fluorophenyl and pyridinyl.

Apposite values of $R^2$ include hydrogen, cyano and —CO$_2$R$^d$.

Particular values of $R^2$ include cyano and —CO$_2$R$^d$.

Suitably, $R^3$ represents hydrogen or $C_{1-6}$ alkyl.

Suitable values of $R^3$ include hydrogen and methyl.

In one embodiment, $R^3$ represents hydrogen. In another embodiment, $R^3$ represents $C_{1-6}$ alkyl, optionally substituted by one or more substituents independently selected from —OR$^a$ and —NR$^b$R$^c$. In one aspect of that embodiment, $R^3$ represents unsubstituted $C_{1-6}$ alkyl, especially methyl. In another aspect of that embodiment, $R^3$ represents $C_{1-6}$ alkyl monosubstituted by —OR$^a$ or —NR$^b$R$^c$. In a further aspect of that embodiment, $R^3$ represents $C_{1-6}$ alkyl disubstituted by two substituents independently selected from —OR$^a$ and —NR$^b$R$^c$.

Suitably, $R^4$ represents hydrogen or $C_{1-6}$ alkyl.

Suitable values of $R^4$ include hydrogen and methyl.

In one embodiment, $R^4$ represents hydrogen. In another embodiment, $R^4$ represents $C_{1-6}$ alkyl, optionally substituted by one or more substituents independently selected from —OR$^a$ and —NR$^b$R$^c$. In one aspect of that embodiment, $R^4$ represents unsubstituted $C_{1-6}$ alkyl, especially methyl. In another aspect of that embodiment, $R^4$ represents $C_{1-6}$ alkyl monosubstituted by —OR$^a$ or —NR$^b$R$^c$. In a further aspect of that embodiment, $R^4$ represents $C_{1-6}$ alkyl disubstituted by two substituents independently selected from —OR$^a$ and —NR$^b$R$^c$.

Typical examples of suitable substituents on $R^a$, $R^b$, $R^c$, $R^d$ or $R^e$, or on the heterocyclic moiety —NR$^b$R$^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylamino carbonyl.

Typical examples of specific substituents on $R^a$, $R^b$, $R^c$, $R^d$ or $R^e$, or on the heterocyclic moiety —NR$^b$R$^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, acetylaminomethyl, tert-butoxycarbonylamino, methylsulphonylamino, aminocarbonyl, methylaminocarbonyl and dimethylaminocarbonyl.

Illustratively, $R^a$ represents hydrogen; or $R^a$ represents $C_{1-6}$ alkyl, aryl($C_{1-6}$)alkyl or heteroaryl($C_{1-6}$)alkyl, any of which groups may be optionally substituted by one or more substituents.

Typically, $R^a$ represents $C_{1-6}$ alkyl, aryl, aryl($C_{1-6}$)alkyl, heteroaryl or heteroaryl-($C_{1-6}$)alkyl, any of which groups may be optionally substituted by one or more substituents.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Appositely, $R^a$ represents hydrogen; or $R^a$ represents $C_{1-6}$ alkyl, which group may be optionally substituted by one or more substituents.

Particular values of $R^a$ include hydrogen; and methyl, ethyl, benzyl and isoindolylpropyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo.

Selected examples of specific substituents on $R^a$ include methoxy and oxo.

In one embodiment, $R^a$ represents hydrogen. In another embodiment, $R^a$ represents optionally substituted $C_{1-6}$ alkyl.

In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl.

Specific values of $R^a$ include methyl, methoxyethyl, benzyl and dioxoisoindolylpropyl.

Generally, $R^a$ represents hydrogen or $C_{1-6}$ alkyl.

Individual values of $R^a$ include hydrogen and methyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents.

Selected values of $R^b$ include hydrogen; and $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Appositely, $R^b$ represents hydrogen; or $C_{1-6}$ alkyl, which group may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; and methyl, ethyl, n-propyl, benzyl, pyrrolidinyl or morpholinylpropyl, any of which groups may be optionally substituted by one or more substituents. An additional value of $R^b$ is optionally substituted tert-butyl.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$)alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

A particular optional substituent on $R^b$ is hydroxy.

Specific values of $R^b$ include hydrogen, methyl, methoxyethyl, methylthioethyl, methylsulphinylethyl, methylsulphonylethyl, hydroxyethyl, cyanoethyl, dimethylamino-ethyl, tert-butoxycarbonylaminoethyl, dihydroxypropyl, benzyl, pyrrolidinyl, tert-butoxycarbonylpyrrolidinyl and morpholinylpropyl. An additional specific value of $R^b$ is 1,1-dimethyl-2-hydroxyethyl.

In one embodiment, $R^b$ represents hydrogen. In another embodiment, $R^b$ represents $C_{1-6}$ alkyl, especially methyl. In a further embodiment, $R^b$ represents hydroxy($C_{1-6}$)alkyl, especially 1,1-dimethyl-2-hydroxyethyl.

Particular values of $R^b$ include hydrogen, methyl and 1,1-dimethyl-2-hydroxyethyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl, Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxy-carbonylamino, methylsulphonylamino and aminocarbonyl.

Specific values of the moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, amino azetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxo-isothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl or ethyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl. In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl. In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl. In a further embodiment, $R^d$ represents optionally substituted $C_{3-7}$ heterocycloalkyl, e.g. thiazolidinyl or oxothiazolidinyl.

Selected examples of specific values for $R^d$ include hydrogen, methyl, ethyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Generally, $R^d$ represents hydrogen or $C_{1-6}$ alkyl.

Apposite values of $R^d$ include hydrogen and ethyl.

A particular value of $R^d$ is ethyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

One sub-class of compounds according to the invention is represented by the compounds of formula (IIA), and pharmaceutically acceptable salts and solvates thereof:

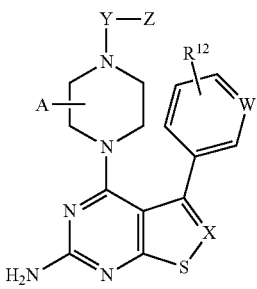

(IIA)

wherein X, Y, Z and A are as defined above;

W represents $C-R^{11}$ or N;

$R^{11}$ represents hydrogen, halogen, cyano, $C_{1-6}$ alkyl, trifluoromethyl, hydroxy, $C_{1-6}$ alkoxy, trifluoromethoxy or $C_{1-6}$ alkylaminosulphonyl; and $R^{12}$ represents hydrogen, halogen, cyano, nitro, $C_{1-6}$ alkyl, trifluoromethyl, hydroxy, $C_{1-6}$ alkoxy, trifluoromethoxy, $C_{1-6}$ alkylthio, $C_{1-6}$ alkylsulphonyl, amino or di($C_{1-6}$)alkylamino.

In one embodiment, W is $C-R^{11}$. In another embodiment, W is N.

Suitably, $R^{11}$ represents hydrogen or halogen.

Typical values of $R^{11}$ include hydrogen, fluoro, chloro, cyano, methyl, trifluoromethyl, hydroxy, methoxy, trifluoromethoxy and methylaminosulphonyl.

Selected values of $R^{11}$ include hydrogen and fluoro.

In a particular embodiment, $R^{11}$ represents hydrogen.

In another embodiment, $R^{11}$ represents halogen, especially fluoro.

Typically, $R^{12}$ represents hydrogen, halogen or $C_{1-6}$ alkoxy.

Suitable values of $R^{12}$ include hydrogen, fluoro, chloro, bromo, cyano, nitro, methyl, trifluoromethyl, hydroxy, methoxy, trifluoromethoxy, methylthio, methylsulphonyl, amino and dimethylamino.

Selected values of $R^{12}$ include hydrogen, fluoro, chloro and methoxy.

Suitably, $R^{12}$ represents hydrogen or halogen.

In one embodiment, $R^{12}$ represents hydrogen. In another embodiment, $R^{12}$ represents halogen. In one aspect of that embodiment, $R^{12}$ represents fluoro. In another aspect of that embodiment, $R^{12}$ represents chloro. In another embodiment, $R^{12}$ represents $C_{1-6}$ alkoxy. In one aspect of that embodiment, $R^{12}$ represents methoxy.

Another sub-class of compounds according to the invention is represented by the compounds of formula (IIB), and pharmaceutically acceptable salts and solvates thereof:

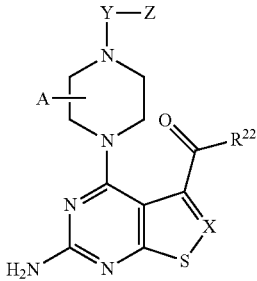

(IIB)

wherein

R²² represents —$R^d$, —$OR^d$, —$NR^bR^c$ or —$N(OR^a)R^b$; and

X, Y, Z, A, $R^a$, $R^b$, $R^c$ and $R^d$ are as defined above.

In a first embodiment, $R^{22}$ represents —$R^d$. In a second embodiment, $R^{22}$ represents —$OR^d$. In a third embodiment, $R^{22}$ represents —$NR^bR^c$. In a fourth embodiment, $R^{22}$ represents —$N(OR^a)R^b$.

The present invention also provides a compound of formula (IIA) or (IIB) as depicted above, or a pharmaceutically acceptable salt or solvate thereof, wherein A represents hydrogen; and X, Y, Z and $R^{22}$ are as defined above.

Another sub-class of compounds according to the invention is represented by the compounds of formula (IIC), and pharmaceutically acceptable salts and solvates thereof:

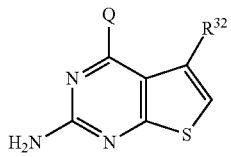

(IIC)

wherein $R^{32}$ represents cyano or —$CO_2R^d$; and

Q and $R^d$ are as defined above.

In a first embodiment, $R^{32}$ represents cyano.

In a second embodiment, $R^{32}$ represents —$CO_2R^d$.

A particular subgroup of the compounds of formula (IIC) is represented by the compounds of formula (IIC-1), and pharmaceutically acceptable salts and solvates thereof:

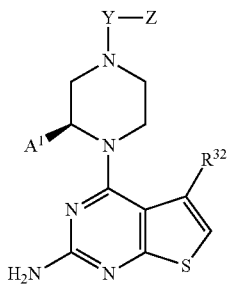

(IIC-1)

wherein $A^1$ represents hydrogen or methyl; and

Y, Z and $R^{32}$ are as defined above.

In a first embodiment, $A^1$ represents hydrogen.

In a second embodiment, $A^1$ represents methyl.

Another sub-class of compounds according to the invention is represented by the compounds of formula (IID), and pharmaceutically acceptable salts and solvates thereof:

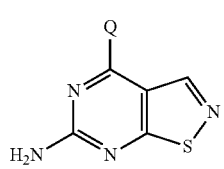

(IID)

wherein

Q is as defined above.

A particular subgroup of the compounds of formula (IID) is represented by the compounds of formula (IID-1), and pharmaceutically acceptable salts and solvates thereof:

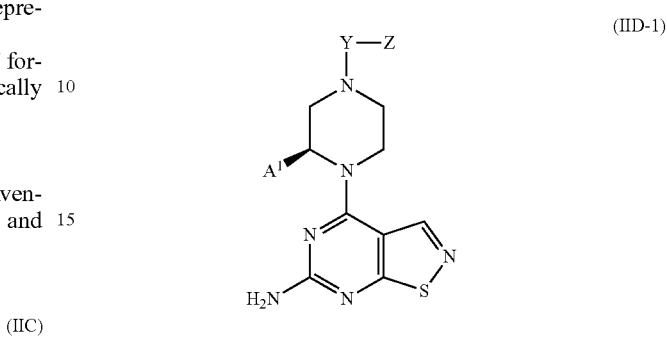

(IID-1)

wherein

Y, Z and $A^1$ are as defined above.

Specific novel compounds in accordance with the present invention include each of the compounds whose preparation is described in the accompanying Examples, and pharmaceutically acceptable salts and solvates thereof.

The compounds in accordance with the present invention are beneficial in the treatment and/or prevention of various human ailments. These include inflammatory, autoimmune and oncological disorders; viral diseases; and organ and cell transplant rejection.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, vasculitis, polymyositis, scleroderma, multiple sclerosis, ankylosing spondylitis, rheumatoid arthritis and Sjögren's syndrome. Autoimmune endocrine disorders include thyroiditis. Organ-specific autoimmune disorders include Addison's disease, haemolytic or pernicious anaemia, glomerulonephritis (including Goodpasture's syndrome), Graves' disease, idiopathic thrombocytopenic purpura, insulin-dependent diabetes mellitus, juvenile diabetes, uveitis, inflammatory bowel disease (including Crohn's disease and ulcerative colitis), pemphigus, atopic dermatitis, autoimmune hepatitis, primary biliary cirrhosis, autoimmune pneumonitis, autoimmune carditis, myasthenia gravis and spontaneous infertility.

Oncological disorders, which may be acute or chronic, include proliferative disorders, especially cancer, in animals, including mammals, especially humans. Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle.

Viral diseases include infections caused by various families of virus, including the Retroviridae, Flaviviridae, Picornaviridae. Various genera within the Retroviridae family include Alpharetrovirus, Betaretrovirus, Gammaretrovirus, Deltaretrovirus, Epsilonretrovirus, Lentivirus and Spumavirus. Members of the Lentivirus genus include human immunodeficiency virus 1 (HIV-1) and human immunodeficiency virus 2 (HIV-2). Various genera within the Flaviviridae family include Flavivirus, Pestivirus, Hepacivirus and Hepatitis G Virus. Members of the Flavivirus genus include Dengue fever virus, yellow fever virus, West Nile encephalitis virus and Japanese encephalitis virus. Members of the Pestivirus genus include bovine viral diarrhoea virus (BVDV), classical swine fever virus and border disease virus 2 (BDV-2). Members of the Hepacivirus genus include hepatitis C virus (HCV). Members of the Hepatitis G Virus genus include hepatitis G virus. Various genera within the Picornaviridae family include Aphthovirus, Avihepatovirus, Cardiovirus, Enterovirus, Erbovirus, Hepatovirus, Kobuvirus, Parechovirus, Sapelovirus, Senecavirus, Teschovirus and Tremovirus. Members of the Enterovirus genus include poliovirus, coxsackie A virus, coxsackie B virus and rhinovirus.

Organ transplant rejection includes the rejection of transplanted or grafted organs or cells (both allografts and xenografts), including graft-versus-host reaction disease. The term "organ" as used herein means all organs or parts of organs in mammals, particularly humans, including kidney, lung, bone marrow, hair, cornea, eye (vitreous), heart, heart valve, liver, pancreas, blood vessel, skin, muscle, bone, intestine and stomach. The term "rejection" as used herein means all reactions of the recipient body or the transplanted organ which ultimately lead to cell or tissue death in the transplanted organ, or adversely affect the functional ability and viability of the transplanted organ or the recipient. In particular, this means acute and chronic rejection reactions.

Cell transplant rejection includes the rejection of cell transplants and xenotransplantation. The major hurdle for xenotransplantation is that even before the T lymphocytes (responsible for the rejection of allografts) are activated, the innate immune system (especially T-independent B lymphocytes and macrophages) is activated. This provokes two types of severe and early acute rejection, referred to as hyperacute rejection and vascular rejection respectively. Conventional immunosuppressant drugs, including cyclosporine A, are ineffective in xenotransplantation. The compounds in accordance with the present invention are not liable to this drawback. The ability of the compounds of this invention to suppress T-independent xeno-antibody production as well as macrophage activation may be demonstrated by their ability to prevent xenograft rejection in athymic, T-deficient mice receiving xenogenic hamster-heart grafts.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above may be prepared by a process which comprises reacting a compound of formula (III) with a compound of formula (IV):

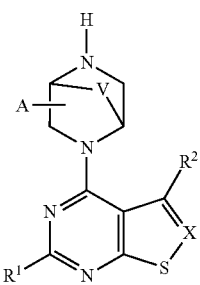

(III)

Q—H (IV)

wherein Q, X, $R^1$ and $R^2$ are as defined above, and $L^1$ represents a suitable leaving group.

The leaving group $L^1$ is typically a halogen atom, e.g. chloro.

The reaction is conveniently effected at ambient temperature in a suitable solvent, e.g. a chlorinated solvent such as dichloromethane.

In an alternative procedure, the compounds of formula (I) above wherein Y represents —C(O)—, —S(O)$_2$— or —C(O)O— may be prepared by a process which comprises reacting a compound of formula $L^2$-C(O)—Z, $L^2$-S(O)$_2$—Z or $L^2$-C(O)O—Z respectively with a compound of formula (VA) or (VB):

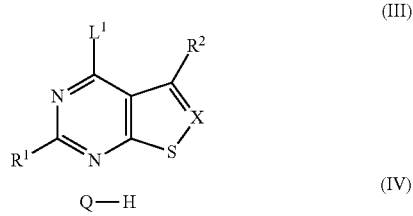

(VA)

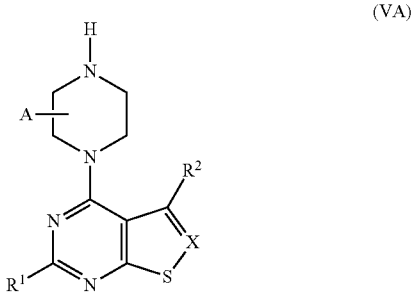

(VB)

wherein V, X, Z, A, $R^1$ and $R^2$ are as defined above, and $L^2$ represents a suitable leaving group.

The leaving group $L^2$ is typically a halogen atom, e.g. chloro.

The reaction is conveniently effected at ambient temperature in a suitable solvent, e.g. an ethereal solvent such as 1,4-dioxane, typically in the presence of a base. A suitable base for use in the reaction may be an organic base such as N,N-diisopropylethylamine, or an inorganic base such as potassium carbonate.

Alternatively, the leaving group $L^2$ may be 2-methyl-3-(trifluoromethylsulfonyl)-1H-imidazol-3-ium-1-yl, in which case the reaction may conveniently be effected at ambient temperature in an organic solvent such as acetonitrile.

In a variant procedure, the compounds of formula (I) above wherein Y represents —C(O)— may be prepared by a process which comprises reacting a compound of formula (VA) or (VB) as defined above with a compound of formula Z—CO$_2$H.

The reaction is conveniently effected at ambient temperature in a suitable solvent, e.g. a dipolar aprotic solvent such as N,N-dimethylformamide, typically in the presence of a coupling agent and a base. A suitable coupling agent for use in the reaction may be O-(7-azabenzotriazol-1-yl)-N,N,N',N'-tetramethyluronium hexafluorophosphate (HATU). A suitable base for use in the reaction may be an organic base such as N,N-diisopropylethylamine.

In another procedure, the compounds of formula (I) above wherein Y represents —C(O)NH— may be prepared by a process which comprises reacting a compound of formula (VA) or (VB) as defined above with an isocyanate derivative of formula Z—N=C=O, wherein Z is as defined above.

The reaction is conveniently effected at ambient temperature in a suitable solvent or mixture of solvents. Such solvent or solvents may typically be selected as appropriate from an ethereal solvent such as 1,4-dioxane or tetrahydrofuran, a chlorinated solvent such as dichloromethane, a nitrile-containing solvent such as acetonitrile, and a dipolar aprotic solvent such as N,N-dimethylformamide. The reaction may optionally be performed in the presence of a base, e.g. an organic base such as diisopropylamine, N,N-diisopropylethylamine or triethylamine.

In a further procedure, the compounds of formula (I) above wherein Y represents —S(O$_2$)NH— may be prepared by a two-step process which comprises: (i) reacting a compound of formula (VA) or (VB) as defined above with methyl trifluoromethanesulfonate; and (ii) reacting the material thereby obtained with a compound of formula Z—NH$_2$, wherein Z is as defined above.

Step (i) of the above process is conveniently effected at a temperature in the region of 0° C. in a suitable solvent, typically a chlorinated solvent such as dichloromethane. Step (ii)

is conveniently effected at an elevated temperature in a suitable solvent, e.g. a nitrile-containing solvent such as acetonitrile.

In a further procedure, the compounds of formula (I) above wherein Y represents a covalent bond, and Z represents optionally substituted $C_{1-6}$ alkyl, optionally substituted $C_{3-7}$ cycloalkyl($C_{1-6}$)alkyl, optionally substituted aryl($C_{1-6}$)alkyl, optionally substituted $C_{3-7}$ heterocycloalkyl($C_{1-6}$)alkyl or optionally substituted heteroaryl($C_{1-6}$)alkyl, may be prepared by a process which comprises reacting a compound of formula (VA) or (VB) as defined above with a compound of formula $Z^1$-$L^3$ wherein $Z^1$ represents $C_{1-6}$ alkyl, $C_{3-7}$ cycloalkyl($C_{1-6}$)alkyl, aryl($C_{1-6}$)alkyl, $C_{3-7}$ heterocycloalkyl($C_{1-6}$)alkyl or heteroaryl($C_{1-6}$)-alkyl, any of which groups may be optionally substituted by one or more substituents, and $L^3$ represents a suitable leaving group.

The leaving group $L^3$ is typically a halogen atom.

The reaction is conveniently effected at ambient temperature in a suitable solvent, e.g. a dipolar aprotic solvent such as N,N-dimethylformamide, or a chlorinated solvent such as dichloromethane, typically in the presence of a base. A suitable base for use in the reaction may be an organic base such as triethylamine, or an inorganic base such as caesium carbonate.

In a variant procedure, the compounds of formula (I) above wherein Y represents a covalent bond, and Z represents optionally substituted $C_{1-6}$ alkyl, optionally substituted $C_{3-7}$ cycloalkyl($C_{1-6}$)alkyl, optionally substituted aryl($C_{1-6}$)alkyl, optionally substituted $C_{3-7}$ heterocycloalkyl($C_{1-6}$)alkyl or optionally substituted heteroaryl($C_{1-6}$)alkyl, may be prepared by a two-step process which comprises: (i) reacting a compound of formula (VA) or (VB) as defined above with a compound of formula $Z^2$—CHO, wherein $Z^2$—$CH_2$—corresponds to a group of formula $Z^1$— as defined above; and (ii) reacting the material thereby obtained with a reducing agent.

Steps (i) and (ii) of the above process are conveniently effected at ambient temperature in a suitable solvent, e.g. a $C_{1-4}$ alkanol such as methanol. Step (i) is typically performed in the presence of a base, e.g. an organic base such as triethylamine. The reducing agent for use in step (ii) may suitably be an alkali metal borohydride such as sodium borohydride.

The intermediates of formula (III) above wherein $L^1$ represents a halogen atom may be prepared by treating a compound of formula (VI):

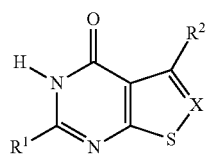

(VI)

wherein X, $R^1$ and $R^2$ are as defined above; with a halogenating agent.

Where $L^1$ in the compounds of formula (III) is chloro, the halogenating agent employed in the above reaction will be a chlorinating reagent. A suitable chlorinating agent is phosphorus oxychloride.

The reaction is conveniently effected by contacting the reagents at an elevated temperature.

Depending upon the substitution pattern around its ring system, the compound of formula (VI) as depicted above may exist predominantly as its hydroxyimine tautomer.

The intermediates of formula (VA) and (VB) above may be prepared by reacting a compound of formula (VI) as defined above with a compound of formula (VIIA) or (VIIB):

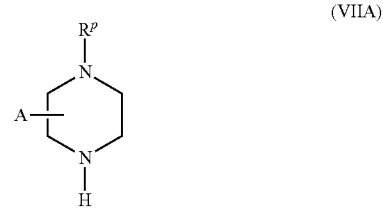

(VIIA)

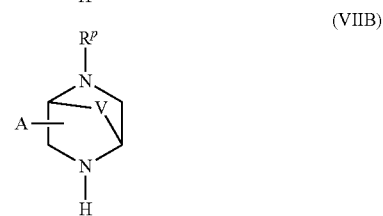

(VIIB)

wherein V and A are as defined above, and $R^p$ represents hydrogen or an N-protecting group; followed, as necessary, by removal of the N-protecting group $R^p$.

The N-protecting group $R^p$ is typically tert-butoxycarbonyl (BOC).

The reaction between compound (VI) and compound (VIIA) or (VIIB) is conveniently accomplished at a suitable temperature (ambient or elevated) in a solvent such as acetonitrile or N,N-dimethylformamide, ideally in the presence of a coupling agent such as benzotriazol-1-yloxytris(dimethylamino)phosphonium hexafluorophosphate (BOP) or (benzotriazol-1-yloxy)tripyrrolidinophosphonium hexafluorophosphate (PyBOP), and a base, e.g. an organic base such as 1,8-diazabicyclo[5.4.0]undec-7-ene (DBU).

Where the N-protecting group $R^p$ is BOC, subsequent removal of the BOC group may typically be accomplished by treatment with an acid, e.g. a mineral acid such as hydrochloric acid, or an organic acid such as trifluoroacetic acid.

As will be appreciated, the intermediates of formula (VA) and (VB) correspond to compounds in accordance with the present invention wherein Y represents a covalent bond and Z is hydrogen. Similarly, the intermediates of formula (VIIA) and (VIIB) wherein $R^p$ is hydrogen correspond to intermediates of formula (IV) wherein Y represents a covalent bond and Z is hydrogen.

Where they are not commercially available, the starting materials of formula (IV), (VI), (VIIA) and (VIIB) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) wherein $R^2$ represents —$CO_2R^d$, in which $R^d$ is other than hydrogen, may be converted into the corresponding compound wherein $R^2$ represents carboxy (—$CO_2H$) by treatment with a base, typically an alkali metal hydroxide such as sodium hydroxide. A compound of formula (I) wherein $R^2$ represents carboxy (—$CO_2H$) may be converted into the corresponding compound wherein $R^2$ represents —$CONR^bR^c$ or —$CON(OR^a)R^b$ by treatment with the appropriate reagent of formula H—$NR^bR^c$ or H—$N(OR^a)R^b$ respectively, typically in the presence of a coupling agent such as 1-(3-dimethylaminopropyl)-3-ethylcarbodiimide hydrochloride (EDC) and an additive such as 1-hydroxybenzotriazole hydrate (HOBT), optionally in the presence of a base, e.g. an organic base such as N,N-diisopropylethylamine.

A compound of formula (I) wherein $R^2$ represents carboxy (—$CO_2H$) may be converted into the corresponding compound wherein $R^2$ represents —$CONH_2$ by treatment with ammonium chloride, typically in the presence of a coupling agent such as EDC and an additive such as HOBT, suitably in the presence of a base, e.g. an organic base such as diisopropylamine or N,N-diisopropylethylamine. A compound of formula (I) wherein $R^2$ represents —$CONH_2$ may be converted into the corresponding compound wherein $R^2$ represents cyano (—CN) by treatment with phosphorus oxychloride. Alternatively, a compound of formula (I) wherein $R^2$ represents —$CONH_2$ may be converted into the corresponding compound wherein $R^2$ represents cyano in a two-step procedure which comprises: (i) treatment with cyanuric chloride; and (ii) treatment of the material thereby obtained with water.

A compound of formula (I) wherein $R^2$ represents carboxy (—$CO_2H$) may be converted into the corresponding compound wherein $R^2$ represents hydroxymethyl (—$CH_2OH$) in a two-step procedure which comprises: (i) treatment with ethyl chloroformate and triethylamine; and (ii) treatment of the material thereby obtained with a reducing agent, typically an alkali metal borohydride such as sodium borohydride.

A compound of formula (I) wherein $R^2$ represents carboxy (—$CO_2H$) may be converted into the corresponding compound wherein $R^2$ represents hydroxy in a two-step procedure which comprises: (i) treatment with diphenyl phosphoryl azide; and (ii) treatment of the material thereby obtained with water.

A compound of formula (I) wherein $R^2$ represents carboxy (—$CO_2H$) may be converted into the corresponding compound wherein $R^2$ represents —$NHCO_2R^d$, wherein $R^d$ is other than hydrogen, in a two-step procedure which comprises: (i) treatment with diphenyl phosphoryl azide; and (ii) treatment of the material thereby obtained with the appropriate reagent of formula $R^d$—OH.

A compound of formula (I) wherein $R^2$ represents carboxy (—$CO_2H$) may be converted into the corresponding compound wherein $R^2$ represents a 3-substituted 1,2,4-oxadiazol-5-yl moiety in a two-step procedure which comprises: (i) treatment with an appropriately-substituted N'-hydroxyamidine derivative, typically in the presence of a coupling agent such as O-(7-azabenzotriazol-1-yl)-N,N,N',N'-tetramethyluronium hexafluorophosphate (HATU), suitably in the presence of a base, e.g. an organic base such as N,N-diisopropylethylamine; and (ii) treatment of the material thereby obtained with a strong base, suitably a strong inorganic base, e.g. an alkali metal tert-butoxide such as potassium tert-butoxide.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, $3^{rd}$ edition, 1999. The protecting groups may be removed at any convenient subsequent stage utilising methods known from the art.

The following Examples illustrate the preparation of compounds according to the invention.

The compounds in accordance with this invention are potent inhibitors when measured in the MLR test described below.

The Mixed Lymphocyte Reaction (MLR) Test

Human peripheral blood mononuclear cells (PBMCs) were isolated from buffy coats, obtained from healthy blood donors by Ficoll (Lymphoprep, Axis-Shield PoC AS, Oslo, Norway) density-gradient centrifugation. The cells at the Ficoll-plasma interface were washed three times and used as "Responder" cells. RPMI 1788 (ATCC, N° CCL-156) cells were treated with mitomycin C (Kyowa, Nycomed, Brussels, Belgium) and used as "Stimulator" cells. Responder cells (0.12×106), Stimulator cells (0.045×106) and compounds (in different concentrations) were cocultured for 6 days in RPMI 1640 medium (BioWhittaker, Lonza, Belgium) supplemented with 10% fetal calf serum, 100 U/ml Geneticin (Gibco, LifeTechnologies, UK). Cells were cultured in triplicate in flat-bottomed 96-well microtiter tissue culture plates (TTP, Switzerland). After 5 days, cells were pulsed with 1 µCi of methyl-$^3$H thymidine (MP Biomedicals, USA), harvested 18 h later on glass filter paper and counted. Proliferation values were expressed as counts per minute (cpm), and converted to % inhibition with respect to a blank MLR test (identical but without added compound). The $IC_{50}$ was determined from a graph with at least four points, each derived from the mean of 2 experiments. The $IC_{50}$ value represents the lowest concentration of test compound (expressed in µM) that resulted in a 50% inhibition of the MLR.

The compounds of the accompanying Examples were all found to generate IC$_{50}$ values in the MLR test of 10 μM or better.

EXAMPLES

| Abbreviations | |
|---|---|
| THF: | tetrahydrofuran |
| MeOH: | methanol |
| EtOH: | ethanol |
| DMSO: | dimethylsulfoxide |
| DIPEA: | N,N-diisopropylethylamine |
| BOP: | (benzotriazol-1-yloxy)tris(dimethylamino)phosphonium hexafluorophosphate |
| PyBOP: | (benzotriazol-1-yloxy)tripyrrolidinophosphonium hexafluorophosphate |
| EDC: | 1-(3-dimethylaminopropyl)-3-ethylcarbodiimide hydrochloride |
| HATU: | O-(7-azabenzotriazol-1-yl)-N,N,N',N'-tetramethyluronium hexafluorophosphate |
| h: | hour |
| MS: | Mass Spectrometry |
| LCMS: | Liquid Chromatography Mass Spectrometry |
| RT: | retention time |
| DMF: | N,N-dimethylformamide |
| DCM: | dichloromethane |
| EtOAc: | ethyl acetate |
| DBU: | 1,8-diazabicyclo[5.4.0]undec-7-ene |
| HOBT: | 1-hydroxybenzotriazole hydrate |
| br: | broad |
| M: | mass |

Intermediate 1

2-Amino-5-(4-fluorophenyl)thieno[2,3-d]pyrimidin-4(1H)-one

A mixture of ethyl 2-amino-4-(4-fluorophenyl)thiophene-3-carboxylate (400 mg, 1.51 mmol), chloroformamidine hydrochloride (434 mg, 3.78 mmol) and dimethylsulfone (710 mg, 7.55 mmol) was heated at 135° C. for 45 minutes. Water was added and the mixture was cooled down to room temperature. An aqueous ammonia solution was added to adjust the solution to pH 9. The precipitate was filtered off, yielding the title compound (440 mg) as a white powder. $\delta_H$ (300 MHz, DMSO-d$_6$) 10.85 (1H, NH, D$_2$O exchangeable), 7.53 (2H, t), 7.17 (2H, t), 6.92 (1H, s), 6.58 (2H, NH$_2$, D$_2$O exchangeable).

Intermediate 2

Ethyl 2-amino-4-(pyridin-3-yl)thiophene-3-carboxylate

To a solution of 3-acetylpyridine (1.762 mL, 16 mmol), ethyl cyanoacetate (2.388 mL, 22.4 mmol) and morpholine (1.690 mL, 19.2 mmol) in ethanol (4.0 mL) and toluene (4.4 mL) was added sulfur (564 mg, 17.6 mmol; finely ground using a mortar). The suspension was heated at 60° C. for 48 hours. The solvents were removed in vacuo and the slurry was dissolved in ethyl acetate. The organic solution was extracted successively with brine, saturated aqueous sodium bicarbonate solution, brine, hydrogen chloride (1N) and again brine. The organic fraction was dried over magnesium sulfate after which the solvent was removed in vacuo. The crude residue was purified by silica gel flash chromatography, the mobile phase being a mixture of heptane and ethyl acetate (in a ratio gradually ranging from 2% to 5% ethyl acetate in heptane), yielding the title compound (1.481 g) as a yellow powder. $^{13}$C NMR δ (75 MHz, CDCl$_3$) 165.07, 164.45, 149.03, 147.41, 137.25, 136.03, 134.10, 121.87, 106.11, 104.87, 61.43, 13.43. MS (m/z) 249 [M+H]$^+$.

Intermediate 3

2-Amino-5-(pyridin-3-yl)thieno[2,3-d]pyrimidin-4(1H)-one

A mixture of Intermediate 2 (1.415 g, 5.7 mmol), chloroformamidine hydrochloride (1.637 g, 14.2 mmol) and dimethylsulfone (2.678 g, 28.5 mmol) was heated at 135° C. for 45 minutes. Water was added and the mixture was cooled down to room temperature. An aqueous ammonia solution was added to adjust the solution to pH 9. The precipitate was filtered off, yielding the title compound (1.364 g) as a yellowish powder. $^{13}$C NMR δ (75 MHz, DMSO-d$_6$) 170.16, 158.39, 153.45, 149.32, 148.01, 136.48, 134.68, 131.67, 122.69, 115.00, 112.24. MS (m/z) 245 [M+H]$^+$.

Intermediate 4

2-Amino-6-methyl-5-phenylthieno[2,3-d]pyrimidin-4(1H)-one

A mixture of ethyl 2-amino-5-methyl-4-phenylthiophene-3-carboxylate (1 g, 3.8 mmol), chloroformamidine hydrochloride (1.1 g, 9.6 mmol) and dimethylsulfone (1.798 g, 19.1 mmol) was heated at 135° C. for 45 minutes. Water was added and the mixture was cooled down to room temperature. An aqueous ammonia solution was added to adjust the solution to pH 9. The precipitate was filtered off, yielding the title compound (920 mg) as a yellowish powder. $^{13}$C NMR δ (75 MHz, DMSO-d$_6$) 166.50, 157.60, 153.02, 135.16, 133.40, 130.30 (2C), 127.35 (2C), 126.79, 124.22, 113.80, 13.33. MS (m/z) 258 [M+H]$^+$.

Intermediate 5

2-[(4-Fluorophenyl)(hydroxy)methylene]malononitrile

To a solution of malononitrile (30 mmol) and triethylamine (36 mmol) in THF/toluene (40 mL, 1:1) at 0° C. was slowly added 4-fluorobenzoyl chloride (30 mmol). The resulting reaction mixture was stirred at room temperature for 2 hours. After concentration under reduced pressure, the crude residue was purified by flash chromatography on silica, the mobile phase being a mixture of methanol and dichloromethane (in a ratio of 1:30), yielding the pure title compound (5.2 g, 93%) as a yellowish oil. MS (m/z) 189.2 [M+H]$^+$ (100%). $\delta_H$ (300 MHz, CDCl$_3$, 25° C.) 10.61 (br s, 1H), 7.80 (dd, J 8.7, 5.4 Hz, 2H), 7.06 (t, J 8.7 Hz, 2H).

Intermediate 6

2-[(Amino)(4-fluorophenyl)methylene]malononitrile

A suspension of Intermediate 5 (20 mmol) in POCl$_3$ (10 mL) was heated at 60° C. for 1 hour. After concentration under reduced pressure, the residue was purified by flash chromatography on silica, the mobile phase being a mixture of acetone and dichloromethane (in a ratio of 1:40), yielding a white solid (3.3 g, 80%). A solution of this material (15 mmol) in 7N NH$_3$ in methanol (10 mL) was stirred at room temperature for 1 hour. After concentration under reduced pressure, the residue was purified by flash chromatography on silica, the mobile phase being a mixture of methanol and dichloromethane (in a ratio of 1:40), yielding the pure title compound (2.52 g, 90%) as a white solid. MS (m/z) 188.2 [M+H]+ (100%). $\delta_H$ (300 MHz, CDCl$_3$, 25° C.) 8.82 (br s, 2H, NH$_2$), 7.67 (dd, J 8.7, 5.3 Hz, 2H), 7.39 (t, J 8.7 Hz, 2H).

Intermediate 7

3-Amino-2-cyano-3-(4-fluorophenyl)prop-2-enethioamide

To a solution of Intermediate 6 (12 mmol) in ethanol (40 mL) and water (10 mL) was added diethyl dithiophosphate (18 mmol). The resulting mixture was heated under reflux for 4 hours. After concentration under reduced pressure, the residue was purified by flash chromatography on silica, the mobile phase being a mixture of methanol and dichloromethane (in a ratio of 1:80), yielding the pure title compound (2.5 g, 94%) as a yellowish solid. MS (m/z) 222.2 [M+H]+ (100%). $\delta_H$ (300 MHz, CDCl$_3$, 25° C.) 11.87 (br s, 1H, NH$_2$), 9.14 (br s, 1H, NH$_2$), 8.84 (br s, 1H, NH$_2$), 7.95 (br s, 1H, NH$_2$), 7.62 (dd, J 8.7, 5.3 Hz, 2H), 7.37 (t, J 8.7 Hz, 2H).

Intermediate 8

5-Amino-3-(4-fluorophenyl)isothiazole-4-carbonitrile

To a solution of Intermediate 7 (10 mmol) in methanol (20 mL) was added H$_2$O$_2$ (20 mmol). The resulting mixture was stirred at room temperature for 3 hours. The solvents were removed under reduced pressure, yielding the pure title compound (2.2 g, >99%) as a white solid. MS (m/z) 210.2 [M+H]+ (100%). $\delta_H$ (300 MHz, CDCl$_3$, 25° C.) 8.17 (br s, 2H, NH$_2$), 7.88 (dd, J 8.4, 5.6 Hz, 2H), 7.35 (t, J 8.7 Hz, 2H).

Intermediate 9

5-Amino-3-(4-fluorophenyl)isothiazole-4-carboxamide

To a concentrated H$_2$SO$_4$ solution (98%; 5 mL) was added Intermediate 8 (10 mmol). The reaction mixture was heated at 60° C. for 2 hours. After cooling down to room temperature, the mixture was poured into ice water (50 mL) and neutralized with an aqueous ammonia solution to pH 6-7. The precipitate was filtered off, washed with water and dried, yielding the pure title compound (2.2 g, 93%) as a white solid. MS (m/z) 238.2 [M+H]+ (100%). $\delta_H$ (300 MHz, DMSO-d$_6$, 25° C.) 7.59 (dd, J 8.4, 5.6 Hz, 2H), 7.26 (t, J 8.7 Hz, 2H).

Intermediate 10

3-(4-Fluorophenyl)isothiazolo[5,4-d]pyrimidin-4-ol

A suspension of Intermediate 9 (1 mmol) in triethyl orthoformate (1 mL) and acetic anhydride (1 mL) was heated at 130° C. for 1 hour. After cooling to room temperature, water (10 mL) was added. The precipitate was filtered off, washed with water and dried, to yield the pure title compound (220 mg, 89%) as a white solid. MS (m/z) 248.2 [M+H]+ (100%).

$\delta_H$ (300 MHz, DMSO-d$_6$, 25° C.) 12.86 (s, 1H, OH), 8.33 (s, 1H), 7.96 (dd, J 8.8, 5.6 Hz, 2H), 7.34 (t, J 8.7 Hz, 2H).

Intermediate 11

6-Amino-3-(4-fluorophenyl)isothiazolo[5,4-d]pyrimidin-4-ol

A mixture of Intermediate 9 (4 mmol) and chloroformamidine hydrochloride (6 mmol) in dimethylsulfone (5 g) was heated at 165° C. for 30 minutes. The reaction was quenched with 2.5N HCl (20 mL) and kept at reflux for 1 hour. The reaction mixture was neutralized with a 25% aqueous ammonia solution to pH 6-7. The precipitate was filtered off, washed with water and dried, yielding the crude product (0.78 g, 75%) which was directly used in the next step without further purification. MS (m/z) 260.2 [M−H]+ (100%).

Intermediate 12

Diethyl 2-aminothiophene-3,4-dicarboxylate

To a solution of ethyl pyruvate (1.778 mL, 16 mmol), ethyl cyanoacetate (2.388 mL, 22.4 mmol) and triethylamine (2.669 mL, 19.2 mmol) in N,N-dimethylformamide (8.0 mL) was added sulfur (564 mg, 17.6 mmol; finely ground using a mortar). The suspension was heated at 60° C. for 5 hours. The solvents were removed in vacuo and the slurry was dissolved in ethyl acetate. The organic solution was extracted successively with brine, saturated aqueous sodium bicarbonate solution, brine, hydrogen chloride (1N) and again brine. The organic fraction was dried over magnesium sulfate after which the solvent was removed in vacuo. The crude residue was purified by silica gel flash chromatography, the mobile phase being a mixture of heptane and ethyl acetate (in a ratio gradually ranging from 20% to 30% ethyl acetate in heptane), yielding the title compound (1.828 g) as a yellow powder. $^{13}$C NMR $\delta$ (75 MHz, CDCl$_3$) 164.78, 164.30, 162.54, 132.57, 110.81, 104.64, 60.87, 59.83, 13.88, 13.84. MS (m/z) 244 [M+H]+.

Intermediate 13

2-Amino-5-(ethoxycarbonyl)thieno[2,3-d]pyrimidin-4(1H)-one

A mixture of Intermediate 12 (1.0 g, 4.1 mmol), chloroformamidine hydrochloride (1.181 g, 10.3 mmol) and dimethylsulfone (1.932 g, 20.5 mmol) was heated at 135° C. for 45 minutes. Water was added and the mixture was cooled down to room temperature.

An aqueous ammonia solution was added to adjust the solution to pH 9. The precipitate was filtered off, yielding the title compound (781 mg) as a white powder. $^{13}$C NMR $\delta$ (75 MHz, CDCl$_3$) 169.24, 163.33, 157.02, 153.90, 129.29, 120.85, 112.43, 60.73, 14.15. MS (m/z) 240 [M+H]+.

Intermediate 14

2-Amino-5-methylthieno[2,3-d]pyrimidin-4(1H)-one

A mixture of ethyl 2-amino-4-methylthiophene-3-carboxylate (2.0 g, 11.7 mmol), chloroformamidine hydrochloride (3.357 g, 29.0 mmol) and dimethylsulfone (5.489 g, 58.4 mmol) was heated at 135° C. for 45 minutes. Water was added and the mixture was cooled down to room temperature. An aqueous ammonia solution was added to adjust the solution to pH 9. The precipitate was filtered off, yielding the title compound (1.863 g) as a white powder. $^{13}$C NMR δ (75 MHz, DMSO-$d_6$) 168.98, 159.12, 153.21, 133.26, 114.37, 110.81, 16.35. MS (m/z) 182 [M+H]$^+$.

Intermediate 15

2-Amino-5-isobutylthieno[2,3-d]pyrimidin-4(1H)-one

Prepared using methyl 2-amino-4-isobutylthiophene-3-carboxylate (1.0 g, 4.7 mmol) applying the procedure described in Intermediate 14. The title compound (1.031 g) was isolated as a white powder. $^{13}$C NMR δ (75 MHz, DMSO-$d_6$) 169.12, 158.79, 153.10, 137.41, 114.02, 111.17, 39.05, 28.15, 22.32 (2C). MS (m/z) 224 [M+H]$^+$.

General Method 1

To a solution of the appropriate acetyl analogue (16 mmol), ethyl cyanoacetate (2.4 mL, 22 mmol) and morpholine (1.7 mL, 19 mmol) in EtOH (4.0 mL) and toluene (4.4 mL) was added sulfur (564 mg, 18 mmol; finely ground using a mortar). The suspension was heated at 60° C. for 48 h. The solvents were removed in vacuo and the slurry was dissolved in EtOAc. The organic solution was extracted successively with brine, saturated sodium bicarbonate, brine, HCl (1N) and again brine. The organic fraction was dried (MgSO$_4$) after which the solvent was removed in vacuo. The crude residue was purified by silica gel flash chromatography, the mobile phase being a mixture of heptane and EtOAc (in a ratio gradually ranging from 2% to 5% EtOAc in heptane), providing the title compound in yields ranging from 29% to 47%.

Intermediate 16

Ethyl 2-amino-4-(3-fluorophenyl)thiophene-3-carboxylate

Prepared via General Method 1 using 1-(3-fluorophenyl) ethanone. $^{13}$C NMR δ (75 MHz, CDCl$_3$) 165.34, 164.31, 161.70 (d, $J_{CF}$ 242.2 Hz), 140.34 (d, $J_{CF}$ 8.3 Hz), 139.85 (d, $J_{CF}$ 2.0 Hz), 128.36 (d, $J_{CF}$ 8.3 Hz), 124.47 (d, $J_{CF}$ 2.5 Hz), 115.82 (d, $J_{CF}$ 21.6 Hz), 113.26 (d, $J_{CF}$ 20.9 Hz), 105.69 (d, $J_{CF}$ 1.8 Hz), 105.00, 59.32, 13.34. MS (m/z) 266 [M+H]$^+$.

Intermediate 17

Ethyl 2-amino-4-(2-fluorophenyl)thiophene-3-carboxylate

Prepared via General Method 1 using 1-(2-fluorophenyl) ethanone. $^{13}$C NMR δ (75 MHz, CDCl$_3$) 165.43, 164.62, 159.93 (d, $J_{CF}$ 243.0 Hz), 130.13 (d, $J_{CF}$ 3.3 Hz), 128.09 (d, $J_{CF}$ 8.0 Hz), 126.59 (d, $J_{CF}$ 15.8 Hz), 122.79 (d, $J_{CF}$ 3.2 Hz), 113.87 (d, $J_{CF}$ 22.2 Hz), 105.52, 58.57, 12.37. MS (m/z) 266 [M+H]$^+$.

General Method 2

A mixture of the appropriate thiophene derivative (3.5 mmol), chloroformamidine hydrochloride (1.0 g, 8.75 mmol) and dimethylsulfone (1.6 g, 17.5 mmol) was heated at 135° C. for 45 minutes. Water was added and the mixture was cooled down to room temperature. An aqueous ammonia solution was added to adjust the solution to pH 9. The precipitate was filtered off, providing the title compound in yields from 87% to 94%.

Intermediate 18

2-Amino-5-(4-methoxyphenyl)thieno[2,3-d]pyrimidin-4(1H)-one

Prepared via General Method 2 using ethyl 2-amino-4-(4-methoxyphenyl)-thiophene-3-carboxylate (commercially available from Acros Organics). $^{13}$C NMR δ (75 MHz, DMSO-$d_6$) 170.16, 158.39, 153.45, 149.32, 148.01, 136.48, 134.68, 131.67, 122.69, 115.00, 112.24. MS (m/z) 245 [M+H]$^+$.

Intermediate 19

2-Amino-5-(4-chlorophenyl)thieno[2,3-d]pyrimidin-4(1H)-one

Prepared via General Method 2 using ethyl 2-amino-4-(4-chlorophenyl)thiophene-3-carboxylate (commercially available from Acros Organics). $^{13}$C NMR δ (75 MHz, DMSO-$d_6$) 170.08, 158.24, 153.37, 136.93, 134.79, 131.93, 130.92 (2C), 127.51 (2C), 114.35. MS (m/z) 278 [M+H]$^+$.

Intermediate 20

2-Amino-5-(3-fluorophenyl)thieno[2,3-d]pyrimidin-4(1H)-one

Prepared via General Method 2 using Intermediate 16. $^{13}$C NMR δ (75 MHz, DMSO-$d_6$) 170.15, 161.60 (d, $J_{CF}$ 240.2 Hz), 158.24, 153.37, 138.18 (d, $J_{CF}$ 8.4 Hz), 136.88, 129.35 (d, $J_{CF}$ 8.2 Hz), 125.12, 116.10 (d, $J_{CF}$ 21.9 Hz), 114.82, 113.86 (d, $J_{CF}$ 20.3 Hz), 112.18. MS (m/z) 262 [M+H]$^+$.

Intermediate 21

2-Amino-5-(2-fluorophenyl)thieno[2,3-d]pyrimidin-4(1H)-one

Prepared via General Method 2 using Intermediate 17. $^{13}$C NMR δ (75 MHz, DMSO-$d_6$) 168.89, 159.82 (d, $J_{CF}$ 244.0 Hz), 157.91, 153.47, 131.56, 131.07, 129.44 (d, $J_{CF}$ 8.2 Hz), 124.43 (d, $J_{CF}$ 15.5 Hz), 123.72, 115.23, 115.03 (d, $J_{CF}$ 12.7 Hz), 113.68. MS (m/z) 262 [M+H]$^+$.

Intermediate 22

2-Amino-5-(4-fluorophenyl)-6-methylthieno[2,3-d] pyrimidin-4(1H)-one

Prepared via General Method 2 using ethyl 2-amino-4-(4-fluorophenyl)-5-methylthiophene-3-carboxylate (commercially available from Enamine Ltd.). $^{13}$C NMR δ (75 MHz, DMSO-$d_6$) 166.50, 163.34 (d, $J_{CF}$ 241.5 Hz), 157.69, 152.98, 132.24, 123.23 (2C, d, $J_{CF}$ 7.5 Hz), 131.36 (d, $J_{CF}$ 3.7 Hz), 124.51, 114.17 (2C, d, $J_{CF}$ 21.1 Hz), 113.71, 13.26. MS (m/z) 276 [M+H]$^+$.

Intermediate 23

2-Amino-5-cyclohexylthieno[2,3-d]pyrimidin-4 (1H)-one

Prepared via General Method 2 using ethyl 2-amino-4-cyclohexylthiophene-3-carboxylate (commercially available from Enamine Ltd.). $^{13}$C NMR δ (75 MHz, DMSO-$d_6$) 169.1 (C-4), 158.5 (C-2), 152.8 (C-7a), 144.4 (C-5), 113.4 (C-4a), 108.2 (C-6), 38.1 (CH), 33.1 (CH$_2$), 26.4 (CH$_2$), 25.9 (CH$_2$). δ$_H$ (300 MHz, DMSO-d$_6$) 1.26-1.94 (m, 11H, CH), 6.47 (s, 2H, NH$_2$), 6.51 (s, 1H, H-6). MS (m/z) 250 [M+H]$^+$.

Intermediate 24

2-Amino-5-(3-chloropropyl)thieno[2,3-d]pyrimidin-4(1H)-one

Prepared via General Method 2 using ethyl 2-amino-4-cyclopropylthiophene-3-carboxylate (commercially available from Enamine Ltd.). $^{13}$C NMR δ (75 MHz, DMSO-d$_6$) 169.3 (C-4), 158.7 (C-2), 153.1 (C-7a), 136.5 (C-5), 113.6 (C-4a), 111.0 (C-6), 44.9 (CH$_2$Cl), 32.1 (CH$_2$), 27.4 (CH$_2$). δ$_H$ (300 MHz, DMSO-d$_6$) 1.99-2.08 (m, 2H, CH$_2$), 2.84 (t, J 7.5 Hz, 2H, CH$_2$), 3.59 (t, J 6.6 Hz, 2H, CH$_2$Cl), 6.51 (s, 2H, NH$_2$), 6.59 (s, 1H, H-6). MS (m/z) 244 [M+H]$^+$.

Intermediate 25

2-Aminothieno[2,3-d]pyrimidin-4(1H)-one

Prepared via General Method 2 using ethyl 2-aminothiophene-3-carboxylate (commercially available from Enamine Ltd.). $^{13}$C NMR δ (75 MHz, DMSO-d$_6$) 168.40, 158.38, 153.33, 121.40, 116.39, 115.78. MS (m/z) 168 [M+H]$^+$.

General Method 3

To a solution of the appropriate thieno[2,3-d]pyrimidin-4(1H)-one derivative (1.8 mmol) in acetonitrile (20 mL) were added DBU (403 μL, 2.70 mmol), BOP (1.0 g, 2.34 mmol) and piperazine (310 mg, 3.60 mmol). The reaction mixture was stirred overnight at room temperature. The solvents were evaporated in vacuo and the crude residue was purified by flash chromatography, the mobile phase being a mixture of MeOH/DCM (in a ratio gradually increasing from 3% to 4% MeOH in DCM with 0.5% aqueous ammonia solution), providing the title compound in yields from 67% to 88%.

Intermediate 26

2-Amino-5-(4-methoxyphenyl)-4-(piperazin-1-yl)thieno[2,3-d]pyrimidine

Prepared via General Method 3 using Intermediate 18. $^{13}$C NMR δ (75 MHz, CD$_3$OD) 172.18, 162.60, 159.64, 158.66, 135.56, 129.50, 129.28 (2C), 113.95, 113.79 (2C), 108.45, 55.33, 50.20 (2C), 44.33 (2C). MS (m/z) 342 [M+H]$^+$.

Intermediate 27

2-Amino-5-(4-chlorophenyl)-4-(piperazin-1-yl)thieno[2,3-d]pyrimidine

Prepared via General Method 3 using Intermediate 19. MS (m/z) 346 [M+H]$^+$.

Intermediate 28

2-Amino-5-(3-fluorophenyl)-4-(piperazin-1-yl)thieno[2,3-d]pyrimidine

Prepared via General Method 3 using Intermediate 20. MS (m/z) 330 [M+H]$^+$.

Intermediate 29

2-Amino-5-(2-fluorophenyl)-4-(piperazin-1-yl)thieno[2,3-d]pyrimidine

Prepared via General Method 3 using Intermediate 21. $^{13}$C NMR δ (75 MHz, CDCl$_3$+CD$_3$OD) 171.8 (C-4), 164.4 (C-2), 160.4 (C-7a), 159.0 (d, J$_{CF}$ 245.9 Hz, phenyl), 131.9 (d, J$_{CF}$ 2.7 Hz, phenyl), 130.2 (d, J$_{CF}$ 8.0 Hz, phenyl), 129.7 (C-5), 125.5 (d, J$_{CF}$ 14.9 Hz, phenyl), 124.9 (d, J$_{CF}$ 3.4 Hz, phenyl), 118.1 (C-6), 116.4 (d, J$_{CF}$ 21.9 Hz, phenyl), 111.6 (C-4a), 51.0 (NCH$_2$), 44.9 (NCH$_2$). δ$_H$ (300 MHz, CDCl$_3$+CD$_3$OD) 2.36 (m, 4H, NCH$_2$), 3.09 (m, 4H, NCH$_2$), 6.95 (s, 1H, H-6), 7.15-7.68 (m, 4H, phenyl). MS (m/z) 330 [M+H]$^+$.

Intermediate 30

2-Amino-5-(4-fluorophenyl)-6-methyl-4-(piperazin-1-yl)thieno[2,3-d]pyrimidine

Prepared via General Method 3 using Intermediate 22. $^{13}$C NMR δ (75 MHz, CDCl$_3$+CD$_3$OD) 169.3 (C-4), 161.9 (C-2), 159.5 (d, J$_{CF}$ 242.3 Hz, phenyl), 159.2 (C-7a), 131.9 (d, J$_{CF}$ 7.9 Hz, phenyl), 131.6 (C-5), 129.4 (phenyl), 129.7 (phenyl), 118.1 (C-6), 114.5 (d, J$_{CF}$ 21.2 Hz, phenyl), 110.1 (C-4a), 49.4 (NCH$_2$), 43.5 (NCH$_2$), 13.9 (CH$_3$). δ$_H$ (300 MHz, CDCl$_3$+CD$_3$OD) 2.31 (m, 7H, (NCH$_2$, 4H), (CH$_3$, 3H)), 3.01 (m, 4H, NCH$_2$), 7.16-7.34 (m, 4H, phenyl). MS (m/z) 344 [M+H]$^+$.

Intermediate 31

2-Amino-5-cyclohexyl-4-(piperazin-1-yl)thieno[2,3-d]pyrimidine

Prepared via General Method 3 using Intermediate 23. $^{13}$C NMR δ (75 MHz, DMSO-d$_6$) 171.4 (C-4), 164.8 (C-2), 161.2 (C-7a), 140.9 (C-5), 112.6 (C-4a), 111.9 (C-6), 50.9 (NCH$_2$), 44.8 (NCH$_2$), 38.2 (CH), 34.5 (CH$_2$), 26.7 (CH$_2$), 25.9 (CH$_2$). δ$_H$ (300 MHz, DMSO-d$_6$) 1.26-1.99 (m, 11H, CH), 3.06 (m, 4H, NCH$_2$), 3.31 (NCH$_2$), 6.66 (s, 1H, H-6). MS (m/z) 318 [M+H]$^+$.

Intermediate 32

2-Amino-5-(3-chloropropyl)-4-(piperazin-1-yl)thieno[2,3-d]pyrimidine

Prepared via General Method 3 using Intermediate 24. $^{13}$C NMR δ (75 MHz, CDCl$_3$+CD$_3$OD) 171.9 (C-4), 164.3 (C-2), 158.8 (C-7a), 132.8 (C-5), 114.1 (C-6), 112.9 (C-4a), 50.1 (NCH$_2$), 44.2 (CH$_2$Cl), 32.5 (CH$_2$), 27.6 (CH$_2$). MS (m/z) 312 [M+H]$^+$.

Intermediate 33

2-Amino-4-(piperazin-1-yl)thieno[2,3-d]pyrimidine

Prepared via General Method 3 using Intermediate 25. MS (m/z) 308 [M+H]$^+$.

Intermediate 34

Ethyl 2-amino-4-[4-(tert-butoxycarbonyl)piperazin-1-yl]thieno[2,3-d]pyrimidine-5-carboxylate To a solution of Intermediate 13 (700 mg, 2.90 mmol) in acetonitrile (30 mL) were added DBU (656 μL, 4.40 mmol), BOP (1.68 g, 3.80 mmol) and tert-butyl piperazine-1-carboxylate (503 mg, 58.5 mmol). The reaction mixture was stirred overnight at room temperature. The solvents were evaporated in vacuo and the crude residue was purified by flash chromatography, the mobile phase being a mixture of MeOH and DCM (in a ratio gradually increasing from 3% to 5% MeOH in DCM with 0.5% aqueous ammonia solution), yielding the title compound (461 mg) as a white solid. $^{13}$C NMR δ (75 MHz, CDCl$_3$) 172.5 (C-4), 162.9 (C-2), 161.1 (C-7a), 159.3 (C=O), 154.9 (C=O), 127.7 (C-5), 125.8 (C-6), 107.8 (C-4a), 80.1 (OC(CH$_3$)$_3$), 61.4 (OCH$_2$), 48.4 (NCH$_2$), 43.8 (NCH$_2$), 28.5 (CH$_3$), 14.4 (CH$_3$). MS (m/z) 408 [M+H]$^+$.

Intermediate 35

2-Amino-4-[4-(tert-butoxycarbonyl)piperazin-1-yl]thieno[2,3-d]pyrimidine-5-carboxylic acid To a solution of Intermediate 34 (1 g, 2.45 mmol) in MeOH (30 mL) and water (3 mL) was added aqueous sodium hydroxide solution (14.7N, 840 μL, 12.3 mmol). The reaction mixture was stirred under reflux for 3 hours. After cooling the reaction mixture, concentrated HCl was added until pH 4-5 was reached. The precipitate was filtered off and dried, yielding the title compound (846 mg) as a white powder. MS (m/z) 380 [M+H]$^+$.

Intermediate 36 tert-Butyl 4-[2-amino-5-(hydroxymethyl)thieno[2,3-d]pyrimidin-4-yl]piperazine-1-carboxylate To a solution of Intermediate 35 (100 mg, 0.26 mmol) in THF (4 mL) were added triethylamine (44 μL, 0.32 mmol) and ethyl chloroformate (26 μL, 0.28 mmol). The reaction mixture was stirred at room temperature for one hour, after which time the reaction mixture was extracted using saturated aqueous sodium bicarbonate solution and DCM, and the organic layer was dried (MgSO$_4$). The solvents were evaporated in vacuo and the residue was dissolved in THF (4 mL). To the resulting solution, sodium borohydride (4 eq.) was added, followed by methanol (1 mL) dropwise. The reaction mixture was extracted using aqueous sodium bicarbonate solution and DCM. The solvents were evaporated in vacuo and the crude residue was purified by flash chromatography, the mobile phase being a mixture of MeOH and DCM (in a ratio gradually increasing from 3% to 5% MeOH in DCM), yielding the title compound (105 mg). MS (m/z) 366 [M+H]$^+$.

Intermediate 37 tert-Butyl 4-[2-amino-5-(ethoxycarbonylamino)thieno[2,3-d]pyrimidin-4-yl]piperazine-1-carboxylate To a solution of Intermediate 35 (100 mg, 0.26 mmol) in DMF (4 mL) were added triethylamine (74 μL, 0.52 mmol) and diphenyl phosphoryl azide (60 μL, 0.28 mmol). The reaction mixture was stirred at r.t. for 20 h. Ethanol (4 mL) was added and the reaction mixture was heated by microwave irradiation (150° C., 150 W) for one hour. The solvents were evaporated in vacuo and the crude residue was purified by flash chromatography, the mobile phase being a mixture of MeOH and DCM (in a ratio gradually increasing from 3% to 5% MeOH in DCM), yielding the title compound (61 mg). MS (m/z) 423 [M+H]$^+$.

Intermediate 38

2-Amino-4-[4-(4-methoxy-2-methylphenylcarbamoyl)piperazin-1-yl]thieno[2,3-d]-pyrimidine-5-carboxylic acid To a solution of Example 77 (3 g, 6.4 mmol) in EtOH/THF (1:1, 30 mL) was added 2M aqueous NaOH solution (30 mL). The reaction mixture was heated at 60° C. for 2.5 h before being cooled and concentrated in vacuo. To the residue was added water (20 mL), then concentrated HCl was added dropwise at 0° C. until a pH of 6 was reached and a white solid precipitated. The solid was filtered and dried on a sinter to give the title compound (2 g). MS (m/z) 433 [M+H]$^+$.

Intermediate 39

2-Amino-4-hydroxy-4-(trifluoromethyl)-4,5-dihydrothiophene-3-carboxylic acid methyl ester Aqueous NaOH solution (1M, 20 mL) was added slowly to a solution of sodium hydrogensulphide hydrate (4.1 g, 73 mmol) in water (16 mL) at 0° C. The reaction mixture was degassed and flushed with nitrogen before the addition of 1-bromo-3,3,3-trifluoroacetone (10 g, 52 mmol). After stirring at 0° C. for 50 minutes, methyl cyanoacetate (3.8 mL, 54 mmol) was added, followed by triethylamine (7.6 mL, 54 mmol), and the reaction mixture was allowed to warm to room temperature. The reaction mixture was then diluted with EtOAc and separated. The aqueous layer was washed with EtOAc and the combined organic layers were washed with brine, dried (MgSO$_4$) and concentrated in vacuo to afford a brown solid. Recrystallisation from EtOAc/hexane gave the title compound (4.1 g) as a brown solid. LCMS (pH 10) RT 1.08 minutes; MS (m/z) 245 [M+H]$^+$.

Intermediate 40

2-Amino-4-(trifluoromethyl)thiophene-3-carboxylic acid methyl ester

Intermediate 39 (4 g) was heated to 175° C. until melted and stirred for 10 minutes before cooling. EtOAc was added and the organics were washed with brine, dried (MgSO$_4$) and concentrated in vacuo to give the title compound (4 g) as a brown solid. δ$_H$ (400 MHz, DMSO-d$_6$) 7.65 (2H, s), 7.04 (1H, s), 3.73 (3H, s).

Intermediate 41

2-Amino-5-(trifluoromethyl)thieno[2,3-d]pyrimidin-4-ol

HCl (4M in 1,4-dioxane, 15 mL, 60 mmol) was added slowly to a solution of cyanamide (1.9 g, 45 mmol) in 1,4-dioxane (20 mL). The reaction mixture was stirred for 2.5 h and then concentrated in vacuo. The resulting white powder was then heated to 165° C. with a solution of Intermediate 40 (4 g, 18 mmol) in diglyme (37 mL) for 10 minutes before cooling to room temperature. The resulting brown solid was filtered and dissolved in aqueous NaOH solution (10%, 40 mL), then heated to 70° C. until completely dissolved. After cooling to 0° C., the solution was acidified to pH 2.5 (conc. HCl) and, in the absence of a precipitate, the solution was neutralized and concentrated in vacuo. The solids were then suspended in warm DCM/MeOH and filtered. The filtrate was concentrated in vacuo to give the title compound (2.5 g) as a brown solid. LCMS (pH 10) RT 0.32 minutes; MS (m/z) 234 [M−H]+.

Intermediate 42

General Method 4

4-[2-Amino-5-(trifluoromethyl)thieno[2,3-d]pyrimidin-4-yl]piperazine-1-carboxylic acid tert-butyl ester DBU (2.4 mL, 16 mmol) was added to a suspension of Intermediate 41 (2.5 g, 11 mmol) and PyBOP (7.4 g, 14 mmol) in acetonitrile (75 mL). The mixture was stirred for 10 minutes, then tert-butyl piperazine-1-carboxylate (3 g, 16 mmol) was added and the reaction mixture was heated at 60° C. for 12 h. The reaction mixture was then cooled to room temperature and concentrated in vacuo. The residue was partitioned between EtOAc and water, then separated. The organics were washed with citric acid (1M) and aqueous NaHCO$_3$ solution, dried (MgSO$_4$) and concentrated in vacuo. The crude residue was purified by column chromatography, eluting with 20-70% EtOAc/hexanes, to give the title compound (328 mg) as a cream solid. $\delta_H$ (400 MHz, DMSO-d$_6$) 7.98 (1H, s), 6.82 (2H, s), 3.44-3.43 (4H, m), 3.31-3.29 (4H, m), 1.43 (9H, s).

Intermediate 43

General Method 5

4-(piperazin-1-yl)-5-(trifluoromethyl)thieno[2,3-d]pyrimidin-2-ylamine

To Intermediate 42 (328 mg) was added HCl (4M in 1,4-dioxane, 5 mL) and the reaction mixture was stirred for 5 h. The reaction mixture was then concentrated in vacuo to give the title compound (496 mg) as a white powder. $\delta_H$ (400 MHz, DMSO-d$_6$) 9.32 (2H, s), 8.04 (1H, s), 3.45-3.40 (4H, m), 3.15 (4H, m).

Intermediate 44

General Method 6

2-Amino-4-[4-(tert-butoxycarbonyl)piperazin-1-yl]-6-chloropyrimidine-5-carboxaldehyde To a suspension of 2-amino-4,6-dichloropyrimidine-5-carboxaldehyde (3.84 g, 20 mmol) and DIPEA (5.2 mL, 30 mmol) in DMF was added tert-butyl piperazine-1-carboxylate (3.73 g, 20 mmol) portionwise. The reaction mixture was stirred at room temperature overnight. The reaction mixture was concentrated and the residue obtained was precipitated with H$_2$O. The precipitate was collected, washed with water and dried in vacuo, to provide the title compound as a white solid in quantitative yield. MS (m/z) 342 [M+H]+.

Intermediate 45

2-Amino-4-[4-(tert-butoxycarbonyl)-2-(S)-methylpiperazin-1-yl]-6-chloropyrimidine-5-carboxaldehyde The title compound (645 mg) was isolated as a white solid via General Method 6 from 2-amino-4,6-dichloropyrimidine-5-carboxaldehyde (384 mg, 2 mmol), tert-butyl 3-(S)-methylpiperazine-1-carboxylate (400 mg, 2 mmol) and DIPEA (0.68 mL, 4 mmol). MS (m/z) 356 [M+H]+.

Intermediate 46

General Method 7

2-Amino-4-[4-(tert-butoxycarbonyl)piperazin-1-yl] isothiazolo[5,4-d]pyrimidine

A suspension of Intermediate 44 (3.42 g, 10 mmol) and sulfur (320 mg, 10 mmol) in a mixture of concentrated aqueous ammonium hydroxide solution (20 mL) and DMF (35 mL) was heated at 90° C. in a sealed tube for 24 h. The reaction mixture was diluted with water (40 mL) and stored at ice-bath temperature for 4 h. The precipitate was collected, washed with water and dried in vacuo, to provide the title compound (1.71 g, 5.08 mmol) as a pale solid. MS (m/z) 337 [M+H]+.

Intermediate 47

2-Amino-4-[4-(tert-butoxycarbonyl)-2-(S)-methylpiperazin-1-yl]isothiazolo[5,4-d]-pyrimidine The title compound (172 mg) was isolated as a white solid via General Method 7 from Intermediate 45 (356 mg, 1 mmol). MS (m/z) 351 [M+H]+.

Intermediate 48

General Method 8

2-Amino-4-(piperazin-1-yl)isothiazolo[5,4-d]pyrimidine

Intermediate 46 (130 mg, 0.38 mmol) was dissolved in a mixture of trifluoroacetic acid (3 mL) and DCM (3 mL). The reaction mixture was stirred at room temperature for 2 h until the starting material was completely consumed. The reaction mixture was evaporated to dryness, and co-evaporated with ammonia in methanol, to provide the title compound (92 mg, quantitative) as a white solid. MS (m/z) 237 [M+H]+.

Intermediate 49

2-Amino-4-(2-(S)-methylpiperazin-1-yl)isothiazolo[5,4-d]pyrimidine

The title compound (118 mg) was prepared via General Method 8 using Intermediate 47 (165 mg, 0.47 mmol). MS (m/z) 251 [M+H]+.

Intermediate 50

4-(2-Amino-5-carbamoylthieno[2,3-d]pyrimidin-4-yl)piperazine-1-carboxylic acid tert-butyl ester Intermediate 35 (1 g, 2.6 mmol) was stirred with ammonium chloride (0.7 g, 13.2 mmol), HOBT (0.4 g, 2.9 mmol), EDC (0.6 g, 2.9 mmol) and diisopropylamine (4.5 mL, 26 mmol) in DMF (30 mL) for 12 hours. On completion, the reaction mixture was concentrated in vacuo, diluted with EtOAc and washed with brine. The organics were dried (MgSO$_4$) and concentrated in vacuo, to give the title compound (780 mg) as a white solid. MS (m/z) 379 [M+H]+.

Intermediate 51

4-(2-Amino-5-cyanothieno[2,3-c]pyrimidin-4-yl)piperazine-1-carboxylic acid tert-butyl ester To Intermediate 50 (200 mg, 0.53 mmol), stirring in DMF (5 mL) at 0° C., was added cyanuric trichloride (146 mg in 3 mL DMF, 0.80 mmol) dropwise. The reaction mixture was stirred at 0° C. for 30 minutes, then allowed to warm to room temperature and stirred for 12 h. Water (10 mL) was then added and the reaction mixture was stirred at room temperature for a further 24 h. The precipitated white solid was filtered, washed with Et$_2$O and dried on a sinter, to give the title compound (90 mg) as a white powder. MS (m/z) 361 [M+H]$^+$.

Intermediate 52

2-Amino-4-(piperazin-1-yl)thieno[2,3-d]pyrimidine-5-carbonitrile

The title compound (45 mg) was prepared as a white solid via General Method 5 using Intermediate 51 (90 mg) in MeOH (2 mL) and HCl (4M in 1,4-dioxane, 5 mL). MS (m/z) 261 [M+H]$^+$.

Intermediate 53

4-(2-Amino-5-oxo-5,6-dihydrothieno[2,3-d]pyrimidin-4-yl)piperazine-1-carboxylic acid tert-butyl ester To Intermediate 35 (0.5 g, 1.3 mmol) stirring in THF (10 mL) were added diphenyl phosphoryl azide (336 μL, 1.5 mmol) and triethylamine (208 uL, 1.5 mmol). The reaction mixture was stirred overnight and concentrated in vacuo, then water (4 mL) was added. The reaction mixture was then heated under microwave irridation at 125° C. for 25 minutes. After cooling, EtOAc was added. The organics were washed with brine, dried (MgSO$_4$) and concentrated in vacuo. The crude material was purified by column chromatography, eluting with 35% EtOAc/hexanes, to give the title compound (230 mg) as a white solid. LCMS (pH 10) RT 1.20 minutes; MS (m/z) 352 [M+H]$^+$.

Intermediate 54

2-Amino-4-(piperazin-1-yl)thieno[2,3-d]pyrimidin-5-one

The title compound (180 mg) was prepared as a white solid via General Method 5 using Intermediate 53 (230 mg). LCMS (pH 10) RT 0.95 minutes; MS (m/z) 252 [M+H]$^+$.

Intermediate 55

Ethyl 2-amino-4-[4-(tert-butoxycarbonyl)-2-methylpiperazin-1-yl]thieno[2,3-d]-pyrimidine-5-carboxylate To a stirred solution of Intermediate 13 (0.2 g) in acetonitrile (5 mL) at r.t. were added PyBop (0.460 g, 1.3 eq.) and DBU (0.155 g, 1.5 eq.). The mixture was stirred for 15 minutes. tert-Butyl 3-methylpiperazine-1-carboxylate (0.1 g, 1.5 eq.) was then added, and the reaction mixture was heated at 60° C. for 3 h. The reaction mixture was concentrated, then extracted with ethyl acetate and water. The organic layer was evaporated and the residue was purified by column chromatography (60% EtOAc in hexane) to give the title compound (0.175 g, 61%).

Intermediate 56

2-Amino-4-[4-(tert-butoxycarbonyl)-2-methylpiperazin-1-yl]thieno[2,3-d]pyrimidine-5-carboxylic acid To a stirred solution of Intermediate 55 in THF/EtOH (5 mL) was added 2N aqueous NaOH solution (0.2 mL). The reaction mixture was heated at 80° C. for 4 h. The reaction mixture was then concentrated, acidified with 1N HCl and extracted with ethyl acetate to obtain the title compound (0.013 g, 82%).

Intermediate 57 tert-Butyl 4-(2-amino-5-carbamoylthieno[2,3-d]pyrimidin-4-yl)-3-methylpiperazine-1-carboxylate To a stirred solution of Intermediate 56 (0.1 g) in DMF (2 mL) were added HOBT (0.037 g, 1.1 eq.) and EDC (0.053 g, 1.1 eq.). The mixture was stirred for 10 minutes at 0° C. DIPEA (0.42 mL, 10 eq.) and NH$_4$Cl (0.068 g, 5 eq.) were then added. The reaction mixture was stirred at r.t. overnight. The reaction mixture was then extracted with ethyl acetate and water. The organic layer was evaporated and the crude residue was purified by column chromatography (5% MeOH in DCM) to give the title compound (0.055 g, 55%).

Intermediate 58 tert-Butyl 4-(2-amino-5-cyanothieno[2,3-d]pyrimidin-4-yl)-3-methylpiperazine-1-carboxylate To a stirred solution of Intermediate 57 (0.2 g) in THF (10 mL) at 0° C. were added triethylamine (0.21 mL, 3 eq.) and POCl$_3$ (0.073 mL, 1.5 eq.). The reaction mixture was stirred at r.t. for 2 h. The reaction mixture was then basified with saturated aqueous NaHCO$_3$ solution and extracted with ethyl acetate, to give the title compound (0.125 g, 65%).

Intermediate 59

2-Amino-4-(2-methylpiperazin-1-yl)thieno[2,3-d]pyrimidine-5-carbonitrile

To Intermediate 58 (0.120 g) at 0° C. was added HCl in 1,4-dioxane (1.5 mL). The mixture was stirred at r.t. for 2 h. The solvent was then evaporated under reduced pressure to afford the title compound (0.1 g) as a crude solid.

Intermediate 60

(Ethanimidoylamino) 2-amino-4-{4-[(4-methoxyphenyl)carbamoyl]piperazin-1-yl}-thieno[2,3-d]pyrimidine-5-carboxylate To a solution of Example 26 (200 mg, 0.46 mmol) in DMF (3 mL) were added HATU (260 mg, 0.7 mmol) and DIPEA (0.180 mL, 1.4 mmol) at 0° C. The reaction mixture was stirred at 0° C. for 20 minutes. To the reaction mixture was then added N'-hydroxyacetamidine (1.1 eq.), and the reaction mixture was stirred at room temperature for 16 h. The reaction mixture was then quenched with water and extracted with ethyl acetate. The organic layer was washed with saturated aqueous NaHCO₃ solution, then brine. The organic layer was separated, dried and concentrated. The crude residue was purified by column chromatography (silica 100:200, MeOH:DCM) to afford the title compound (95 mg, 42.2%). $\delta_H$ (400 MHz, DMSO-d₆) 8.42 (s, 1H), 7.89 (s, 1H), 7.32 (s, 2H), 6.81 (s, 2H), 6.51 (s, 4H), 3.70 (s, 3H), 3.45 (d, J 10.0 Hz, 8H), 1.81 (s, 3H). LCMS: MH⁺ 485.05, RT 1.65 minutes.

Intermediate 61

(2-Methylpropanimidoylamino) 2-amino-4-{4-[(4-methoxyphenyl)carbamoyl]piperazin-1-yl}thieno[2,3-d]pyrimidine-5-carboxylate The title compound (100 mg, 41.8%) was prepared by the procedure described for Intermediate 60, using N'-hydroxy-2-methylpriopanamidine. $\delta_H$ (400 MHz, DMSO-d₆) 8.40 (s, 1H), 7.84 (s, 1H), 7.31 (d, J 8.9 Hz, 2H), 6.81 (d, 2H), 6.50 (m, 4H), 3.70 (s, 3H), 3.50-3.37 (m, 9H), 1.12 (d, J 7.0 Hz, 6H). LCMS: MH⁺ 513.1, RT 1.65 minutes.

Intermediate 62

(2,2-Dimethylpropanimidoylamino) 2-amino-4-{4-[(4-methoxyphenyl)carbamoyl]-piperazin-1-yl}thieno[2,3-d]pyrimidine-5-carboxylate The title compound (120 mg, 48.0%) was prepared by the procedure described for Intermediate 60, using N'-hydroxy-2,2-dimethylpriopanamidine. $\delta_H$ (400 MHz, DMSO-d₆) 8.39 (s, 1H), 7.82 (s, 1H), 7.36-7.26 (m, 2H), 6.86-6.77 (m, 2H), 6.51 (s, 2H), 6.20 (s, 2H), 3.70 (s, 3H), 3.54-3.44 (m, 4H), 3.43-3.36 (m, 4H), 1.16 (s, 9H). LCMS: MH⁺ 527.15, RT 1.85 minutes.

Preparative Example 1

2-Amino-5-(4-fluorophenyl)-4-(piperazin-1-yl)thieno[2,3-d]pyrimidine

To a solution of Intermediate 1 (440 mg, 1.68 mmol) in acetonitrile (20 mL) were added DBU (376 μL, 2.52 mmol), BOP (966 mg, 2.18 mmol) and piperazine (289 mg, 3.36 mmol). The reaction mixture was stirred overnight at room temperature. The solvents were evaporated in vacuo and the crude residue was purified by flash chromatography, the mobile phase being a mixture of methanol and dichloromethane (in a ratio gradually increasing from 3% to 4% methanol in dichloromethane with 0.5% aqueous ammonia solution), yielding the title compound (437 mg) as a white powder. ¹³C NMR δ (75 MHz, CD₃OD) 172.22, 162.66, 161.59 (d, $J_{CF}$ 242.2 Hz), 159.77, 134.65, 133.29, 130.13 (2C, d, $J_{CF}$ 8.0 Hz), 115.27, 115.08 (2C, d, $J_{CF}$ 12.1 Hz), 108.37, 50.21 (2C), 44.24 (2C).

Example 2

1-{4-[2-amino-5-(4-fluorophenyl)thieno[2,3-d]pyrimidin-4-yl]piperazin-1-yl}-2-(4-chlorophenoxy)ethanone To a solution of Example 1 (135 mg, 0.41 mmol) in 1,4-dioxane (15 mL) were added N,N-diisopropylethylamine (169 μL, 1.02 mmol) and 4-chlorophenoxyacetyl chloride (0.45 mmol). The reaction mixture was stirred at room temperature overnight. The reaction mixture was diluted with dichloromethane and the organic layer was extracted several times with water. The combined organic layers were evaporated in vacuo and the crude residue was purified by silica gel flash chromatography, the mobile phase being a mixture of methanol and dichloromethane (in a ratio gradually ranging from 0.5% to 1% methanol in dichloromethane), yielding the title compound as a white powder. MS (m/z) 498 [M+H]⁺.

Example 3

{4-[2-Amino-5-(4-fluorophenyl)thieno[2,3-d]pyrimidin-4-yl]piperazin-1-yl}-(cyclopropyl)methanone Prepared by the procedure described in Example 2, using cyclopropanecarbonyl chloride. $\delta_H$ (300 MHz, CDCl₃) 7.39-7.44 (2H, m), 7.08-7.14 (2H, m), 6.81 (1H, s), 5.02 (2H, br s, NH₂), 3.22 (8H, t), 1.61 (1H, m), 0.73 (2H, m), 0.71 (2H, m).

Example 4

4-[2-Amino-5-(4-fluorophenyl)thieno[2,3-d]pyrimidin-4-yl]-N-(m-tolyl)piperazine-1-carboxamide To a solution of Example 1 (115 mg, 0.35 mmol) in 1,4-dioxane (15 mL) was added m-tolyl isocyanate (0.38 mmol). The reaction mixture was stirred overnight. The reaction mixture was diluted with dichloromethane and the organic layer was extracted several times with water. The combined organic layers were evaporated in vacuo and the crude residue was purified by silica gel flash chromatography, the mobile phase being a mixture of methanol and dichloromethane (in a ratio gradually ranging from 0.5% to 1% methanol in dichloromethane), yielding the title compound as a white powder. MS (m/z) 463 [M+H]⁺.

Example 5

4-[2-Amino-5-(4-fluorophenyl)thieno[2,3-d]pyrimidin-4-yl]-N-(4-methoxyphenyl)-piperazine-1-carboxamide Prepared by the procedure described in Example 4, using 4-methoxyphenyl isocyanate. $\delta_H$ (300 MHz, CDCl₃) 7.43 (2H, m), 7.11-7.21 (4H, m), 6.82 (1H, t), 6.12 (1H, br s, NH), 4.93 (2H, br s, NH₂), 3.79 (3H, s), 3.18 (4H, br s), 3.12 (4H, br s).

Example 6

4-[2-Amino-5-(4-fluorophenyl)thieno[2,3-d]pyrimidin-4-yl]-N-(4-isopropylphenyl)-piperazine-1-carboxamide Prepared by the procedure described in Example 4, using 4-isopropylphenyl isocyanate. $\delta_H$ (300 MHz, CDCl₃) 7.44-7.46 (2H, m), 7.14-7.19 (6H, m), 6.18 (1H, s, NH), 4.93 (2H, br s, NH₂), 3.18 (4H, t), 3.15 (4H, t), 2.86 (1H, septet), 1.23 (6H, d).

Example 7

4-[2-Amino-5-(4-fluorophenyl)thieno[2,3-d]pyrimidin-4-yl]-N-(4-cyanophenyl)-piperazine-1-carboxamide Prepared by the procedure described in Example 4, using 4-cyanophenyl isocyanate. $\delta_H$ (300 MHz, DMSO-d₆) 8.92

(1H, s, NH), 7.51-7.67 (6H, m), 7.31 (2H, t), 7.09 (1H, s), 6.55 (2H, br s, NH$_2$), 3.06 (8H, br s).

Example 8

4-[2-Amino-5-(4-fluorophenyl)thieno[2,3-d]pyrimidin-4-yl]-N-(4-chlorophenyl)-piperazine-1-carboxamide Prepared by the procedure described in Example 4, using 4-chlorophenyl isocyanate. $\delta_H$ (300 MHz, DMSO-d$_6$) 8.56 (1H, s, NH), 7.43-7.53 (4H, m), 7.24-7.33 (4H, m), 7.09 (1H, s), 6.55 (2H, br s, NH$_2$), 3.05 (8H, br s).

Example 9

4-[2-Amino-5-(4-fluorophenyl)thieno[2,3-d]pyrimidin-4-yl]-N-[4-(dimethylamino)-phenyl]piperazine-1-carboxamide Prepared by the procedure described in Example 4, using 4-(dimethylamino)-phenyl isocyanate. $^{13}$C NMR $\delta$ (75 MHz, CD$_3$OD) 171.66, 162.43, 161.99 (d, J$_{CF}$ 244.5 Hz), 159.36, 156.57, 147.48, 134.46, 132.80, 129.69 (2C, d, J$_{CF}$ 7.5 Hz), 129.02, 122.83 (2C), 115.44, 114.57 (2C, d, J$_{CF}$ 21.7 Hz), 113.07 (2C), 108.95, 48.74 (2C), 42.36 (2C), 39.91 (2C). MS (m/z) 492 [M+H]$^+$.

Preparative Example 10

2-Amino-4-(piperazin-1-yl)-5-(pyridin-3-yl)thieno[2,3-d]pyrimidine

To a solution of Intermediate 3 (800 mg, 3.3 mmol) in acetonitrile (30 mL) were added DBU (735 µl, 4.9 mmol), BOP (1.883 g, 4.2 mmol) and piperazine (563 mg, 6.5 mmol). The reaction mixture was stirred overnight at room temperature. The solvents were evaporated in vacuo and the crude residue was purified by flash chromatography, the mobile phase being a mixture of methanol and dichloromethane (in a ratio gradually increasing from 5% to 15% methanol in dichloromethane with 0.5% ammonia in methanol solution), yielding the title compound (720 mg) as a yellow powder. $^{13}$C NMR $\delta$ (75 MHz, CD$_3$OD) 172.34, 162.75, 159.92, 148.71, 148.26, 135.48, 132.42, 132.13, 123.45, 116.64, 108.33, 49.88, 43.95. MS (m/z) 313 [M+H]$^+$.

Preparative Example 11

2-Amino-6-methyl-5-phenyl-4-(piperazin-1-yl)thieno[2,3-d]pyrimidine

To a solution of Intermediate 4 (800 mg, 3.1 mmol) in acetonitrile (30 mL) were added DBU (697 µL, 4.7 mmol), BOP (1.787 g, 4.0 mmol) and piperazine (535 mg, 6.2 mmol). The reaction mixture was stirred overnight at room temperature. The solvents were evaporated in vacuo and the crude residue was purified by flash chromatography, the mobile phase being a mixture of methanol and dichloromethane (in a ratio gradually increasing from 2% to 5% methanol in dichloromethane with 0.5% ammonia in methanol solution), yielding the title compound (729 mg) as a white powder. $^{13}$C NMR $\delta$ (75 MHz, CD$_3$OD) 169.47, 162.09, 159.30, 135.52, 130.77, 130.12 (2C), 127.99 (2C), 127.09, 125.53, 110.23, 50.25 (2C), 44.05 (2C), 14.13. MS (m/z) 326 [M+H]$^+$.

Example 12

4-[2-Amino-5-(pyridin-3-yl)thieno[2,3-d]pyrimidin-4-yl]-N-(2-methoxyphenyl)-piperazine-1-carboxamide To a solution of Example 10 (50 mg, 0.15 mmol) in dichloromethane (2 mL) and acetonitrile (1 mL) was added 2-methoxyphenyl isocyanate (21 µL, 0.16 mmol). The reaction mixture was stirred overnight. The reaction mixture was evaporated in vacuo and the crude residue was purified by silica gel flash chromatography, the mobile phase being a mixture of methanol and dichloromethane (in a ratio gradually ranging from 0.5% to 3% methanol in dichloromethane), yielding the title compound (42 mg) as a white powder. MS (m/z) 462 [M+H]$^+$.

Example 13

4-(2-Amino-6-methyl-5-phenylthieno[2,3-d]pyrimidin-4-yl)-N-(4-methoxyphenyl)-piperazine-1-carboxamide To a solution of Example 11 (50 mg, 0.16 mmol) in dichloromethane (2 mL) and acetonitrile (1 mL) was added 4-methoxyphenyl isocyanate (22 µL, 0.17 mmol). The reaction mixture was stirred overnight. The reaction mixture was evaporated in vacuo and the crude residue was purified by silica gel flash chromatography, the mobile phase being a mixture of methanol and dichloromethane (in a ratio gradually ranging from 1% to 2% methanol in dichloromethane), yielding the title compound (49 mg) as a white powder. $^{13}$C NMR $\delta$ (75 MHz, acetone-d$_6$) 169.83, 161.99, 159.36, 155.05, 154.65, 135.58, 133.58, 130.55, 130.10 (2C), 127.84 (2C), 127.00, 126.13, 121.29 (2C), 113.26 (2C), 110.65, 64.94, 54.72 (2C), 49.33 (2C), 13.54. MS (m/z) 475 [M+H]$^+$.

Example 14

3-(4-Fluorophenyl)-4-(4-methylpiperazin-1-yl)isothiazolo[5,4-d]pyrimidine

A suspension of Intermediate 10 (0.5 mmol) in POCl$_3$ (2 mL) was heated at 90° C. for 2 hours. After concentration under reduced pressure, the residue was dissolved in dichloromethane (20 mL) and washed with water. To the organic phase was added 1-methylpiperazine (1.5 mmol). The resulting mixture was stirred at room temperature for 1 hour. After removal of the solvents under reduced pressure, the residue was purified by flash chromatography on silica, the mobile phase being a mixture of methanol and dichloromethane (in a ratio of 1:20), yielding the pure title compound (146 mg, 89%) as a white solid. MS (m/z) 330.1 [M+H]$^+$ (100%). $\delta_H$ (300 MHz, DMSO-d$_6$, 25° C.) 8.61 (s, 1H), 7.73 (dd, J 8.4, 5.6 Hz, 2H), 7.40 (t, J 8.7 Hz, 2H), 3.36 (br s, 4H), 3.30 (br s, 4H), 2.05 (s, 3H).

Preparative Example 15

3-(4-Fluorophenyl)-4-(piperazin-1-yl)isothiazolo[5,4-d]pyrimidin-6-amine

To a suspension of Intermediate 11 (3 mmol) in DMF (5 mL) were added piperazine (15 mmol), BOP (3.6 mmol) and DBU (3.6 mmol). The reaction mixture was stirred at room temperature for 3 h. After concentration under reduced pressure, the residue was extracted with dichloromethane. The extracts were concentrated and purified by flash chromatography on silica, the mobile phase being a mixture of methanol and dichloromethane (in a ratio of 1:5), yielding the pure title compound (400 mg, 40%) as a yellow solid. MS (m/z) 331.2 [M+H]$^+$ (100%). $\delta_H$ (300 MHz, DMSO-d$_6$, 25° C.) 7.67 (dd, J 8.4, 5.6 Hz, 2H), 7.34 (t, J 8.7 Hz, 2H), 7.00 (s, 2H, NH$_2$), 3.36 (br s, 4H), 3.15 (br s, 4H).

Example 16

3-(4-Fluorophenyl)-4-(4-methylpiperazin-1-yl)isothiazolo[5,4-d]pyrimidin-6-amine Prepared in 48% yield by the procedure described in Example 14, using Intermediate 11. MS (m/z) 345.2 [M+H]$^+$ (100%). $\delta_H$ (300 MHz, DMSO-d$_6$, 25° C.) 7.68 (dd, J 8.4, 5.6 Hz, 2H), 7.34 (t, J 8.7 Hz, 2H), 7.00 (s, 2H, NH$_2$), 3.36 (br s, 4H), 3.15 (br s, 4H), 2.05 (s, 3H).

Example 17

4-[6-Amino-3-(4-fluorophenyl)isothiazolo[5,4-d]pyrimidin-4-yl]-N-(p-tolyl)piperazine-1-carboxamide To a suspension of Example 15 (0.2 mmol) in dichloromethane (5 mL) was added p-tolyl isocyanate (0.2 mmol). The reaction mixture was stirred at room temperature for 30 minutes. After concentration under reduced pressure, the residue was purified by flash chromatography on silica, the mobile phase being a mixture of methanol and dichloromethane (in a ratio of 1:50), yielding the pure title compound (66 mg, 71%) as a yellowish solid. MS (m/z) 464.1 [M+H]$^+$ (100%). $\delta_H$ (300 MHz, DMSO-d$_6$, 25° C.) 8.36 (s, 1H, NH), 7.72 (dd, J 8.4, 5.6 Hz, 2H), 7.38 (t, J 8.7 Hz, 2H), 7.26 (d, J 8.4 Hz, 2H), 7.06 (s, 2H, NH$_2$), 7.01 (d, J 8.4 Hz, 2H), 3.36 (br s, 4H), 3.17 (br s, 4H), 2.20 (s, 3H).

Example 18

4-[6-Amino-3-(4-fluorophenyl)isothiazolo[5,4-d]pyrimidin-4-yl]-N-(4-isopropylphenyl)-piperazine-1-carboxamide Prepared by the procedure described in Example 17, using 4-isopropylphenyl isocyanate, yielding the pure title compound in 79% yield as a white solid. MS (m/z) 492.2 [M+H]$^+$ (100%). $\delta_H$ (300 MHz, DMSO-d$_6$, 25° C.) 8.38 (s, 1H, NH), 7.72 (dd, J 8.4, 5.6 Hz, 2H), 7.38 (t, J 8.7 Hz, 2H), 7.29 (d, J 8.2 Hz, 2H), 7.08 (s, 2H, NH$_2$), 6.95 (d, J 8.2 Hz, 2H), 3.38 (br s, 4H), 3.18 (br s, 4H), 2.79 (m, 1H), 1.19 (d, J 6.0 Hz, 6H).

Example 19

1-{4-[6-Amino-3-(4-fluorophenyl)isothiazolo[5,4-d]pyrimidin-4-yl]piperazin-1-yl}-2-(4-chlorophenoxy)ethanone To a suspension of Example 15 (0.2 mmol) and potassium carbonate (0.2 mmol) in 1,4-dioxane (5 mL) was added 4-chlorophenoxyacetyl chloride (0.2 mmol). The reaction mixture was stirred at room temperature for 1 hour. After concentration under reduced pressure, the crude residue was purified by flash chromatography on silica, the mobile phase being a mixture of methanol and dichloromethane (in a ratio of 1:60), yielding the pure title compound (80 mg, 80%) as a yellowish solid. MS (m/z) 499.2 [M+H]$^+$ (100%). $^1$H NMR $\delta_H$ (300 MHz, DMSO-d$_6$, 25° C.) 7.72 (dd, J 8.4, 5.6 Hz, 2H), 7.38 (t, J 8.7 Hz, 2H), 7.30 (d, J 8.8 Hz, 2H), 7.08 (s, 2H, NH$_2$), 6.89 (d, J 8.8 Hz, 2H), 4.76 (s, 2H), 3.34 (br s, 4H), 3.20 (br s, 4H).

Preparative Example 20

2-Amino-5-(ethoxycarbonyl)-4-(piperazin-1-yl)thieno[2,3-d]pyrimidine

To a solution of Intermediate 13 (700 mg, 2.90 mmol) in acetonitrile (30 mL) were added DBU (656 µL, 4.40 mmol), BOP (1.682 g, 3.80 mmol) and piperazine (503 mg, 58.50 mmol). The reaction mixture was stirred overnight at room temperature. The solvents were evaporated in vacuo and the crude residue was purified by flash chromatography, the mobile phase being a mixture of methanol and dichloromethane (in a ratio gradually increasing from 3% to 5% methanol in dichloromethane with 0.5% aqueous ammonia solution), yielding the title compound (461 mg) as a white powder. $^{13}$C NMR $\delta$ (75 MHz, CD$_3$OD) 175.25, 166.63, 164.46, 162.86, 131.21, 128.87, 110.83, 64.99, 52.76 (2C), 48.66 (2C), 17.72. MS (m/z) 308 [M+H]$^+$.

Example 21

4-[2-Amino-5-(ethoxycarbonyl)thieno[2,3-d]pyrimidin-4-yl]-N-(4-methoxyphenyl)-piperazine-1-carboxamide To a solution of Example 20 (70 mg, 0.23 mmol) in dichloromethane (2 mL) and acetonitrile (2 mL) was added 4-methoxyphenyl isocyanate (31 µL, 0.24 mmol). The reaction mixture was stirred overnight. The solvents were evaporated in vacuo and the crude residue was purified by flash chromatography, the mobile phase being a mixture of methanol and dichloromethane (in a ratio gradually increasing from 1% to 3% methanol in dichloromethane), yielding the title compound (61 mg) as a white powder. $^{13}$C NMR $\delta$ (75 MHz, CD$_3$OD) 171.65, 162.60, 160.54, 159.64, 155.32, 154.73, 133.60, 127.71, 124.13, 121.41 (2C), 113.30 (2C), 106.19, 60.79, 54.73, 47.93 (2C), 43.38 (2C), 13.73. MS (m/z) 457 [M+H]$^+$.

Preparative Example 22

2-Amino-5-methyl-4-(piperazin-1-yl)thieno[2,3-d]pyrimidine

To a solution of Intermediate 14 (300 mg, 1.65 mmol) in acetonitrile (15 mL) were added DBU (370 µL, 2.45 mmol), BOP (952 mg, 2.15 mmol) and piperazine (285 mg, 3.31 mmol). The reaction mixture was stirred overnight at room temperature. The solvents were evaporated in vacuo and the crude residue was purified by flash chromatography, the mobile phase being a mixture of methanol and dichloromethane (in a ratio gradually increasing from 2% to 4% methanol in dichloromethane with 0.5% aqueous ammonia solution), yielding the title compound (471 mg) as a yellow powder. $^{13}$C NMR $\delta$ (75 MHz, CDCl$_3$, CD$_3$OD) 175.06, 168.30, 162.64, 133.34, 117.63, 117.56, 54.75 (2C), 48.64 (2C), 20.44. MS (m/z) 250 [M+H]$^+$.

Preparative Example 23

2-Amino-5-isobutyl-4-(piperazin-1-yl)thieno[2,3-d]pyrimidine

Prepared using Intermediate 15 (300 mg, 1.34 mmol) applying the procedure described in Example 22. The title compound (408 mg) was isolated as a yellow powder. $^{13}$C NMR δ (75 MHz, CDCl$_3$, CD$_3$OD) 175.32, 168.63, 162.72, 137.87, 117.74, 117.02, 54.90 (2C), 48.78 (2C), 43.67, 32.80, 25.79 (2C). MS (m/z) 292 [M+H]$^+$.

Example 24

4-[2-Amino-5-methylthieno[2,3-d]pyrimidin-4-yl]-N-[4-(dimethylamino)phenyl]-piperazine-1-carboxamide To a solution of Example 22 (70 mg, 0.28 mmol) in dichloromethane (2 mL) and acetonitrile (2 mL) was added 4-(dimethylamino)phenyl isocyanate (48 mg, 0.29 mmol). The reaction mixture was stirred overnight. The solvents were evaporated in vacuo and the crude residue was purified by flash chromatography, the mobile phase being a mixture of methanol and dichloromethane (in a ratio gradually increasing from 1% to 4% methanol in dichloromethane), yielding the title compound (75 mg) as a white powder. $^{13}$C NMR δ (75 MHz, CDCl$_3$) 171.76, 164.09, 158.58, 155.98, 147.34, 129.12, 128.44, 122.79 (2C), 114.11 (2C), 113.95, 113.07, 49.96 (2C), 43.42 (2C), 40.79 (2C), 16.75. MS (m/z) 412 [M+H]$^+$.

Example 25

4-[2-Amino-5-isobutylthieno[2,3-d]pyrimidin-4-yl]-N-[4-(dimethylamino)phenyl]-piperazine-1-carboxamide Prepared using Example 23 (70 mg, 0.24 mmol) applying the procedure described in Example 24. The title compound (73 mg) was isolated as a white powder. $^{13}$C NMR δ (75 MHz, CDCl$_3$) 172.07, 164.31, 158.49, 155.93, 147.41, 133.63, 128.36, 122.76 (2C), 114.39, 113.47, 113.02 (2C), 50.07 (2C), 43.50 (2C), 40.75 (2C), 39.91, 28.90, 22.11 (2C). MS (m/z) 454 [M+H]$^+$.

Example 26

2-Amino-4-[4-(4-methoxyphenylcarbamoyl)piperazin-1-yl]thieno[2,3-d]pyrimidine-5-carboxylic acid To a solution of Example 21 (900 mg, 1.97 mmol) in ethanol/THF (1:1, 10 mL) was added aqueous NaOH solution (2M, 10 mL). The reaction mixture was heated to 50° C. for 12 hours. On completion, the reaction mixture was concentrated in vacuo and then re-dissolved in warm water. The pH was adjusted to pH 5-6 with 2M HCl, and the precipitate was filtered and dried on a sinter to give the title compound (460 mg) as a white solid. δ$_H$ (DMSO-d$_6$, 300 MHz) 8.43 (1H, s), 7.68 (1H, s), 7.35 (2H, d, J 8.8 Hz), 6.82 (2H, d, J 8.8 Hz), 6.44 (2H, br s), 3.70 (3H, s), 3.49-3.34 (8H, br m+H$_2$O). LCMS (pH 10) MH$^+$ 429, RT 0.79 minutes. LCMS (pH 3) MH$^+$ 429, RT 1.15 minutes.

Example 27

2-Amino-4-[4-(4-methoxyphenylcarbamoyl)piperazin-1-yl]thieno[2,3-d]pyrimidine-5-carboxylic acid methylamide To a stirred sample of Example 26 (100 mg, 0.23 mmol) in DMF (5 mL) were added EDC (49 mg, 0.25 mol), methylamine (2M in THF, 0.14 mL, 0.28 mmol) and HOBT (38 mg, 0.25 mmol). The reaction mixture was stirred at room temperature overnight. On completion, the solvent was removed in vacuo and the crude residue was dissolved in EtOAc (25 mL), washed with brine (3×20 mL) and concentrated in vacuo. The resultant solid was triturated with EtOAc, filtered and dried on a sinter to give the title compound (26 mg) as a white solid. δ$_H$ (DMSO-d$_6$, 300 MHz) 8.39 (1H, s), 8.25 (1H, br d, J 9.1 Hz), 7.35 (2H, d, J 9.1 Hz), 7.32 (1H, s), 6.82 (2H, m), 6.44 (2H, br s), 3.71 (3H, s), 3.48 (4H, br m), 3.38 (4H, br m), 2.76 (3H, d, J 4.6 Hz). LCMS (pH 10) MH$^+$ 442, RT 1.28 minutes. LCMS (pH 3) MH$^+$ 442, RT 1.04 minutes.

Example 28

2-Amino-4-[4-(4-methoxyphenylcarbamoyl)piperazin-1-yl]thieno[2,3-d]pyrimidine-5-carboxylic acid N-methoxy-N-methylamide To a stirred sample of Example 26 (220 mg) in DMF (10 mL) were added EDC (108 mg), N,O-dimethylhydroxylamine hydrochloride (60 mg), HOBT (85 mg) and N,N-diisopropylethylamine (176 µL). The reaction mixture was stirred at room temperature overnight. On completion, the solvent was removed in vacuo and the crude residue was dissolved in EtOAc (45 mL), washed with brine (3×30 mL) and concentrated in vacuo. The crude material was purified by column chromatography, eluting with EtOAc→3% MeOH, to give the title compound (130 mg) as a white solid. δ$_H$ (DMSO-d$_6$, 300 MHz) 8.40 (1H, s), 7.39 (1H, s), 7.35 (2H, d, J 9.0 Hz), 6.83 (2H, d, J 9.1 Hz), 6.51 (2H, br s), 3.71 (3H, s), 3.58 (3H, br s), 3.49 (4H, br m), 3.33 (4H, br m), 3.23 (3H, s). LCMS (pH 10) MH$^+$ 472, RT 1.51 minutes. LCMS (pH 3) MH$^+$ 472, RT 1.29 minutes.

Example 29

2-Amino-4-[4-(4-methoxyphenylcarbamoyl)piperazin-1-yl]thieno[2,3-d]pyrimidine-5-carboxylic acid amide To a stirred sample of Example 26 (100 mg, 0.23 mmol) in DMF (5 mL) were added EDC (49 mg, 0.25 mol), aqueous ammonia (1 mL) and HOBT (38 mg, 0.25 mmol). The reaction mixture was stirred at room temperature overnight. A further aliquot of aqueous ammonia (1 mL) was added, and stirring was continued for 6 hours. The solvent was removed in vacuo and the crude residue was dissolved in EtOAc (25 mL), washed with brine (3×20 mL) and concentrated in vacuo. The residue was suspended in EtOAc and the precipitated white solid was filtered and dried on a sinter, to give the title compound (2 mg). δ$_H$ (DMSO-d$_6$, 300 MHz) 8.42 (1H, br s), 7.76 (1H, br s), 7.36 (1H, br s), 7.35 (2H, d, J 9.0 Hz), 7.34 (1H, s), 6.83 (2H, d, J 9.0 Hz), 6.43 (2H, br s), 3.71 (3H, s), 3.53 (4H, br m), 3.42 (4H, br m). LCMS (pH 10) MH$^+$ 428, RT 1.18 minutes. LCMS (pH 3) MH$^+$ 428, RT 0.95 minutes.

General Method 9

To a solution of Preparative Example 1 (100 mg, 0.3 mmol) in 1,4-dioxane (15 mL) were added DIPEA (131 µL, 0.75 mmol) and the appropriate acid chloride (0.31 mmol). The reaction was stirred at room temperature overnight. The reaction mixture was diluted with dichloromethane and the organic layers were extracted several times with water. The combined organic layers were evaporated in vacuo and the crude residue was purified by silica gel flash chromatography, the mobile phase being a mixture of methanol and dichloromethane (in a ratio gradually ranging from 0.5% to 1% methanol in dichloromethane), providing the title compound as a white powder, in yields varying from 60 to 75%.

Example 30

Benzyl 4-[2-amino-5-(4-fluorophenyl)thieno[2,3-d]pyrimidin-4-yl]piperazine-1-carboxylate Prepared via General Method 9, using Preparative Example 1 and benzyl chloroformate. $^{13}$C NMR δ (75 MHz, CDCl$_3$) 172.48, 164.23, 162.59 (d, J$_{CF}$ 246.0 Hz), 159.36, 155.52, 136.60, 135.03, 133.22, 130.22 (2C, d, J$_{CF}$ 7.8 Hz), 128.79 (2C), 128.44, 128.19 (2C), 116.67, 115.64 (2C, d, J$_{CF}$ 21.4 Hz), 110.12, 67.67, 49.44 (2C), 43.02 (2C). MS (m/z) 464 [M+H]$^+$.

Example 31

4-Methoxyphenyl 4-[2-amino-5-(4-fluorophenyl)thieno[2,3-d]pyrimidin-4-yl]piperazine-1-carboxylate Prepared via General Method 9, using Preparative Example 1 and 4-methoxy-phenyl chloroformate. $^{13}$C NMR δ (75 MHz, CDCl$_3$) 171.98, 162.30, 161.94 (d, J$_{CF}$ 246.1 Hz), 158.65, 156.64, 153.67, 144.25, 134.33, 132.56 (d, J$_{CF}$ 3.3 Hz), 129.59 (2C, d, J$_{CF}$ 7.8 Hz), 122.06 (2C), 116.15, 115.01 (2C, d, J$_{CF}$ 21.3 Hz), 113.95 (2C), 109.54, 55.18, 48.50 (2C), 42.93, 42.42. MS (m/z) 480 [M+H]$^+$.

Example 32

5-(4-Fluorophenyl)-4-[4-(3-methylbenzylsulfonyl)piperazin-1-yl]thieno[2,3-d]pyrimidin-2-amine Prepared via General Method 9, using Preparative Example 1 and m-tolyl-methanesulfonyl chloride. $^{13}$C NMR δ (75 MHz, CDCl$_3$) 171.96, 162.14, 162.04 (d, J$_{CF}$ 245.7 Hz), 158.83, 138.35, 134.32, 132.66 (d, J$_{CF}$ 3.3 Hz), 131.03, 129.77 (2C, d, J$_{CF}$ 7.8 Hz), 129.40, 128.37, 127.39, 116.24, 115.08 (2C, d, J$_{CF}$ 21.3 Hz), 109.50, 56.32, 49.13 (2C), 44.55 (2C), 20.91. MS (m/z) 498 [M+H]$^+$.

Example 33

5-(4-Fluorophenyl)-4-[4-(2-methyl-1H-imidazol-1-ylsulfonyl)piperazin-1-yl]thieno[2,3-d]pyrimidin-2-amine To a solution of Preparative Example 1 (70 mg, 0.21 mmol) in acetonitrile (4 mL) was added 2-methyl-1-(2-methyl-1H-imidazol-1-ylsulfonyl)-3-(trifluoromethylsulfonyl)-1H-imidazol-3-ium methanolate (91 mg, 0.23 mmol; prepared according to S. Beaudoin, K. E. Kinsey & J. F. Burns, *J. Org. Chem.*, 2003, 68, 115-119). The reaction mixture was stirred at room temperature overnight. The solvents were evaporated in vacuo and the crude residue was purified by silica gel flash chromatography, the mobile phase being a mixture of ethyl acetate and heptane (in a ratio gradually ranging from 20% to 30% ethyl acetate in heptane), yielding the title compound (53 mg). $^{13}$C NMR δ (75 MHz, CDCl$_3$) 172.66, 161.89 (d, J$_{CF}$ 247.1 Hz), 161.73, 158.58, 145.39, 133.87, 132.47 (d, J$_{CF}$ 3.4 Hz), 129.78 (2C, d, J$_{CF}$ 7.8 Hz), 127.35, 119.03, 116.90, 115.07 (2C, d, J$_{CF}$ 21.2 Hz), 109.69, 48.10 (2C), 45.12 (2C), 15.27. MS (m/z) 474 [M+H]$^+$.

Example 34

4-[2-Amino-5-(4-fluorophenyl)thieno[2,3-d]pyrimidin-4-yl]-N-(4-methoxyphenyl)-piperazine-1-sulfonamide To a solution of Preparative Example 1 (50 mg, 0.10 mmol) in dichloromethane (4 mL) was added methyl trifluoromethanesulfonate (13 μL, 0.12 mmol) at −10° C. The reaction mixture was stirred at 0° C. for 2 h. The solvents were evaporated in vacuo and the crude residue was dissolved in acetonitrile (2 mL), then 4-methoxyaniline (14 mg, 0.11 mmol) was added. The reaction mixture was stirred at 80° C. overnight. The solvents were evaporated in vacuo and the crude residue was purified by silica gel flash column chromatography, the mobile phase being a mixture of methanol and dichloromethane (in a ratio gradually ranging from 1% to 2% methanol in dichloromethane), yielding the title compound (29 mg). $^{13}$C NMR δ (75 MHz, CDCl$_3$) 172.42, 162.06, 161.88 (d, J$_{CF}$ 246.0 Hz), 158.57, 157.34, 134.20, 132.59, 129.56 (2C, d, J$_{CF}$ 7.7 Hz), 128.99, 124.15 (2C), 116.35, 115.03 (2C, d, J$_{CF}$ 21.2 Hz), 114.21 (2C), 109.60, 55.16, 48.61 (2C), 44.88 (2C). MS (m/z) 515 [M+H]$^+$.

General Method 10

To a solution of the appropriate piperazine derivative (0.15 mmol) in DCM (2 mL) and acetonitrile (2 mL) or DMF (4 mL) was added an appropriate isocyanate (0.16 mmol). The reaction mixture was stirred overnight. The reaction mixture was diluted with DCM and the organic layers were extracted several times with water. The combined organic layers were evaporated in vacuo and the crude residue was purified by silica gel flash chromatography, the mobile phase being a mixture of MeOH and DCM (in a ratio gradually ranging from 0.5% to 1% MeOH in DCM), providing the title compound as a white powder, in yields varying from 65 to 85%.

Example 35

4-[2-Amino-5-(4-fluorophenyl)thieno[2,3-d]pyrimidin-4-yl]-N-[3-(morpholin-4-ylmethyl)phenyl]piperazine-1-carboxamide Prepared via General Method 10 using Preparative Example 1 and 4-(3-isocyanatobenzyl)morpholine. $^{13}$C NMR δ (75 MHz, CDCl$_3$) 172.48, 162.20, 161.94 (d, J$_{CF}$ 246.0 Hz), 158.63, 154.43, 138.50, 138.27, 134.34, 132.72, 129.59 (2C, d, J$_{CF}$ 7.5 Hz), 128.42, 123.80, 120.31, 118.53, 116.28, 115.06 (2C, d, J$_{CF}$ 21.3 Hz), 109.66, 66.61 (2C), 63.02, 53.28 (2C), 48.82 (2C), 42.68 (2C). MS (m/z) 548 [M+H]$^+$.

Example 36

4-[2-Amino-5-(4-fluorophenyl)thieno[2,3-d]pyrimidin-4-yl]-N-[4-(4-methylpiperazin-1-yl)phenyl]piperazine-1-carboxamide Prepared via General Method 10 using Preparative Example 1 and 1-(4-isocyanatophenyl)-4-methylpiperazine. $^{13}$C NMR δ (75 MHz, CDCl$_3$) 175.65, 166.22, 165.90 (d, J$_{CF}$ 245.7 Hz), 162.69, 159.82, 150.87, 138.41, 136.54, 135.60, 133.49 (2C, d, J$_{CF}$ 7.5 Hz), 125.91 (2C), 120.57 (2C), 119.82, 118.89 (2C, d, J$_{CF}$ 21.3 Hz), 113.33, 58.40 (2C), 53.15 (2C), 52.28 (2C), 49.17, 46.44 (2C). MS (m/z) 547 [M+H]$^+$.

Example 37

4-[2-Amino-5-(4-fluorophenyl)thieno[2,3-d]pyrimidin-4-yl]-N-(4-fluorophenyl)-piperazine-1-carboxamide Prepared via General Method 10 using Preparative Example 1 and 4-fluorophenyl isocyanate. $^{13}$C NMR δ (75 MHz, CDCl$_3$) 174.02, 166.06, 165.94 (d, J$_{CF}$ 246.0 Hz), 162.52 (d, J$_{CF}$ 240.0 Hz), 162.07, 159.78, 140.65, 138.74 (d, J$_{CF}$ 3.7 Hz), 138.48, 136.39 (d, J$_{CF}$ 3.7 Hz), 133.48 (2C, d, J$_{CF}$ 7.5 Hz), 126.45 (2C, d, J$_{CF}$ 7.5 Hz), 119.94, 118.98 (2C, d, J$_{CF}$ 21.7 Hz), 118.57 (2C, d, J$_{CF}$ 22.5 Hz), 113.28, 52.77 (2C), 46.52 (2C). MS (m/z) 467 [M+H]$^+$.

Example 38

4-[2-Amino-5-(4-fluorophenyl)thieno[2,3-d]pyrimidin-4-yl]-N-(2,4-dimethoxyphenyl)-piperazine-1-carboxamide Prepared via General Method 10 using Preparative Example 1 and 2,4-dimethoxyphenyl isocyanate. $^{13}$C NMR δ (75 MHz, CDCl$_3$) 172.40, 162.19, 161.93 (d, J$_{CF}$ 246.1 Hz), 158.70, 155.29, 154.52, 148.89, 134.40, 132.70 (d, J$_{CF}$ 3.3 Hz), 129.57 (2C, d, J$_{CF}$ 8.2 Hz), 121.56, 120.20, 116.08, 115.01 (2C, d, J$_{CF}$ 21.0 Hz), 109.56, 103.65, 98.27, 55.41, 55.20, 48.77 (2C), 42.55 (2C). MS (m/z) 509 [M+H]$^+$.

Example 39

4-[2-Amino-5-(4-fluorophenyl)thieno[2,3-d]pyrimidin-4-yl]-N-[4-(piperidin-1-ylmethyl)-phenyl]piperazine-1-carboxamide Prepared via General Method 10 using Preparative Example 1 and 1-(4-isocyanatobenzyl)piperidine. $^{13}$C NMR δ (75 MHz, CDCl$_3$) 172.47, 162.19, 161.93 (d, J$_{CF}$ 246.0 Hz), 158.63, 155.29, 154.58, 137.23, 134.37, 132.92, 132.69 (d, J$_{CF}$ 3.0 Hz), 129.57 (2C, d, J$_{CF}$ 7.5 Hz), 129.48 (2C), 119.50 (2C), 116.22, 115.05 (2C, d, J$_{CF}$ 21.0 Hz), 109.64, 62.92, 54.01 (2C), 48.81 (2C), 42.70 (2C), 25.55, 24.01. MS (m/z) 546 [M+H]$^+$.

Example 40

4-[2-Amino-5-(4-fluorophenyl)thieno[2,3-d]pyrimidin-4-yl]-N-(2,4-difluorophenyl)-piperazine-1-carboxamide Prepared via General Method 10 using Preparative Example 1 and 2,4-difluorophenyl isocyanate. $^{13}$C NMR δ (75 MHz, CDCl$_3$) 175.72, 166.15, 165.90 (d, J$_{CF}$ 246.0 Hz), 162.64, 162.53 (dd, J$_{CF}$ 243.7, 11.2 Hz), 159.01, 128.28 (dd, J$_{CF}$ 245.2, 12.0 Hz), 138.33, 136.50 (d, J$_{CF}$ 3.7 Hz), 133.50 (2C, d, J$_{CF}$ 7.5 Hz), 129.09 (d, J$_{CF}$ 9.0 Hz), 126.52 (dd, J$_{CF}$ 12.7, 3.7 Hz), 119.94, 118.91 (2C, d, J$_{CF}$ 21.7 Hz), 114.41 (dd, J$_{CF}$ 21.7, 3.7 Hz), 113.36, 107.16 (t, J$_{CF}$ 24.0 Hz), 52.61 (2C), 46.51 (2C). MS (m/z) 485 [M+H]$^+$.

Example 41

4-[2-Amino-5-(pyridin-3-yl)thieno[2,3-d]pyrimidin-4-yl]-N-[4-(dimethylamino)phenyl]-piperazine-1-carboxamide Prepared via General Method 10 using Preparative Example 10 and 4-(dimethyl-amino)phenyl isocyanate. $^{13}$C NMR δ (75 MHz, acetone-d$_6$) 172.59, 162.68, 159.98, 155.27, 148.75, 148.22, 146.47, 135.37 (2C), 132.46, 132.08, 130.54, 123.22 (2C), 121.45, 116.64, 112.76, 108.61, 49.30 (2C), 42.65 (2C), 40.40 (2C). MS (m/z) 475 [M+H]$^+$.

Example 42

4-[2-Amino-5-(pyridin-3-yl)thieno[2,3-d]pyrimidin-4-yl]-N-(4-methoxyphenyl)-piperazine-1-carboxamide Prepared via General Method 10 using Preparative Example 10 and 4-methoxy-phenyl isocyanate. $^{13}$C NMR δ (75 MHz, acetone-d$_6$) 172.60, 162.67, 159.98, 155.11, 154.67, 148.76, 148.23, 135.38, 133.54, 132.46, 132.07, 123.22, 121.29 (2C), 116.66, 113.26 (2C), 108.61, 54.71, 49.29 (2C), 42.65 (2C). MS (m/z) 462 [M+H]$^+$.

Example 43

4-[2-Amino-5-(pyridin-3-yl)thieno[2,3-d]pyrimidin-4-yl]-N-(3-methylphenyl)piperazine-1-carboxamide Prepared via General Method 10 using Preparative Example 10 and 3-methyl-phenyl isocyanate. $^{13}$C NMR δ (75 MHz, DMSO-d$_6$) 173.50, 163.48, 160.73, 155.57, 149.59, 148.98, 141.20, 138.13, 136.04, 133.27, 132.90, 128.62, 123.86, 123.03, 120.72, 117.42, 117.26, 109.58, 50.06 (2C), 43.49 (2C), 21.31. MS (m/z) 446 [M+H]$^+$.

Example 44

4-[2-Amino-5-(pyridin-3-yl)thieno[2,3-d]pyrimidin-4-yl]-N-[3-(morpholin-4-ylmethyl)-phenyl]piperazine-1-carboxamide Prepared via General Method 10 using Preparative Example 10 and 4-(3-isocyanatobenzyl)morpholine. $^{13}$C NMR δ (75 MHz, CDCl$_3$) 172.65, 162.38, 158.81, 154.50, 148.81, 148.36, 138.50, 138.25, 135.03, 132.33, 131.59, 128.37, 123.76, 122.96, 120.33, 118.52, 117.63, 109.54, 66.60 (2C), 63.01, 53.26 (2C), 48.97 (2C), 42.60 (2C). MS (m/z) 531 [M+H]$^+$.

Example 45

4-[2-Amino-5-(pyridin-3-yl)thieno[2,3-d]pyrimidin-4-yl]-N-[4-(piperidin-1-ylmethyl)-phenyl]piperazine-1-carboxamide Prepared via General Method 10 using Preparative Example 10 and 1-(4-isocyanatobenzyl)piperidine. $^{13}$C NMR δ (75 MHz, CDCl$_3$) 172.55, 162.40, 158.89, 154.78, 148.73, 148.26, 138.75, 135.05, 132.34, 131.63, 130.10 (2C), 128.80, 123.01, 119.70 (2C), 117.49, 109.46, 61.99, 53.39 (2C), 49.04 (2C), 42.73 (2C), 24.36 (2C), 23.20. MS (m/z) 529 [M+H]$^+$.

Example 46

4-[2-Amino-5-(4-methoxyphenyl)thieno[2,3-d]pyrimidin-4-yl]-N-(4-methoxyphenyl)-piperazine-1-carboxamide Prepared via General Method 10 using Intermediate 26 and 4-methoxyphenyl isocyanate. $^{13}$C NMR δ (75 MHz, CDCl$_3$) 175.43, 166.24, 162.80, 160.00, 159.47, 139.28, 135.63, 133.09, 132.96 (2C), 126.75, 126.63 (2C), 118.82, 117.41 (2C), 117.38 (2C), 113.48, 58.85, 58.78, 52.73 (2C), 46.44 (2C). MS (m/z) 491 [M+H]$^+$.

Example 47

4-[2-Amino-5-(4-methoxyphenyl)thieno[2,3-d]pyrimidin-4-yl]-N-(3-methylphenyl)-piperazine-1-carboxamide Prepared via General Method 10 using Intermediate 26 and 3-methylphenyl isocyanate. $^{13}$C NMR δ (75 MHz, CDCl$_3$) 175.44, 166.25, 162.83, 162.71, 159.75, 142.62, 141.85, 139.29, 133.08, 132.96 (2C), 131.90, 127.41, 125.06, 121.43, 118.73, 117.34 (2C), 113.42, 58.68, 52.72 (2C), 46.51 (2C), 24.56. MS (m/z) 475 [M+H]$^+$.

Example 48

4-[2-Amino-5-(4-methoxyphenyl)thieno[2,3-d]pyrimidin-4-yl]-N-(2-methoxyphenyl)-piperazine-1-carboxamide Prepared via General Method 10 using Intermediate 26 and 2-methoxyphenyl isocyanate. $^{13}$C NMR δ (75 MHz, CDCl$_3$) 172.35, 162.19, 158.87, 158.55, 154.12, 147.30, 135.24, 129.24, 129.10 (2C), 128.22, 121.87, 120.86, 118.79, 115.22, 113.45 (2C), 109.81, 109.45, 55.41, 55.05, 48.75 (2C), 42.59 (2C). MS (m/z) 491 [M+H]$^+$.

Example 49

4-[2-Amino-5-(4-methoxyphenyl)thieno[2,3-d]pyrimidin-4-yl]-N-[4-(dimethylamino)-phenyl]piperazine-1-carboxamide Prepared via General Method 10 using Intermediate 26 and 4-(dimethylamino)-phenyl isocyanate. $^{13}$C NMR δ (75 MHz, CDCl$_3$) 175.47, 166.24, 162.80, 162.62, 160.16, 151.29, 139.29, 133.09, 132.96 (4C), 126.68, 118.78, 117.38 (4C), 113.47, 58.79, 53.05 (2C), 46.45 (2C), 44.71 (2C). MS (m/z) 504 [M+H]$^+$.

Example 50

4-[2-Amino-5-(4-chlorophenyl)thieno[2,3-d]pyrimidin-4-yl]-N-(4-methoxyphenyl)-piperazine-1-carboxamide Prepared via General Method 10 using Intermediate 27 and 4-methoxyphenyl isocyanate. $^{13}$C NMR δ (75 MHz, CDCl$_3$) 175.83, 166.06, 159.63, 159.49, 138.83, 138.22, 137.16 (2C), 135.42, 133.06 (2C), 132.15 (2C), 126.43 (2C), 120.25, 117.54 (2C), 113.16, 58.99, 52.64 (2C), 46.42 (2C). MS (m/z) 495 [M+H]$^+$.

Example 51

4-[2-Amino-5-(4-chlorophenyl)thieno[2,3-d]pyrimidin-4-yl]-N-[4-(dimethylamino)-phenyl]piperazine-1-carboxamide Prepared via General Method 10 using Intermediate 27 and 4-(dimethylamino)-phenyl isocyanate. $^{13}$C NMR δ (75 MHz, CDCl$_3$) 175.71, 166.11, 162.71, 160.13, 151.34, 138.86, 138.27, 137.13, 133.09 (2C), 132.74, 132.13 (2C), 126.69 (2C), 120.13, 117.37 (2C), 113.10, 52.66 (2C), 46.42 (2C), 44.75 (2C). MS (m/z) 508 [M+H]$^+$.

Example 52

4-[2-Amino-5-(4-chlorophenyl)thieno[2,3-d]pyrimidin-4-yl]-N-(2-methoxyphenyl)-piperazine-1-carboxamide Prepared via General Method 10 using Intermediate 27 and 2-methoxyphenyl isocyanate. $^{13}$C NMR δ (75 MHz, CDCl$_3$) 172.53, 162.06, 158.71, 154.11, 147.35, 135.01, 134.25, 133.22, 129.18 (2C), 128.23 (2C), 128.19, 121.92, 120.84, 118.87, 116.45, 109.47, 109.36, 55.43, 48.72 (2C), 42.55 (2C). MS (m/z) 495 [M+H]$^+$.

Example 53

4-[2-Amino-5-(4-chlorophenyl)thieno[2,3-d]pyrimidin-4-yl]-N-(3-methylphenyl)-piperazine-1-carboxamide Prepared via General Method 10 using Intermediate 27 and 3-methylphenyl isocyanate. $^{13}$C NMR δ (75 MHz, CDCl$_3$) 175.80, 166.06, 162.62, 159.38, 142.40, 142.06, 138.82, 138.23, 137.16, 133.07 (2C), 132.15 (2C), 132.05, 127.55, 124.82, 121.14, 120.24, 113.14, 52.76 (2C), 46.42 (2C), 24.83. MS (m/z) 479 [M+H]$^+$.

Example 54

4-[2-Amino-5-(3-fluorophenyl)thieno[2,3-d]pyrimidin-4-yl]-N-[4-(dimethylamino)-phenyl]piperazine-1-carboxamide Prepared via General Method 10 using Intermediate 28 and 4-(dimethylamino)-phenyl isocyanate. $^{13}$C NMR δ (75 MHz, acetone-d$_6$) 175.67, 166.21 (d, J$_{CF}$ 244.7 Hz), 166.15, 162.79, 160.24, 151.36, 142.40 (d, J$_{CF}$ 7.9 Hz), 138.28, 133.59 (d, J$_{CF}$ 8.4 Hz), 132.90, 127.51 (d, J$_{CF}$ 2.6 Hz), 126.69, 120.42 (2C), 118.82 (d, J$_{CF}$ 21.7 Hz), 118.00 (d, J$_{CF}$ 20.9 Hz), 117.42 (2C), 113.05, 52.68 (2C), 46.40 (2C), 44.72 (2C). MS (m/z) 492 [M+H]$^+$.

Example 55

4-[2-Amino-5-(2-fluorophenyl)thieno[2,3-d]pyrimidin-4-yl]-N-[4-(dimethylamino)-phenyl]piperazine-1-carboxamide Prepared via General Method 10 using Intermediate 29 and 4-(dimethylamino)-phenyl isocyanate. $^{13}$C NMR δ (75 MHz, CDCl$_3$+CD$_3$OD) 171.9 (C-4), 163.2 (C-7a), 159.2 (C-2), 158.2 (d, J$_{CF}$ 246.9 Hz, phenyl), 155.7 (C=O), 147.6 (phenyl), 131.3 (C-5, phenyl), 129.7 (d, J$_{CF}$ 7.6 Hz, phenyl), 128.6 (phenyl), 124.7 (d, J$_{CF}$ 14.4 Hz, phenyl), 124.3 (phenyl), 122.8 (phenyl), 118.1 (C-6), 115.9 (d, J$_{CF}$ 21.9 Hz, phenyl), 113.5 (phenyl), 111.3 (C-4a), 49.5 (NCH$_2$), 43.1 (NCH$_2$), 41.2 (NCH$_3$). MS (m/z) 492 [M+H]$^+$.

Example 56

4-[2-Amino-5-(2-fluorophenyl)thieno[2,3-c]pyrimidin-4-yl]-N-[4-(4-methylpiperazin-1-yl)phenyl]piperazine-1-carboxamide Prepared via General Method 10 using Intermediate 29 and 1-(4-isocyanatophenyl)-4-methylpiperazine. $^{13}$C NMR δ (75

MHz, CDCl$_3$+CD$_3$OD) 170.6 (C-4), 162.8 (C-7a), 159.1 (C-2), 157.6 (d, J$_{CF}$ 246.0 Hz, phenyl), 156.0 (C=O), 146.4 (phenyl), 131.9 (C-5), 130.6 (phenyl), 129.1 (d, J$_{CF}$ 7.5 Hz, phenyl), 128.2 (phenyl), 124.1 (d, J$_{CF}$ 14.3 Hz, phenyl), 123.6 (phenyl), 122.0 (phenyl), 117.0 (C-6), 116.4 (phenyl), 115.1 (d, J$_{CF}$ 21.3 Hz, phenyl), 110.3 (C-4a), 53.9 (NCH$_2$), 48.9 (NCH$_2$), 48.5 (NCH$_2$), 44.1 (NCH$_3$), 42.3 (NCH$_2$). MS (m/z) 547 [M+H]$^+$.

Example 57

4-[2-Amino-5-(2-fluorophenyl)thieno[2,3-c]pyrimidin-4-yl]-N-(4-methoxyphenyl)-piperazine-1-carboxamide Prepared via General Method 10 using Intermediate 29 and 4-methoxyphenyl isocyanate. $^{13}$C NMR δ (75 MHz, CDCl$_3$+CD$_3$OD) 171.9 (C-4), 163.2 (C-7a), 159.2 (C-2), 158.1 (d, J$_{CF}$ 246.9 Hz, phenyl), 155.9 (C=O), 155.5 (phenyl), 131.9 (C-5), 131.2 (phenyl), 129.6 (d, J$_{CF}$ 6.9 Hz, phenyl), 128.5 (phenyl), 124.6 (d, J$_{CF}$ 14.2 Hz, phenyl), 124.2 (phenyl), 122.6 (phenyl), 118.1 (C-6), 115.8 (d, J$_{CF}$ 20.9 Hz, phenyl), 114.1 (phenyl), 111.2 (C-4a), 55.5 (OCH$_3$), 49.4 (NCH$_2$), 43.0 (NCH$_2$). MS (m/z) 479 [M+H]$^+$.

Example 58

4-(2-Amino-6-methyl-5-phenylthieno[2,3-c]pyrimidin-4-yl)-N-[4-(dimethylamino)-phenyl]piperazine-1-carboxamide Prepared via General Method 10 using Preparative Example 11 and 4-(dimethyl-amino)phenyl isocyanate. $^{13}$C NMR δ (75 MHz, CDCl$_3$) 172.83, 165.76, 162.21, 160.20, 151.25, 139.19, 134.21, 133.78 (2C), 133.00, 131.77, 131.65 (2C), 130.97, 126.69 (2C), 117.42 (2C), 115.35, 52.87 (2C), 46.24 (2C), 44.73, 17.38. MS (m/z) 488 [M+H]$^+$.

Example 59

4-(2-Amino-6-methyl-5-phenylthieno[2,3-c]pyrimidin-4-yl)-N-(2-methoxyphenyl)-piperazine-1-carboxamide Prepared via General Method 10 using Preparative Example 11 and 2-methoxy-phenyl isocyanate. $^{13}$C NMR δ (75 MHz, acetone-d$_6$) 170.87, 162.84, 160.20, 154.99, 149.22, 136.53, 131.38, 131.02 (2C), 129.79, 128.62 (2C), 127.79, 127.29, 122.80, 121.02, 120.47, 111.73, 110.89, 56.03, 50.02 (2C), 43.30 (2C), 14.17. MS (m/z) 475 [M+H]$^+$.

Example 60

4-(2-Amino-6-methyl-5-phenylthieno[2,3-c]pyrimidin-4-yl)-N-[3-(morpholin-4-yl-methyl)phenyl]piperazine-1-carboxamide Prepared via General Method 10 using Preparative Example 11 and 4-(3-isocyanatobenzyl)morpholine. $^{13}$C NMR δ (75 MHz, CDCl$_3$) 169.86, 166.58, 158.10, 154.35, 138.58, 138.25, 135.43, 130.07, 129.95 (2C), 128.41, 128.32, 127.74 (2C), 127.05, 123.69, 120.14, 118.39, 111.78, 66.62 (2C), 63.04, 53.29 (2C), 48.94 (2C), 42.50 (2C), 14.09. MS (m/z) 544 [M+H]$^+$.

Example 61

4-(2-Amino-6-methyl-5-phenylthieno[2,3-c]pyrimidin-4-yl)-N-(3-methylphenyl)-piperazine-1-carboxamide Prepared via General Method 10 using Preparative Example 11 and 3-methyl-phenyl isocyanate. $^{13}$C NMR δ (75 MHz, CDCl$_3$) 169.76, 161.68, 158.14, 154.58, 138.49, 138.36, 135.40, 130.12, 129.94 (2C), 128.31, 128.22, 127.74 (2C), 127.06, 123.60, 120.34, 116.64, 111.75, 48.95 (2C), 42.53 (2C), 21.14, 14.10. MS (m/z) 459 [M+H]$^+$.

Example 62

4-[2-Amino-5-(4-fluorophenyl)-6-methylthieno[2,3-d]pyrimidin-4-yl]-N-[4-(4-methylpiperazin-1-yl)phenyl]piperazine-1-carboxamide Prepared via General Method 10 using Intermediate 30 and 1-(4-isocyanatophenyl)-4-methylpiperazine. $^{13}$C NMR δ (75 MHz, CDCl$_3$+CD$_3$OD) 168.8 (C-4), 161.7 (C-2), 159.9 (d, J$_{CF}$ 245.0 Hz, phenyl), 158.4 (C-7a), 156.0 (C=O), 146.6 (phenyl), 131.8 (C-5), 131.3 (d, J$_{CF}$ 7.7 Hz, phenyl), 131.2 (phenyl), 128.9 (phenyl), 127.7 (C-6), 122.0 (phenyl), 116.4 (phenyl), 114.2 (d, J$_{CF}$ 21.3 Hz, phenyl), 111.1 (C-4a), 54.1 (NCH$_2$), 48.8 (NCH$_2$), 44.5 (NCH$_3$), 42.3 (NCH$_2$). MS (m/z) 561 [M+H]$^+$.

Example 63

4-[2-Amino-5-(4-fluorophenyl)-6-methylthieno[2,3-d]pyrimidin-4-yl]-N-[4-(dimethyl-amino)phenyl]piperazine-1-carboxamide Prepared via General Method 10 using Intermediate 30 and 4-(dimethylamino)-phenyl isocyanate. MS (m/z) 506 [M+H]$^+$.

Example 64

4-[2-Amino-5-(4-fluorophenyl)-6-methylthieno[2,3-d]pyrimidin-4-yl]-N-(4-methoxy-phenyl)piperazine-1-carboxamide Prepared via General Method 10 using Intermediate 30 and 4-methoxyphenyl isocyanate. $^{13}$C NMR δ (75 MHz, CDCl$_3$+CD$_3$OD) 170.1 (C-4), 162.1 (C-7a), 160.3 (d, J$_{CF}$ 245.7 Hz, phenyl), 158.6 (C-2), 155.9 (C=O), 155.5 (phenyl), 132.0 (phenyl), 131.8 (d, J$_{CF}$ 7.9 Hz, phenyl), 129.4 (C-5), 128.7 (C-6), 122.6 (phenyl), 114.9 (d, J$_{CF}$ 21.2 Hz, phenyl), 114.1 (phenyl), 112.0 (C-4a), 55.5 (OCH$_3$), 49.3 (NCH$_2$), 43.0 (NCH$_2$), 14.4 (CH$_3$). MS (m/z) 493 [M+H]$^+$.

Example 65

4-(2-Amino-5-methylthieno[2,3-d]pyrimidin-4-yl)-N-(4-methoxy-2-methylphenyl)-piperazine-1-carboxamide Prepared via General Method 10 using Preparative Example 22 and 4-methoxy-2-methylphenyl isocyanate. $^{13}$C NMR δ (75 MHz, CDCl$_3$+CD$_3$OD) 171.1 (C-4), 164.1 (C-2), 158.8 (C-7a), 157.3 (C=O), 157.2 (phenyl), 135.7 (C-5), 129.1 (phenyl), 127.7 (phenyl), 114.9 (phenyl), 113.5 (C-6), 113.4 (C-4a), 110.8 (phenyl), 54.4 (OCH$_3$), 49.8 (NCH$_2$), 43.2 (NCH$_2$), 17.1 (CH$_3$), 14.4 (CH$_3$). MS (m/z) 413 [M+H]$^+$.

Example 66

4-(2-Amino-5-methylthieno[2,3-d]pyrimidin-4-yl)-N-(4-methoxyphenyl)piperazine-1-carboxamide Prepared via General Method 10 using Preparative Example 22 and 4-methoxy-phenyl isocyanate. MS (m/z) 399 [M+H]$^+$.

Example 67

4-(2-Amino-5-cyclohexylthieno[2,3-c]pyrimidin-4-yl)-N-(4-methoxy-2-methylphenyl)-piperazine-1-carboxamide Prepared via General Method 10 using Intermediate 31 and 4-methoxy-2-methyl-phenyl isocyanate. $^{13}$C NMR δ (75 MHz, CDCl$_3$+CD$_3$OD) 171.6 (C-4), 164.6 (C-2), 158.6 (C-7a), 157.4 (C=O), 157.1 (phenyl), 140.9 (C-5), 135.3 (phenyl), 129.4 (phenyl), 127.6 (phenyl), 115.5 (phenyl), 112.7 (C-4a), 112.2 (C-6), 111.3 (phenyl), 55.1 (OCH$_3$), 50.4 (NCH$_2$), 43.7 (NCH$_2$), 38.3 (CH), 34.5 (CH$_2$), 26.8 (CH$_2$), 25.9 (CH$_2$), 17.8 (CH$_3$). MS (m/z) 481 [M+H]$^+$.

Example 68

4-(2-Amino-5-cyclohexylthieno[2,3-d]pyrimidin-4-yl)-N-[4-(dimethylamino)phenyl]-piperazine-1-carboxamide Prepared via General Method 10 using Intermediate 31 and 4-(dimethylamino)-phenyl isocyanate. $^{13}$C NMR δ (75 MHz, CDCl$_3$) 172.4 (C-4), 164.8 (C-2), 158.8 (C-7a), 156.3 (C=O), 141.1 (C-5), 123.1 (phenyl), 113.4 (C-4a), 113.2 (C-6), 112.5 (phenyl), 50.6 (NCH$_2$), 43.9 (NCH$_2$), 41.1 (NCH$_3$), 38.5 (CH), 34.7 (CH$_2$), 27.1 (CH$_2$), 26.2 (CH$_2$). MS (m/z) 480 [M+H]$^+$.

Example 69

4-(2-Amino-5-cyclohexylthieno[2,3-d]pyrimidin-4-yl)-N-(4-methoxyphenyl)piperazine-1-carboxamide Prepared via General Method 10 using Intermediate 31 and 4-methoxyphenyl isocyanate. $^{13}$C NMR δ (75 MHz, CDCl$_3$+CD$_3$OD) 171.6 (C-4), 164.6 (C-2), 158.6 (C-7a), 156.4 (C=O), 155.8 (phenyl), 140.9 (C-5), 131.9 (phenyl), 122.9 (phenyl), 113.8 (phenyl), 112.8 (C-4a), 112.3 (C-6), 55.3 (OCH$_3$), 50.4 (NCH$_2$), 43.6 (NCH$_2$), 38.3 (CH), 34.5 (CH$_2$), 26.8 (CH$_2$), 25.9 (CH$_2$). MS (m/z) 467 [M+H]$^+$.

Example 70

4-[2-Amino-5-(3-chloropropyl)thieno[2,3-d]pyrimidin-4-yl]-N-(4-methoxy-2-methyl-phenyl)piperazine-1-carboxamide Prepared via General Method 10 using Intermediate 32 and 4-methoxy-2-methyl-phenyl isocyanate. $^{13}$C NMR δ (75 MHz, CDCl$_3$) 172.6 (C-4), 164.6 (C-2), 159.1 (C-7a), 157.2 (C=O), 156.5 (phenyl), 134.1 (C-5), 133.1 (phenyl), 129.7 (phenyl), 126.8 (phenyl), 115.9 (phenyl), 114.7 (C-6), 113.5 (C-4a), 111.6 (phenyl), 55.4 (OCH$_3$), 50.5 (NCH$_2$), 44.6 (CH$_2$Cl), 43.8 (NCH$_2$), 32.8 (CH$_2$), 28.1 (CH$_2$), 18.2 (CH$_3$). MS (m/z) 476 [M+H]$^+$.

Example 71

4-[2-Amino-5-(3-chloropropyl)thieno[2,3-d]pyrimidin-4-yl]-N-(4-methoxyphenyl)-piperazine-1-carboxamide Prepared via General Method 10 using Intermediate 32 and 4-methoxyphenyl isocyanate. $^{13}$C NMR δ (75 MHz, CDCl$_3$) 172.7 (C-4), 164.6 (C-2), 159.1 (C-7a), 156.1 (C=O), 155.9 (phenyl), 133.0 (C-5), 131.9 (phenyl), 122.9 (phenyl), 114.7 (C-6), 114.2 (phenyl), 113.6 (C-4a), 55.5 (OCH$_3$), 50.5 (NCH$_2$), 44.6 (CH$_2$Cl), 43.7 (NCH$_2$), 32.8 (CH$_2$), 28.1 (CH$_2$). MS (m/z) 461 [M+H]$^+$.

Example 72

4-(2-Aminothieno[2,3-d]pyrimidin-4-yl)-N-[4-(dimethylamino)phenyl]piperazine-1-carboxamide Prepared via General Method 10 using Intermediate 33 and 4-(dimethylamino)-phenyl isocyanate. $^{13}$C NMR δ (75 MHz, CDCl$_3$) 174.41, 162.96, 162.87, 160.35, 151.42, 132.54, 126.92 (2C), 124.29 (2C), 119.88, 117.34, 113.80, 49.64 (2C), 46.67 (2C), 44.78 (2C). MS (m/z) 398 [M+H]$^+$.

Example 73

4-[2-Amino-5-(ethoxycarbonyl)thieno[2,3-d]pyrimidin-4-yl]-N-[4-(dimethylamino)-phenyl]piperazine-1-carboxamide Prepared via General Method 10 using Preparative Example 20 and 4-(dimethyl-amino)phenyl isocyanate. $^{13}$C NMR δ (75 MHz, CDCl$_3$) 175.33, 166.66, 164.53, 162.85, 160.27, 151.40, 132.67, 131.07, 129.28, 126.70 (2C), 117.31 (2C), 111.00, 65.09, 51.74 (2C), 47.02 (2C), 44.78 (2C), 17.74. MS (m/z) 470 [M+H]$^+$.

Example 74

4-[2-Amino-5-(ethoxycarbonyl)thieno[2,3-d]pyrimidin-4-yl]-N-(2,4-difluorophenyl)-piperazine-1-carboxamide Prepared via General Method 10 using Preparative Example 20 and 2,4-difluorophenyl isocyanate. $^{13}$C NMR δ (75 MHz, CDCl$_3$) 171.53, 162.56, 160.57, 158.79, 158.35 (dd, J$_{CF}$ 243.7, 11.2 Hz), 154.81, 153.59 (dd, J$_{CF}$ 243.7, 11.2 Hz), 127.00, 125.63, 124.24 (t, J$_{CF}$ 11.3 Hz), (d, J$_{CF}$ 9.0 Hz), 122.76 (dd, J$_{CF}$ 21.5, 3.7 Hz), 110.63 (dd, J$_{CF}$ 21.7, 3.7 Hz), 107.16, 103.19 (t, J$_{CF}$ 24.0 Hz), 61.11, 47.66 (2C), 43.09 (2C), 13.82. MS (m/z) 463 [M+H]$^+$.

Example 75

Ethyl 2-amino-4-{4-[4-(4-methylpiperazin-1-yl)phenylcarbamoyl]piperazin-1-yl}thieno[2,3-d]pyrimidine-5-carboxylate Prepared via General Method 10 using Preparative Example 20 and 1-(4-isocyanatophenyl)-4-methylpiperazine. $^{13}$C NMR δ (75 MHz, CDCl$_3$) 171.72, 162.98, 160.87, 159.19, 156.29, 147.33, 131.87, 127.40, 125.67, 122.23 (2C), 116.93 (2C), 107.36, 61.44, 54.79 (2C), 49.50 (2C), 48.09 (2C), 45.66, 43.38 (2C), 14.11. MS (m/z) 525 [M+H]$^+$.

Example 76

4-[2-Amino-5-(ethoxycarbonyl)thieno[2,3-d]pyrimidin-4-yl]-N-(2,4-dimethoxyphenyl)-piperazine-1-carboxamide Prepared via General Method 10 using Preparative Example 20 and 2,4-dimethoxyphenyl isocyanate. $^{13}$C NMR δ (75 MHz, CDCl$_3$) 171.91, 162.52, 160.59, 158.84, 155.32, 154.69, 148.92, 127.20, 125.41, 121.61, 120.18, 107.27, 103.67, 98.28, 61.01, 55.43, 55.21, 47.79 (2C), 43.08 (2C), 13.99. MS (m/z) 487 [M+H]$^+$.

Example 77

4-[2-Amino-5-(ethoxycarbonyl)thieno[2,3-d]pyrimidin-4-yl]-N-(4-methoxy-2-methyl-phenyl)piperazine-1-carboxamide Prepared via General Method 10 using Preparative Example 20 and 4-methoxy-2-methylphenyl isocyanate. $δ_H$ (DMSO-d$_6$, 400 MHz) 8.00 (1H, br s), 7.78 (1H, s), 7.03 (1H, d, J 8.6 Hz), 6.77 (1H, m), 6.69 (1H, dd, J 8.4, 2.9 Hz), 6.51 (2H, br s), 4.29 (2H, q, J 7.1 Hz), 3.72 (3H, s), 3.54-3.44 (8H, br m), 2.13 (3H, s), 1.31 (3H, t, J 7.1 Hz). LCMS (pH 10) RT 1.90 minutes; MS (m/z) 471 [M+H]$^+$.

Example 78

4-[2-Amino-5-(hydroxymethyl)thieno[2,3-d]pyrimidin-4-yl]-N-[4-(dimethylamino)-phenyl]piperazine-1-carboxamide To a solution of Intermediate 36 (100 mg, 0.27 mmol) in dichloromethane (4 mL) was added trifluoroacetic acid (4 mL) at 0° C. The reaction mixture was stirred at room temperature for 30 minutes, after which time the solvents were evaporated in vacuo. The residue was dissolved in tetrahydrofuran (4 mL), then diisopropylamine (924 μL, 5.4 mmol) was added, followed by 4-(dimethylamino)phenyl isocyanate (48 mg, 0.28 mmol). The solution was stirred at room temperature overnight. The solvents were evaporated in vacuo and the crude residue was purified by flash chromatography, the mobile phase being a mixture of methanol and dichloromethane (in a ratio gradually increasing from 1% to 3% methanol in dichloromethane), yielding the title compound (43 mg). $^{13}$C NMR δ (75 MHz, CDCl$_3$) 171.67, 164.14, 159.15, 156.91, 147.49, 134.04, 129.08, 122.97 (2C), 115.68, 113.46 (2C), 112.44, 59.10, 49.82 (2C), 43.22 (2C), 40.58 (2C). MS (m/z) 428 [M+H]$^+$.

Example 79

Ethyl 2-amino-4-{4-[4-(dimethylamino)phenylcarbamoyl]piperazin-1-yl}thieno[2,3-d]-pyrimidin-5-ylcarbamate To a solution of Intermediate 37 (60 mg, 0.14 mmol) in dichloromethane (1 mL) was added trifluoroacetic acid (1 mL) at room temperature. The reaction mixture was stirred at room temperature for 30 minutes, after which time the solvents were evaporated in vacuo. The residue was dissolved in dichloromethane (2 mL), then diisopropylamine (486 μL, 2.8 mmol) was added, followed by 4-(dimethylamino)phenyl isocyanate (24 mg, 0.15 mmol). The solution was stirred at room temperature overnight. The solvents were evaporated in vacuo and the crude residue was purified by flash chromatography, the mobile phase being a mixture of methanol and dichloromethane (in a ratio gradually increasing from 1% to 3% methanol in dichloromethane), yielding the title compound (56 mg). $^{13}$C NMR δ (75 MHz, CDCl$_3$) 168.80, 163.69, 159.80, 156.81, 153.84, 147.50, 129.01, 126.79, 123.00 (2C), 113.29 (2C), 107.52, 100.98, 61.15, 49.98 (2C), 43.19 (2C), 40.36 (2C), 13.67. MS (m/z) 485 [M+H]$^+$.

Example 80

2-Amino-4-[4-(4-methoxy-2-methylphenylcarbamoyl)piperazin-1-yl]thieno[2,3-c]-pyrimidine-5-carboxylic acid (2-hydroxy-1,1-dimethylethyl)amide To a solution of Intermediate 38 (0.2 g, 0.45 mmol) in DMF (15 mL) were added 2-amino-2-methylpropan-1-ol (68 μL, 1.13 mmol), HOBT (76 mg, 0.50 mmol), EDC (95 mg, 0.50 mmol) and DIPEA (313 μL, 1.80 mmol). The reaction mixture was stirred at room temperature overnight, then concentrated in vacuo. The crude material was purified by column chromatography, eluting with 0-10% MeOH/EtOAc, to give the title compound (135 mg) as a white solid. $δ_H$ (DMSO-d$_6$, 400 MHz) 8.00 (1H, s), 7.67 (1H, s), 7.36 (1H, s), 7.03 (1H, d, J 8.6 Hz), 6.77 (1H, m), 6.69 (1H, dd, J 8.6, 2.9 Hz), 6.40 (2H, br s), 4.89 (1H, t, J 5.8 Hz), 3.72 (3H, s), 3.48 (8H, br m), 3.31 (6H, s), 2.12 (2H, s), 1.31 (3H, s). LCMS (pH 10) RT 1.28 minutes; MS (m/z) 514 [M+H]$^+$.

Example 81

4-[2-Amino-5-(trifluoromethyl)thieno[2,3-d]pyrimidin-4-yl]piperazine-1-carboxylic acid (4-methoxyphenyl)amide Prepared via General Method 10 using 4-methoxyphenyl isocyanate (0.06 mL, 0.44 mmol) and Intermediate 43 (248 mg, 0.41 mmol). The title compound (155 mg) was isolated as a white powder. $δ_H$ (DMSO-d$_6$, 400 MHz) 8.43 (1H, s), 7.98 (1H, s), 7.37-7.33 (2H, m), 6.85-6.81 (2H, m), 6.82 (2H, s), 3.71 (3H, s), 3.57-3.54 (4H, m), 3.24-3.21 (4H, m). LCMS (pH 10) RT 2.09 minutes; MS (m/z) 453.6 [M+H]$^+$.

Example 82

4-[2-Amino-5-(trifluoromethyl)thieno[2,3-d]pyrimidin-4-yl]piperazine-1-carboxylic acid (4-methoxy-2-methylphenyl)amide Prepared via General Method 10 using 4-methoxy-2-methylphenyl isocyanate (0.07 mL, 0.44 mmol) and Intermediate 43 (248 mg, 0.41 mmol). The title compound (33 mg) was isolated as a white powder. $δ_H$ (DMSO-d$_6$, 400 MHz) 8.02 (1H, s), 7.98 (1H, s), 7.05 (1H, d, J 8.4 Hz), 6.82 (2H, s), 6.78 (1H, d, J 2.8 Hz), 4.71 (1H, dd, J 8.6, 2.9 Hz), 3.72 (3H, s), 3.56-3.54 (4H, m), 3.24-3.21 (4H, m), 2.14 (3H, s). LCMS (pH 10) RT 2.14 minutes; MS (m/z) 467.6 [M+H]$^+$.

Example 83

General Method 11

2-Amino-4-[4-(4-methoxyphenylcarbamoyl)piperazin-1-yl]isothiazolo[5,4-d]pyrimidine To a solution of Intermediate 48 (46 mg, 0.19 mmol) in DMF (2 mL) was added 4-methoxyphenyl isocyanate (25 μL, 0.19 mmol), and the reaction mixture was stirred at room temperature for 1 hour. The reaction mixture was concentrated and purified by silica gel chromatography, eluting with DCM/MeOH (30:1), to provide the title compound (73 mg, 0.18 mmol) as a white solid. $^{13}$C NMR δ (DMSO-d$_6$, 125 MHz) 183.6 (C-7a), 161.0 (C-2), 158.7 (C-4), 155.3 (C=O), 154.6 (phenyl), 153.9 (C-5), 133.4 (phenyl), 121.8 (phenyl), 113.6 (phenyl), 108.0 (C-4a), 55.2 (OCH$_3$), 45.3 (NCH$_2$), 42.8 (NCH$_2$). MS (m/z) 386 [M+H]$^+$.

Example 84

2-Amino-4-[4-(4-methoxy-2-methylphenylcarbamoyl)piperazin-1-yl]isothiazolo[5,4-d]-pyrimidine Prepared via General Method 11 from Intermediate 48 (46 mg, 0.19 mmol) and 4-methoxy-2-methylphenyl isocyanate (26 μL, 0.19 mmol). The title compound (68 mg, 0.17 mmol) was obtained as a white solid. $^{13}$C NMR δ (DMSO-d$_6$, 125 MHz) 183.6 (C-7a), 161.0 (C-2), 158.7 (C-4), 156.7 (C=O), 156.0 (phenyl), 154.0 (C-5), 135.4 (phenyl), 130.6 (phenyl), 128.0 (phenyl), 115.2 (phenyl), 111.1 (phenyl), 108.0 (C-4a), 55.2 (OCH$_3$), 45.3 (NCH$_2$), 42.9 (NCH$_2$), 18.2 (CH$_3$). MS (m/z) 400 [M+H]$^+$.

Example 85

2-Amino-4-[4-(4-methoxyphenylcarbamoyl)-2-(S)-methylpiperazin-1-yl]isothiazolo[5,4-d]pyrimidine Prepared via General Method 11 from Intermediate 49 (59 mg, 0.23 mmol) and 4-methoxyphenyl isocyanate (31 μL, 0.23 mmol). The title compound (85 mg, 0.21 mmol) was obtained as a white solid. $^{13}$C NMR δ (DMSO-d$_6$, 125 MHz) 183.7 (C-7a), 161.0 (C-2), 158.3 (C-4), 155.7 (C=O), 154.6 (phenyl), 153.8 (C-5), 133.4 (phenyl), 121.8 (phenyl), 113.6 (phenyl), 107.7 (C-4a), 55.2 (OCH$_3$), 47.0 (NCH$_2$), 43.1 (NCH$_2$), 15.9 (CH$_3$). MS (m/z) 400 [M+H]$^+$.

Example 86

2-Amino-4-[4-(4-methoxy-2-methylphenylcarbamoyl)-2-(S)-methylpiperazin-1-yl]-isothiazolo[5,4-d]pyrimidine Prepared via General Method 11 from Intermediate 49 (59 mg, 0.23 mmol) and 4-methoxy-2-methylphenyl isocyanate (32 μL, 0.23 mmol). The title compound (93 mg, 0.22 mmol) was obtained as a white solid. $^{13}$C NMR δ (DMSO-d$_6$, 125 MHz) 183.7 (C-7a), 161.1 (C-2), 158.4 (C-4), 156.7 (C=O), 156.2 (phenyl), 153.8 (C-5), 135.6 (phenyl), 130.7 (phenyl), 128.1 (phenyl), 115.2 (phenyl), 111.1 (phenyl), 107.7 (C-4a), 55.2 (OCH$_3$), 47.1 (NCH$_2$), 43.1 (NCH$_2$), 18.1 (CH$_3$), 15.8 (CH$_3$). MS (m/z) 414 [M+H]$^+$.

Example 87

4-(2-Amino-5-cyanothieno[2,3-d]pyrimidin-4-yl)piperazine-1-carboxylic acid (4-methoxyphenyl)amide Prepared via General Method 10 from Intermediate 52 (45 mg, 0.15 mmol) and 4-methoxyphenyl isocyanate (19.3 μL, 0.15 mmol). The title compound (12 mg) was isolated as a white solid after purification by preparative HPLC. δ$_H$ (DMSO-d$_6$, 400 MHz) 8.47 (1H, s), 8.29 (1H, s), 7.36 (2H, m), 6.79 (4H, m), 3.71 (3H, s), 3.65-3.63 (4H, br m), 3.47-3.44 (4H, br m). MS (m/z) 410 [M+H]$^+$.

Example 88

4-(2-Amino-5-oxo-5,6-dihydrothieno[2,3-d]pyrimidin-4-yl)piperazine-1-carboxylic acid (4-methoxy-2-methylphenyl)amide Prepared via General Method 10 from Intermediate 54 (180 mg, 0.63 mmol) and 4-methoxy-2-methylphenyl isocyanate (96 μL). The title compound (80 mg) was isolated (via precipitation during work-up with DCM and brine) as a yellow solid. δ$_H$ (DMSO-d$_6$, 400 MHz) 8.00 (1H, s), 7.33 (2H, br s), 7.05 (1H, m), 6.77 (1H, m), 6.69 (1H, m), 3.72 (5H, br m), 3.67 (4H, br m), 3.53 (4H, br m), 2.14 (3H, s). MS (m/z) 415 [M+H]$^+$.

General Method 12

To a solution of the appropriate carboxylic acid (1.2 eq.) in DMF (2 mL) maintained at 0° C. were added HATU (1.5 eq.) and DIPEA (2 eq.). To the reaction mixture was added the appropriate 4-(piperazin-1-yl)thieno[2,3-c]pyrimidine or 4-(2,5-diazabicyclo[2.2.1]heptan-2-yl)thieno[2,3-d]pyrimidine derivative (1 eq.) and the reaction mixture was stirred at room temperature for 12 h. The reaction mixture was then diluted with water and extracted with EtOAc. The organic layer was washed with water and brine, then dried over sodium sulphate. The organic layer was concentrated under vacuum and the crude residue was purified by column chromatography (silica gel 100-200 mesh, MeOH:DCM 1:9) to afford the title compound.

General Method 13

To a stirred solution of the appropriate 4-(piperazin-1-yl)thieno[2,3-d]pyrimidine derivative (1 eq.) in DMF (2 mL) maintained at 0° C. was added Cs$_2$CO$_3$ (2.5 eq.) followed by the appropriate alkyl halide (1.2 eq.). The reaction mixture was stirred at room temperature for 12 h. The reaction mixture was then diluted with water and extracted with EtOAc. The organic layer was washed with water and brine, then concentrated under vacuum. The crude residue was purified by column chromatography (silica gel 100-200 mesh, MeOH:DCM 1:9) to afford the title compound.

General Method 14

To a stirred solution of the appropriate 4-(piperazin-1-yl)thieno[2,3-d]pyrimidine derivative (1 eq.) in DCM (2 mL) was added triethylamine (3 eq.), followed by the appropriate alkyl halide (1.2 eq.). The reaction mixture was stirred at room temperature for 12 h. The reaction mixture was then diluted with water and extracted with EtOAc. The organic layer was washed with water and brine, then concentrated under vacuum. The crude residue was purified by column chromatography (silica gel 100-200 mesh, MeOH:DCM 1:9) to afford the title compound.

General Method 15

To a stirred solution of the appropriate 4-(piperazin-1-yl)thieno[2,3-d]pyrimidine derivative (1 eq.) in MeOH (2 mL) were added triethylamine (3 eq.) and the appropriate aldehyde (1.2 eq.). The reaction mixture was stirred for 30 minutes at room temperature. The reaction mixture was then cooled to 0° C. and NaBH$_4$ (1.7 eq.) was added. The reaction mixture was stirred for 2 h at room temperature. The reaction mixture was then quenched with saturated aqueous NH$_4$Cl solution and extracted with DCM. The organic layer was washed with water and brine, then concentrated under vacuum. The crude residue was purified by column chromatography (silica gel 100-200 mesh, MeOH:DCM 1:9) to afford the title compound.

General Method 16

To a solution of the appropriate 4-(piperazin-1-yl)thieno [2,3-d]pyrimidine or 4-(2,5-diazabicyclo[2.2.1]heptan-2-yl) thieno[2,3-d]pyrimidine derivative (1 eq.) in DMF (2 mL) was added DIPEA (3 eq.), followed by addition of the appropriate isocyanate (1.1 eq.). The reaction mixture was stirred at r.t. for 1 h. The reaction mixture was then concentrated, extracted with ethyl acetate and purified by column chromatography (silica gel 100-200 mesh, 3% MeOH in DCM), to afford the title compound.

Examples 89 to 155

The following compounds were prepared from Preparative Example 20 via the indicated General Method.

| Example | Compound Name | General Method | LCMS RT | (M$^+$) |
|---|---|---|---|---|
| 89 | Ethyl 2-amino-4-{4-[(3-chloro-4-methoxyphenyl)-carbamoyl]piperazin-1-yl}thieno[2,3-d]pyrimidine-5-carboxylate | 16 | 2.33 | 491.3 |
| 90 | Ethyl 2-amino-4-{4-[(4-ethoxyphenyl)carbamoyl]-piperazin-1-yl}thieno[2,3-d]pyrimidine-5-carboxylate | 16 | 2.13 | 471.3 |
| 91 | Ethyl 2-amino-4-[4-(o-tolylcarbamoyl)piperazin-1-yl]thieno[2,3-d]pyrimidine-5-carboxylate | 16 | 2.09 | 441.2 |
| 92 | Ethyl 2-amino-4-[4-(m-tolylcarbamoyl)piperazin-1-yl]thieno[2,3-d]pyrimidine-5-carboxylate | 16 | 2.32 | 441.3 |
| 93 | Ethyl 2-amino-4-[4-(benzo[d][1,3]dioxol-5-yl-carbamoyl)piperazin-1-yl]thieno[2,3-d]pyrimidine-5-carboxylate | 16 | 2.12 | 471.3 |
| 94 | Ethyl 2-amino-4-(4-{[4-(trifluoromethoxy)phenyl]-carbamoyl}piperazin-1-yl)thieno[2,3-d]pyrimidine-5-carboxylate | 16 | 2.58 | 511.3 |
| 95 | Ethyl 2-amino-4-(4-{[4-(difluoromethoxy)phenyl]-carbamoyl}piperazin-1-yl)thieno[2,3-d]pyrimidine-5-carboxylate | 16 | 2.24 | 493.3 |
| 96 | Ethyl 2-amino-4-[4-(phenylcarbamoyl)piperazin-1-yl]thieno[2,3-d]pyrimidine-5-carboxylate | 16 | 2.08 | 427.2 |
| 97 | Ethyl 2-amino-4-(4-{2-[4-(dimethylamino)phenyl]-acetyl}piperazin-1-yl)thieno[2,3-d]pyrimidine-5-carboxylate | 12 | 2.19 | 469.3 |
| 98 | Ethyl 2-amino-4-[4-(benzylcarbamoyl)piperazin-1-yl]thieno[2,3-d]pyrimidine-5-carboxylate | 16 | 2.15 | 441.3 |
| 99 | Ethyl 2-amino-4-{4-[2-(pyridin-4-yl)acetyl]-piperazin-1-yl}thieno[2,3-d]pyrimidine-5-carboxylate | 12 | 1.66 | 427.3 |
| 100 | Ethyl 2-amino-4-[4-(pyridin-3-ylmethyl)piperazin-1-yl]thieno[2,3-d]pyrimidine-5-carboxylate | 13 | 1.93 | 399.3 |
| 101 | Ethyl 2-amino-4-{4-[(4-methoxybenzyl)-carbamoyl]piperazin-1-yl}thieno[2,3-d]pyrimidine-5-carboxylate | 16 | 2.13 | 471.2 |
| 102 | Ethyl 2-amino-4-[4-(5-methyl-1H-pyrazole-3-carbonyl)piperazin-1-yl]thieno[2,3-d]pyrimidine-5-carboxylate | 12 | 1.95 | 416.3 |
| 103 | Ethyl 2-amino-4-[4-(2-phenoxyacetyl)piperazin-1-yl]thieno[2,3-d]pyrimidine-5-carboxylate | 12 | 2.15 | 442.3 |
| 104 | Ethyl 2-amino-4-[4-(imidazo[1,2-a]pyridine-2-carbonyl)piperazin-1-yl]thieno[2,3-d]pyrimidine-5-carboxylate | 12 | 1.91 | 452.3 |
| 105 | Ethyl 2-amino-4-[4-(pyridin-2-ylmethyl)piperazin-1-yl]thieno[2,3-d]pyrimidine-5-carboxylate | 13 | 1.93 | 399.3 |
| 106 | Ethyl 2-amino-4-(4-nicotinoylpiperazin-1-yl)-thieno[2,3-d]pyrimidine-5-carboxylate | 12 | 1.67 | 413.4 |
| 107 | Ethyl 2-amino-4-{4-[2-(3,4-dimethoxyphenyl)-acetyl]piperazin-1-yl}thieno[2,3-d]pyrimidine-5-carboxylate | 12 | 2.11 | 486.4 |
| 108 | (S)-Ethyl 2-amino-4-[4-(1,2,3,4-tetrahydro-isoquinoline-3-carbonyl)piperazin-1-yl]thieno[2,3-d]pyrimidine-5-carboxylate | 12 | 2.20 | 467.3 |
| 109 | Ethyl 2-amino-4-[4-(1-methyl-1H-imidazole-5-carbonyl)piperazin-1-yl]thieno[2,3-d]pyrimidine-5-carboxylate | 12 | 1.72 | 416.2 |
| 110 | Ethyl 4-[4-(1H-indazole-3-carbonyl)piperazin-1-yl]-2-aminothieno[2,3-d]pyrimidine-5-carboxylate | 12 | 2.14 | 452.3 |
| 111 | Ethyl 2-amino-4-{4-[6-(hydroxymethyl)picolinoyl]-piperazin-1-yl}thieno[2,3-d]pyrimidine-5-carboxylate | 12 | 1.72 | 443.3 |

-continued

| Example | Compound Name | General Method | LCMS RT | (M+) |
|---|---|---|---|---|
| 112 | Ethyl 2-amino-4-[4-(quinoxaline-2-carbonyl)-piperazin-1-yl]thieno[2,3-d]pyrimidine-5-carboxylate | 12 | 2.40 | 464.4 |
| 113 | Ethyl 2-amino-4-[4-(isoquinoline-3-carbonyl)-piperazin-1-yl]thieno[2,3-d]pyrimidine-5-carboxylate | 12 | 2.18 | 463.3 |
| 114 | Ethyl 2-amino-4-{4-[3-(2-methyl-1H-imidazol-1-yl)propanoyl]piperazin-1-yl}thieno[2,3-d]-pyrimidine-5-carboxylate | 12 | 1.68 | 444.3 |
| 115 | Ethyl 2-amino-4-{4-[1-(tert-butoxycarbonyl)-piperidine-4-carbonyl]piperazin-1-yl}thieno[2,3-d-pyrimidine-5-carboxylate | 12 | 2.33 | 519.4 |
| 116 | Ethyl 2-amino-4-{4-[(1-phenylethyl)carbamoyl]-piperazin-1-yl}thieno[2,3-d]pyrimidine-5-carboxylate | 16 | 2.18 | 455.2 |
| 117 | rac-(R)-Ethyl 2-amino-4-[4-(3-hydroxy-3-phenyl-propanoyl)piperazin-1-yl]thieno[2,3-d]pyrimidine-5-carboxylate | 12 | 2.14 | 456.3 |
| 118 | Ethyl 4-[4-(1H-pyrazole-3-carbonyl)piperazin-1-yl]-2-aminothieno[2,3-d]pyrimidine-5-carboxylate | 12 | 2.06 | 402.3 |
| 119 | Ethyl 2-amino-4-{4-[2-(morpholin-4-yl)acetyl]-piperazin-1-yl}thieno[2,3-d]pyrimidine-5-carboxylate | 12 | 1.78 | 435.3 |
| 120 | Ethyl 2-amino-4-[4-(1-methyl-1H-imidazole-2-carbonyl)piperazin-1-yl]thieno[2,3-d]pyrimidine-5-carboxylate | 12 | 1.81 | 416.2 |
| 121 | Ethyl 2-amino-4-{4-[2-(thien-3-yl)acetyl]piperazin-1-yl}thieno[2,3-d]pyrimidine-5-carboxylate | 12 | 2.18 | 432.3 |
| 122 | Ethyl 2-amino-4-[4-(pyrazine-2-carbonyl)piperazin-1-yl]thieno[2,3-d]pyrimidine-5-carboxylate | 12 | 1.79 | 414.3 |
| 123 | Ethyl 2-amino-4-(4-picolinoylpiperazin-1-yl)-thieno[2,3-d]pyrimidine-5-carboxylate | 12 | 1.85 | 413.3 |
| 124 | Ethyl 2-amino-4-{4-[3-(pyridin-3-yl)propanoyl]-piperazin-1-yl}thieno[2,3-d]pyrimidine-5-carboxylate | 12 | 1.92 | 441.3 |
| 125 | Ethyl 2-amino-4-(4-benzylpiperazin-1-yl)-thieno[2,3-d]pyrimidine-5-carboxylate | 14 | 2.30 | 398.2 |
| 126 | Ethyl 2-amino-4-[4-(imidazo[1,2-a]pyridine-3-carbonyl)piperazin-1-yl]thieno[2,3-d]pyrimidine-5-carboxylate | 12 | 1.92 | 452.3 |
| 127 | Ethyl 2-amino-4-{4-[3-(morpholin-4-yl)propanoyl]-piperazin-1-yl}thieno[2,3-d]pyrimidine-5-carboxylate | 12 | 1.75 | 449.3 |
| 128 | Ethyl 2-amino-4-{4-[3-(4-methoxyphenyl)-propanoyl]piperazin-1-yl}thieno[2,3-d]pyrimidine-5-carboxylate | 12 | 2.16 | 470.3 |
| 129 | Ethyl 2-amino-4-{4-[3-(3-methoxyphenyl)-propanoyl]piperazin-1-yl}thieno[2,3-d]pyrimidine-5-carboxylate | 12 | 2.18 | 470.3 |
| 130 | Ethyl 4-{4-[3-(1H-benzo[d]imidazol-2-yl)-propanoyl]piperazin-1-yl}-2-aminothieno[2,3-d]-pyrimidine-5-carboxylate | 12 | 1.88 | 480.3 |
| 131 | Ethyl 2-amino-4-[4-(2-phenylethyl)piperazin-1-yl]-thieno[2,3-d]pyrimidine-5-carboxylate | 13 | 2.35 | 412.2 |
| 132 | Ethyl 2-amino-4-{4-[3-(2-methoxyphenyl)-propanoyl]piperazin-1-yl}thieno[2,3-d]pyrimidine-5-carboxylate | 12 | 2.25 | 470.3 |
| 133 | Ethyl 2-amino-4-[4-(1,2,3,4-tetrahydronaphthalene-2-carbonyl)piperazin-1-yl]thieno[2,3-d]pyrimidine-5-carboxylate | 12 | 2.42 | 466.3 |
| 134 | Ethyl 2-amino-4-{4-[3-(furan-2-yl)propanoyl]-piperazin-1-yl}thieno[2,3-d]pyrimidine-5-carboxylate | 12 | 2.12 | 430.3 |
| 135 | Ethyl 2-amino-4-(4-benzoylpiperazin-1-yl)-thieno[2,3-d]pyrimidine-5-carboxylate | 12 | 2.04 | 412.4 |
| 136 | Ethyl 2-amino-4-[4-(3-cyclopentylpropanoyl)-piperazin-1-yl]thieno[2,3-d]pyrimidine-5-carboxylate | 12 | 2.47 | 432.3 |
| 137 | Ethyl 2-amino-4-[4-(isoquinoline-1-carbonyl)-piperazin-1-yl]thieno[2,3-d]pyrimidine-5-carboxylate | 12 | 2.11 | 463.3 |
| 138 | Ethyl 2-amino-4-{4-[3-(3-chloro-4-methoxy-phenyl)propanoyl]piperazin-1-yl}thieno[2,3-d]-pyrimidine-5-carboxylate | 12 | 2.53 | 504.4 |

|       |                                                                                                                              | General | LCMS |       |
| ----- | ---------------------------------------------------------------------------------------------------------------------------- | ------- | ---- | ----- |
| Example | Compound Name                                                                                                              | Method  | RT   | (M+)  |
| 139 | Ethyl 2-amino-4-[4-(quinoline-2-carbonyl)-piperazin-1-yl]thieno[2,3-d]pyrimidine-5-carboxylate | 12 | 2.33 | 463.4 |
| 140 | Ethyl 2-amino-4-{4-[3-(4-fluorophenyl)propanoyl]-piperazin-1-yl}thieno[2,3-d]pyrimidine-5-carboxylate | 12 | 2.48 | 458.3 |
| 141 | Ethyl 2-amino-4-{4-[3-(p-tolyl)propanoyl]-piperazin-1-yl}thieno[2,3-d]pyrimidine-5-carboxylate | 12 | 2.51 | 454.4 |
| 142 | Ethyl 4-[4-(1H-benzo[d]imidazole-2-carbonyl)-piperazin-1-yl]-2-aminothieno[2,3-d]pyrimidine-5-carboxylate | 12 | 2.22 | 452.3 |
| 143 | Ethyl 2-amino-4-{4-[3-(4-methylpiperazin-1-yl)-propanoyl]piperazin-1-yl}thieno[2,3-d]pyrimidine-5-carboxylate | 12 | 1.68 | 462.4 |
| 144 | Ethyl 2-amino-4-{4-[2-(dimethylamino)acetyl]-piperazin-1-yl}thieno[2,3-d]pyrimidine-5-carboxylate | 12 | 1.64 | 393.2 |
| 145 | Ethyl 2-amino-4-{4-[3-(o-tolyl)propanoyl]-piperazin-1-yl}thieno[2,3-d]pyrimidine-5-carboxylate | 12 | 2.40 | 454.3 |
| 146 | Ethyl 4-[4-(1H-indole-2-carbonyl)piperazin-1-yl]-2-aminothieno[2,3-d]pyrimidine-5-carboxylate | 12 | 2.57 | 451.4 |
| 147 | (S)-Ethyl 2-amino-4-{4-[2-(methylamino)-2-phenylacetyl]piperazin-1-yl}thieno[2,3-d-pyrimidine-5-carboxylate | 12 | 1.97 | 455.3 |
| 148 | Ethyl 2-amino-4-{4-[1-(4-methoxyphenyl)-cyclopropanecarbonyl]piperazin-1-yl}thieno[2,3-d]pyrimidine-5-carboxylate | 12 | 2.27 | 482.3 |
| 149 | Ethyl 2-amino-4-[4-(2-methyl-3-phenylpropanoyl)-piperazin-1-yl]thieno[2,3-d]pyrimidine-5-carboxylate | 12 | 2.54 | 454.3 |
| 150 | Ethyl 2-amino-4-[4-(2-phenylcyclopropane-carbonyl)piperazin-1-yl]thieno[2,3-d]pyrimidine-5-carboxylate | 12 | 2.56 | 452.3 |
| 151 | Ethyl 2-amino-4-[4-(3-phenylbutyl)piperazin-1-yl]-thieno[2,3-d]pyrimidine-5-carboxylate | 15 | 2.84 | 440.5 |
| 152 | (S)-Ethyl 2-amino-4-[4-(1-methylpyrrolidine-2-carbonyl)piperazin-1-yl]thieno[2,3-d]pyrimidine-5-carboxylate | 12 | 1.72 | 419.3 |
| 153 | Ethyl 4-{4-[3-(1H-indol-3-yl)propanoyl]piperazin-1-yl}-2-aminothieno[2,3-d]pyrimidine-5-carboxylate | 12 | 2.15 | 479.4 |
| 154 | Ethyl 2-amino-4-[4-(3-phenylpropanoyl)piperazin-1-yl]thieno[2,3-d]pyrimidine-5-carboxylate | 12 | 2.22 | 440.3 |
| 155 | Ethyl 2-amino-4-[4-(3-phenylpropyl)piperazin-1-yl]thieno[2,3-d]pyrimidine-5-carboxylate | 13 | 2.71 | 426.3 |

Examples 156 to 175

The following compounds were prepared by a three-step procedure comprising: (i) reaction of Intermediate 13 with the appropriate BOC-protected diamine derivative via General Method 4; (ii) removal of the BOC protecting group via General Method 8; and (iii) coupling of the amine resulting from step (ii) with the appropriate carboxylic acid utilising General Method 12; or coupling of the amine resulting from step (ii) with the appropriate isocyanate utilising General Method 16.

|       |                                                                                                                              | General | LCMS |       |
| ----- | ---------------------------------------------------------------------------------------------------------------------------- | ------- | ---- | ----- |
| Example | Compound Name                                                                                                              | Method  | RT   | (M+)  |
| 156 | Ethyl 2-amino-4-{4-[(4-methoxyphenyl)-carbamoyl]-3-methylpiperazin-1-yl}thieno[2,3-d]-pyrimidine-5-carboxylate | 16 | 2.19 | 471.3 |
| 157 | Ethyl 2-amino-4-{4-[(4-methoxyphenyl)-carbamoyl]-2-methylpiperazin-1-yl}thieno[2,3-d]-pyrimidine-5-carboxylate | 16 | 2.24 | 471.4 |
| 158 | Ethyl 2-amino-4-{4-[2-(3-methoxyphenoxy)acetyl]-3-methylpiperazin-1-yl}thieno[2,3-d]pyrimidine-5-carboxylate | 12 | 2.28 | 486.4 |
| 159 | Ethyl 2-amino-4-{4-[2-(4-methoxyphenoxy)acetyl]-3-methylpiperazin-1-yl}thieno[2,3-d]pyrimidine-5-carboxylate | 12 | 2.23 | 486.4 |

-continued

| Example | Compound Name | General Method | LCMS RT | (M+) |
|---|---|---|---|---|
| 160 | Ethyl 2-amino-4-[2-methyl-4-(p-tolylcarbamoyl)-piperazin-1-yl]thieno[2,3-d]pyrimidine-5-carboxylate | 16 | 2.30 | 455.5 |
| 161 | Ethyl 2-amino-4-{4-[(3-methoxyphenyl)-carbamoyl]-2-methylpiperazin-1-yl}thieno[2,3-d]-pyrimidine-5-carboxylate | 16 | 2.35 | 471.4 |
| 162 | Ethyl 2-amino-4-{4-[(3-methoxyphenyl)-carbamoyl]-3-methylpiperazin-1-yl}thieno[2,3-d]-pyrimidine-5-carboxylate | 16 | 2.26 | 471.3 |
| 163 | Ethyl 2-amino-4-[3-methyl-4-(p-tolylcarbamoyl)-piperazin-1-yl]thieno[2,3-d]pyrimidine-5-carboxylate | 16 | 2.37 | 455.4 |
| 164 | Ethyl 2-amino-4-{4-[2-(3-methoxyphenoxy)acetyl]-2-methylpiperazin-1-yl}thieno[2,3-d]pyrimidine-5-carboxylate | 12 | 2.18 | 486.3 |
| 165 | Ethyl 2-amino-4-{4-[2-(4-methoxyphenoxy)acetyl]-2-methylpiperazin-1-yl}thieno[2,3-d]pyrimidine-5-carboxylate | 12 | 2.14 | 486.3 |
| 166 | Ethyl 2-amino-4-{4-[3-(4-methoxyphenyl)-propanoyl]-3-methylpiperazin-1-yl}thieno[2,3-d]-pyrimidine-5-carboxylate | 12 | 2.32 | 484.4 |
| 167 | Ethyl 2-amino-4-{4-[3-(4-methoxyphenyl)-propanoyl]-2-methylpiperazin-1-yl}thieno[2,3-d]-pyrimidine-5-carboxylate | 12 | 2.21 | 484.3 |
| 168 | Ethyl 2-amino-4-{5-[2-(3-methoxyphenoxy)acetyl]-2,5-diazabicyclo[2.2.1]heptan-2-yl}thieno[2,3-d]-pyrimidine-5-carboxylate | 12 | 2.17 | 484.3 |
| 169 | Ethyl 2-amino-4-{5-[(3-methoxyphenyl)-carbamoyl]-2,5-diazabicyclo[2.2.1]heptan-2-yl}-thieno[2,3-d]pyrimidine-5-carboxylate | 16 | 2.20 | 469.3 |
| 170 | Ethyl 2-amino-4-[5-(p-tolylcarbamoyl)-2,5-diazabicyclo[2.2.1]heptan-2-yl]thieno[2,3-d]-pyrimidine-5-carboxylate | 16 | 2.30 | 453.3 |
| 171 | Ethyl 2-amino-4-{5-[(4-methoxyphenyl)-carbamoyl]-2,5-diazabicyclo[2.2.1]heptan-2-yl}-thieno[2,3-d]pyrimidine-5-carboxylate | 16 | 2.15 | 469.3 |
| 172 | Ethyl 2-amino-4-{5-[3-(4-methoxyphenyl)-propanoyl]-2,5-diazabicyclo[2.2.1]heptan-2-yl}-thieno[2,3-d]pyrimidine-5-carboxylate | 12 | 2.14 | 482.3 |
| 173 | Ethyl 2-amino-4-{5-[2-(4-methoxyphenoxy)acetyl]-2,5-diazabicyclo[2.2.1]heptan-2-yl}thieno[2,3-d]-pyrimidine-5-carboxylate | 12 | 2.12 | 484.4 |
| 174 | Ethyl 2-amino-4-{4-[(4-methoxy-2-methylphenyl)-carbamoyl]-2-methylpiperazin-1-yl}thieno[2,3-d]-pyrimidine-5-carboxylate | 16 | 2.15 | 485.2 |
| 175 | Ethyl 2-amino-4-{(2S)-4-[(4-methoxy-2-methyl-phenyl)carbamoyl]-2-methylpiperazin-1-yl]-thieno[2,3-d]pyrimidine-5-carboxylate | 16 | 1.90 | 485.2 |

Examples 176 to 245

The following compounds were prepared from Intermediate 33 via the indicated General Method.

| Example | Compound Name | General Method | LCMS RT | (M+) |
|---|---|---|---|---|
| 176 | 4-(2-Aminothieno[2,3-d]pyrimidin-4-yl)-N-(3-chloro-4-methoxyphenyl)piperazine-1-carboxamide | 16 | 2.32 | 419.2 |
| 177 | 4-(2-Aminothieno[2,3-d]pyrimidin-4-yl)-N-(o-tolyl)piperazine-1-carboxamide | 16 | 1.79 | 369.2 |
| 178 | 4-(2-Aminothieno[2,3-d]pyrimidin-4-yl)-N-(4-methoxyphenyl)piperazine-1-carboxamide | 16 | 2.05 | 385.3 |
| 179 | 4-(2-Aminothieno[2,3-d]pyrimidin-4-yl)-N-(4-ethoxyphenyl)piperazine-1-carboxamide | 16 | 2.26 | 399.3 |
| 180 | 4-(2-Aminothieno[2,3-d]pyrimidin-4-yl)-N-(benzo[d][1,3]dioxol-5-yl)piperazine-1-carboxamide | 16 | 2.60 | 399.2 |
| 181 | 4-(2-Aminothieno[2,3-d]pyrimidin-4-yl)-N-[4-(trifluoromethoxy)phenyl]piperazine-1-carboxamide | 16 | 2.56 | 439.3 |

-continued

| Example | Compound Name | General Method | LCMS RT | (M+) |
|---|---|---|---|---|
| 182 | 4-(2-Aminothieno[2,3-d]pyrimidin-4-yl)-N-(m-tolyl)piperazine-1-carboxamide | 16 | 1.90 | 369.1 |
| 183 | 4-(2-Aminothieno[2,3-d]pyrimidin-4-yl)-N-[4-(difluoromethoxy)phenyl]piperazine-1-carboxamide | 16 | 2.40 | 421.2 |
| 184 | 1-[4-(2-Aminothieno[2,3-d]pyrimidin-4-yl)-piperazin-1-yl]-2-phenoxyethanone | 12 | 1.86 | 370.2 |
| 185 | [4-(2-Aminothieno[2,3-d]pyrimidin-4-yl)piperazin-1-yl](1H-pyrazol-3-yl)methanone | 12 | 1.32 | 330.2 |
| 186 | 4-(2-Aminothieno[2,3-d]pyrimidin-4-yl)-N-phenyl-piperazine-1-carboxamide | 16 | 1.72 | 355.1 |
| 187 | [4-(2-Aminothieno[2,3-d]pyrimidin-4-yl)piperazin-1-yl](5-methyl-1H-pyrazol-3-yl)methanone | 12 | 1.46 | 344.2 |
| 188 | [4-(2-Aminothieno[2,3-d]pyrimidin-4-yl)piperazin-1-yl](imidazo[1,2-a]pyridin-2-yl)methanone | 12 | 1.91 | 380.2 |
| 189 | [4-(2-Aminothieno[2,3-d]pyrimidin-4-yl)piperazin-1-yl](isoquinolin-3-yl)methanone | 12 | 2.14 | 391.2 |
| 190 | 4-(2-Aminothieno[2,3-d]pyrimidin-4-yl)-N-benzyl-piperazine-1-carboxamide | 16 | 1.77 | 369.2 |
| 191 | 1-[4-(2-Aminothieno[2,3-d]pyrimidin-4-yl)-piperazin-1-yl]-3-(4-methoxyphenyl)propan-1-one | 12 | 2.02 | 398.1 |
| 192 | 4-(2-Aminothieno[2,3-d]pyrimidin-4-yl)-N-(4-methoxybenzyl)piperazine-1-carboxamide | 16 | 2.12 | 399.2 |
| 193 | [4-(2-Aminothieno[2,3-d]pyrimidin-4-yl)piperazin-1-yl](pyrazin-2-yl)methanone | 12 | 1.48 | 342.1 |
| 194 | 1-[4-(2-Aminothieno[2,3-d]pyrimidin-4-yl)-piperazin-1-yl]-2-[4-(dimethylamino)phenyl]-ethanone | 12 | 2.00 | 397.2 |
| 195 | 1-[4-(2-Aminothieno[2,3-d]pyrimidin-4-yl)-piperazin-1-yl]-3-(1H-benzo[d]imidazol-2-yl)-propan-1-one | 12 | 1.74 | 408.3 |
| 196 | [4-(2-Aminothieno[2,3-d]pyrimidin-4-yl)piperazin-1-yl](1-methyl-1H-imidazol-2-yl)methanone | 12 | 1.44 | 344.2 |
| 197 | 1-[4-(2-Aminothieno[2,3-d]pyrimidin-4-yl)-piperazin-1-yl]-2-(pyridin-4-yl)ethanone | 12 | 1.36 | 355.2 |
| 198 | (S)-1-[4-(2-Aminothieno[2,3-d]pyrimidin-4-yl)-piperazin-1-yl]-3-hydroxy-3-phenylpropan-1-one | 12 | 1.65 | 384.2 |
| 199 | 1-[4-(2-Aminothieno[2,3-d]pyrimidin-4-yl)-piperazin-1-yl]-2-(thien-3-yl)ethanone | 12 | 2.24 | 363.3 |
| 200 | 4-[4-(Pyridin-3-ylmethyl)piperazin-1-yl]thieno[2,3-d]pyrimidin-2-amine | 13 | 1.5 | 327.1 |
| 201 | [4-(2-Aminothieno[2,3-d]pyrimidin-4-yl)piperazin-1-yl](1-methyl-1H-imidazol-5-yl)methanone | 12 | 1.34 | 344.2 |
| 202 | 1-[4-(2-Aminothieno[2,3-d]pyrimidin-4-yl)-piperazin-1-yl]-2-(3,4-dimethoxyphenyl)ethanone | 12 | 2.02 | 414.2 |
| 203 | [4-(2-Aminothieno[2,3-d]pyrimidin-4-yl)piperazin-1-yl](quinoxalin-2-yl)methanone | 12 | 1.9 | 392.2 |
| 204 | [4-(2-Aminothieno[2,3-d]pyrimidin-4-yl)piperazin-1-yl](1H-indazol-3-yl)methanone | 12 | 1.78 | 380.2 |
| 205 | 4-(2-Aminothieno[2,3-d]pyrimidin-4-yl)-N-(1-phenylethyl)piperazine-1-carboxamide | 16 | 2.23 | 383.2 |
| 206 | 1-[4-(2-Aminothieno[2,3-d]pyrimidin-4-yl)-piperazin-1-yl]-3-phenylpropan-1-one | 12 | 1.96 | 368.2 |
| 207 | [4-(2-Aminothieno[2,3-d]pyrimidin-4-yl)piperazin-1-yl](pyridin-3-yl)methanone | 12 | 1.30 | 341.1 |
| 208 | 1-[4-(2-Aminothieno[2,3-d]pyrimidin-4-yl)-piperazin-1-yl]-3-(furan-2-yl)propan-1-one | 12 | 1.88 | 358.1 |
| 209 | [4-(2-Aminothieno[2,3-d]pyrimidin-4-yl)piperazin-1-yl][6-(hydroxymethyl)pyridin-2-yl]methanone | 12 | 1.98 | 371.2 |
| 210 | [4-(2-Aminothieno[2,3-d]pyrimidin-4-yl)piperazin-1-yl](phenyl)methanone | 12 | 1.72 | 340.1 |
| 211 | 1-[4-(2-Aminothieno[2,3-d]pyrimidin-4-yl)-piperazin-1-yl]-3-cyclopentylpropan-1-one | 12 | 2.20 | 360.1 |
| 212 | 1-[4-(2-Aminothieno[2,3-d]pyrimidin-4-yl)-piperazin-1-yl]-3-(4-methylpiperazin-1-yl)propan-1-one | 12 | 1.28 | 393.3 |
| 213 | [4-(2-Aminothieno[2,3-d]pyrimidin-4-yl)piperazin-1-yl](quinolin-2-yl)methanone | 12 | 1.86 | 391.3 |
| 214 | 4-[4-(Pyridin-2-ylmethyl)piperazin-1-yl]thieno[2,3-d]pyrimidin-2-amine | 13 | 1.54 | 327.1 |
| 215 | 1-[4-(2-Aminothieno[2,3-d]pyrimidin-4-yl)-piperazin-1-yl]-3-(3-methoxyphenyl)propan-1-one | 12 | 2.04 | 398.1 |
| 216 | 1-[4-(2-Aminothieno[2,3-d]pyrimidin-4-yl)-piperazin-1-yl]-3-(o-tolyl)propan-1-one | 12 | 2.17 | 382.1 |

-continued

| Example | Compound Name | General Method | LCMS RT | (M+) |
|---|---|---|---|---|
| 217 | 1-[4-(2-Aminothieno[2,3-d]pyrimidin-4-yl)-piperazin-1-yl]-2-(morpholin-4-yl)ethanone | 12 | 1.31 | 363.3 |
| 218 | 4-[4-(3-Phenylbutyl)piperazin-1-yl]thieno[2,3-d]-pyrimidin-2-amine | 15 | 2.56 | 368.2 |
| 219 | 4-(4-Benzylpiperazin-1-yl)thieno[2,3-d]pyrimidin-2-amine | 14 | 2.13 | 326.1 |
| 220 | 4-[4-(2-Phenylethyl)piperazin-1-yl]thieno[2,3-d]-pyrimidin-2-amine | 13 | 2.2 | 340.1 |
| 221 | 4-[4-(3-Phenylpropyl)piperazin-1-yl]thieno[2,3-d]-pyrimidin-2-amine | 15 | 2.37 | 354.2 |
| 222 | tert-Butyl 4-[4-(2-aminothieno[2,3-d]pyrimidin-4-yl)piperazine-1-carbonyl]piperidine-1-carboxylate | 12 | 2.09 | 447.3 |
| 223 | 1-[4-(2-Aminothieno[2,3-d]pyrimidin-4-yl)-piperazin-1-yl]-2-(dimethylamino)ethanone | 12 | 1.29 | 321.2 |
| 224 | 1-[4-(2-Aminothieno[2,3-d]pyrimidin-4-yl)-piperazin-1-yl]-2-methyl-3-phenylpropan-1-one | 12 | 2.12 | 382.1 |
| 225 | 1-[4-(2-Aminothieno[2,3-d]pyrimidin-4-yl)-piperazin-1-yl]-3-(4-fluorophenyl)propan-1-one | 12 | 2.10 | 386.1 |
| 226 | 1-[4-(2-Aminothieno[2,3-d]pyrimidin-4-yl)-piperazin-1-yl]-3-(p-tolyl)propan-1-one | 12 | 2.20 | 382.1 |
| 227 | 1-[4-(2-Aminothieno[2,3-d]pyrimidin-4-yl)-piperazin-1-yl]-3-(1H-indol-3-yl)propan-1-one | 12 | 2.14 | 407.2 |
| 228 | (S)-[4-(2-Aminothieno[2,3-d]pyrimidin-4-yl)-piperazin-1-yl](1-methylpyrrolidin-2-yl)methanone | 12 | 1.41 | 347.3 |
| 229 | [4-(2-Aminothieno[2,3-d]pyrimidin-4-yl)piperazin-1-yl](1H-benzo[d]imidazol-2-yl)methanone | 12 | 1.64 | 380.2 |
| 230 | (S)-1-[4-(2-Aminothieno[2,3-d]pyrimidin-4-yl)-piperazin-1-yl]-2-(methylamino)-2-phenylethanone | 12 | 1.71 | 383.6 |
| 231 | [4-(2-Aminothieno[2,3-d]pyrimidin-4-yl)piperazin-1-yl][1-(4-methoxyphenyl)cyclopropyl]methanone | 12 | 2.18 | 410.3 |
| 232 | 1-[4-(2-Aminothieno[2,3-d]pyrimidin-4-yl)-piperazin-1-yl]-3-(2-methyl-1H-imidazol-1-yl)-propan-1-one | 12 | 2.07 | 372.3 |
| 233 | (S)-tert-Butyl N-{2-[4-(2-aminothieno[2,3-d]-pyrimidin-4-yl)piperazin-1-yl]-2-oxo-1-phenyl-ethyl}-N-(methyl)carbamate | 12 | 3.54 | 483.6 |
| 234 | (S)-tert-Butyl 3-[4-(2-aminothieno[2,3-d]pyrimidin-4-yl)piperazine-1-carbonyl]-3,4-dihydro-isoquinoline-2(1H)-carboxylate | 12 | 2.44 | 495.4 |
| 235 | [4-(2-Aminothieno[2,3-d]pyrimidin-4-yl)piperazin-1-yl](pyridin-2-yl)methanone | 12 | 1.39 | 341.2 |
| 236 | 1-[4-(2-Aminothieno[2,3-d]pyrimidin-4-yl)-piperazin-1-yl]-3-(morpholin-4-yl)propan-1-one | 12 | 1.29 | 377.2 |
| 237 | 1-[4-(2-Aminothieno[2,3-d]pyrimidin-4-yl)-piperazin-1-yl]-2-(4-methylpiperazin-1-yl)ethanone | 12 | 1.32 | 376.5 |
| 238 | [4-(2-Aminothieno[2,3-d]pyrimidin-4-yl)piperazin-1-yl](2-phenylcyclopropyl)methanone | 12 | 2.18 | 380.4 |
| 239 | 1-[4-(2-Aminothieno[2,3-d]pyrimidin-4-yl)-piperazin-1-yl]-3-(3-chloro-4-methoxyphenyl)-propan-1-one | 12 | 2.12 | 433.2 |
| 240 | 1-[4-(2-Aminothieno[2,3-d]pyrimidin-4-yl)-piperazin-1-yl]-3-(pyridin-3-yl)propan-1-one | 12 | 1.53 | 369.3 |
| 241 | 1-[4-(2-Aminothieno[2,3-d]pyrimidin-4-yl)-piperazin-1-yl]-3-(2-methoxyphenyl)propan-1-one | 12 | 2.06 | 398.1 |
| 242 | [4-(2-Aminothieno[2,3-d]pyrimidin-4-yl)piperazin-1-yl](1H-indol-2-yl)methanone | 12 | 2.15 | 379.3 |
| 243 | [4-(2-Aminothieno[2,3-d]pyrimidin-4-yl)piperazin-1-yl](isoquinolin-1-yl)methanone | 12 | 1.76 | 391.3 |
| 244 | [4-(2-Aminothieno[2,3-d]pyrimidin-4-yl)piperazin-1-yl](1,2,3,4-tetrahydronaphthalen-2-yl)methanone | 12 | 2.23 | 394.1 |
| 245 | [4-(2-Aminothieno[2,3-d]pyrimidin-4-yl)piperazin-1-yl](imidazo[1,2-a]pyridin-3-yl)methanone | 12 | 1.57 | 380.3 |

Examples 246 to 257

The following compounds were prepared by a three-step procedure comprising: (i) reaction of Intermediate 25 with the appropriate BOC-protected diamine derivative via General Method 4; (ii) removal of the BOC protecting group via General Method 8; and (iii) coupling of the amine resulting from step (ii) with the appropriate carboxylic acid utilising General Method 12; or coupling of the amine resulting from step (ii) with the appropriate isocyanate utilising General Method 16.

| Example | Compound Name | General Method | LCMS RT | (M+) |
|---|---|---|---|---|
| 246 | 4-(2-Aminothieno[2,3-d]pyrimidin-4-yl)-N-(4-methoxyphenyl)-3-methylpiperazine-1-carboxamide | 16 | 2.03 | 399.3 |
| 247 | 4-(2-Aminothieno[2,3-d]pyrimidin-4-yl)-N-(4-methoxy-2-methylphenyl)-3-methylpiperazine-1-carboxamide | 16 | 1.93 | 413.2 |
| 248 | 4-(2-Aminothieno[2,3-d]pyrimidin-4-yl)-N-(3-methoxyphenyl)-3-methylpiperazine-1-carboxamide | 16 | 2.07 | 399.3 |
| 249 | 1-[4-(2-Aminothieno[2,3-d]pyrimidin-4-yl)-3-methylpiperazin-1-yl]-2-(3-methoxyphenoxy)-ethanone | 12 | 2.27 | 414.3 |
| 250 | 1-[4-(2-Aminothieno[2,3-d]pyrimidin-4-yl)-3-methylpiperazin-1-yl]-2-(4-methoxyphenoxy)-ethanone | 12 | 2.12 | 414.3 |
| 251 | 4-(2-Aminothieno[2,3-d]pyrimidin-4-yl)-3-(hydroxymethyl)-N-(p-tolyl)piperazine-1-carboxamide | 16 | 1.95 | 399.2 |
| 252 | 4-(2-Aminothieno[2,3-d]pyrimidin-4-yl)-3-(hydroxymethyl)-N-(4-methoxyphenyl)piperazine-1-carboxamide | 16 | 1.77 | 415.2 |
| 253 | 1-[4-(2-Aminothieno[2,3-d]pyrimidin-4-yl)-3-(hydroxymethyl)piperazin-1-yl]-2-(3-methoxy-phenoxy)ethanone | 12 | 1.88 | 430.3 |
| 254 | (3S)-4-(2-Aminothieno[2,3-d]pyrimidin-4-yl)-N-(4-methoxyphenyl)-3-methylpiperazine-1-carboxamide | 16 | 1.67 | 399.8 |
| 255 | (3S)-4-(2-Aminothieno[2,3-d]pyrimidin-4-yl)-N-(4-methoxy-2-methylphenyl)-3-methylpiperazine-1-carboxamide | 16 | 1.74 | 413.8 |
| 256 | (3R)-4-(2-Aminothieno[2,3-d]pyrimidin-4-yl)-N-(4-methoxyphenyl)-3-methylpiperazine-1-carboxamide | 16 | 1.65 | 399.8 |
| 257 | (3R)-4-(2-Aminothieno[2,3-d]pyrimidin-4-yl)-N-(4-methoxy-2-methylphenyl)-3-methylpiperazine-1-carboxamide | 16 | 1.78 | 413.8 |

Example 258

4-(2-Amino-5-cyanothieno[2,3-d]pyrimidin-4-yl)-N-(4-methoxyphenyl)-3-methylpiperazine-1-carboxamide To a stirred solution of Intermediate 59 (0.1 g) in DMF (2 mL) was added triethylamine (0.130 mL, 3 eq.). The reaction mixture was stirred for 15 minutes at r.t., then 4-methoxyphenyl isocyanate (48 mg, 1 eq.) was added. The reaction mixture was stirred for 3 h. The reaction mixture was then extracted with ethyl acetate and water. The organic layer was evaporated and the crude residue was purified by column chromatography (80% EtOAc in hexane), to yield the title compound (45 mg) as a solid. $\delta_H$ (DMSO-$d_6$, 400 MHz) 8.41 (1H, s), 8.21 (1H, s), 7.28 (2H, m), 6.80 (4H, m), 4.15 (1H, br s), 4.10 (1H, d), 3.81 (1H, d), 3.61 (3H, s), 3.55-3.05 (4H, br m), 1.10 (3H, d). MS (m/z) 424 [M+H]+.

Example 259

4-(2-Amino-5-cyanothieno[2,3-d]pyrimidin-4-yl)-N-(4-methoxy-2-methylphenyl)-3-methylpiperazine-1-carboxamide To a stirred solution of Intermediate 59 (0.120 g) in DMF (2 mL) was added triethylamine (0.160 mL, 3 eq.). The reaction mixture was stirred for 15 minutes at r.t., then 4-methoxy-2-methylphenyl isocyanate (63 mg, 1 eq.) was added. The reaction mixture was stirred at r.t. for 2 h. The reaction mixture was then extracted with ethyl acetate and water. The organic layer was evaporated and the crude residue was purified by column chromatography (80% EtOAc in hexane), to yield the title compound (43 mg) as a solid. $\delta_H$ (DMSO-$d_6$, 400 MHz) 8.29 (1H, s), 8.00 (1H, s), 7.01 (1H, d), 6.82 (2H, s), 6.75 (1H, s), 6.62 (1H, m), 4.28 (1H, br m), 4.10 (1H, br m), 3.87 (1H, br m), 3.72 (3H, s), 3.35 (3H, m), 3.17 (1H, m), 2.15 (3H, s), 1.17 (3H, d). MS (m/z) 438 [M+H]+.

Example 260

General Method 17

4-[2-Amino-5-(3-methyl-1,2,4-oxadiazol-5-yl)thieno[2,3-d]pyrimidin-4-yl]-N-(4-methoxyphenyl)piperazine-1-carboxamide To a solution of Intermediate 60 (100 mg, 0.2 mmol) in DCM (2 mL) was added potassium tert-butoxide (70 mg, 0.61 mmol). The reaction mixture was stirred at room temperature for 2 h. The reaction mixture was then concentrated and the crude residue was purified by column chromatography (silica: 100-200 mesh, MeOH:DCM) to afford the title compound (15.2 mg, 20.0%) as white solid. $\delta_H$ (400 MHz, DMSO-$d_6$) 8.36 (s, 1H), 8.00 (s, 1H), 7.34-7.27 (m, 2H), 6.85-6.77 (m, 2H), 6.69 (s, 2H), 3.69 (s, 3H), 3.49 (d, J 12.1 Hz, 4H, merged with solvent water peak), 3.23 (dd, J 6.3, 3.4 Hz, 4H), 2.47 (d, J 18.5 Hz, 3H). LCMS: MH$^+$ 467.20, RT 1.81 minutes.

Example 261

4-[2-Amino-5-(3-isopropyl-1,2,4-oxadiazol-5-yl) thieno[2,3-d]pyrimidin-4-yl]-N-(4-methoxyphenyl) piperazine-1-carboxamide The title compound (20.2 mg, 22.0%) was prepared from Intermediate 61 in accordance with General Method 17. $\delta_H$ (400 MHz, DMSO-$d_6$) 8.36 (s, 1H), 7.98 (s, 1H), 7.30 (d, J 8.9 Hz, 2H), 6.81 (d, J 9.0 Hz, 2H), 6.69 (s, 2H), 3.69 (s, 3H), 3.72-3.22 (s, 9H, merged with solvent peak), 1.33 (d, J 6.9 Hz, 6H). LCMS: MH$^+$ 495.2, RT 2.11 minutes.

Example 262

4-[2-Amino-5-(3-tert-butyl-1,2,4-oxadiazol-5-yl) thieno[2,3-d]pyrimidin-4-yl]-N-(4-methoxyphenyl) piperazine-1-carboxamide The title compound (35 mg, 31.5%) was prepared from Intermediate 62 in accordance with General Method 17. $\delta_H$ (400 MHz, DMSO-$d_6$) 8.36 (s, 1H), 7.96 (s, 1H), 7.34-7.25 (m, 2H), 6.85-6.77 (m, 2H), 6.68 (s, 2H), 3.69 (s, 3H), 3.30 (d, J 8.3 Hz, 4H), 3.22 (dd, J 6.6, 3.1 Hz, 4H), 1.38 (s, 9H). LCMS: MH$^+$ 509.2, RT 2.31 minutes.

The invention claimed is:

1. A compound of formula (I), or a pharmaceutically acceptable salt or solvate thereof:

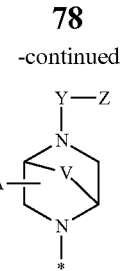

(I)

wherein

Q represents a group of formula (Qa) or (Qb):

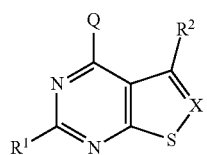

(Qa)

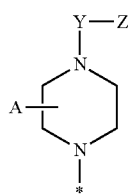

(Qb)

in which the asterisk (*) represents the point of attachment to the remainder of the molecule;

V represents —CH$_2$—, —CH$_2$CH$_2$— or —CH$_2$CH$_2$CH$_2$—;

X represents C—R$^3$ or N;

Y represents a covalent bond, or a linker group selected from —C(O)—, —S(O)—, —S(O)$_2$—, —C(O)O—, —C(O)N(R$^4$)— and —S(O)$_2$N(R$^4$)—;

Z represents hydrogen; or C$_{1-6}$ alkyl, C$_{3-7}$ cycloalkyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$)alkyl, any of which groups may be optionally substituted by one or more substituents;

A represents hydrogen or trifluoromethyl; or C$_{1-6}$ alkyl, optionally substituted by one or more substituents independently selected from —OR$^a$ and —NR$^b$R$^c$;

R$^1$ is —NH$_2$;

R$^2$ represents halogen, cyano, nitro, hydroxy, trifluoromethyl, trifluoromethoxy, —OR$^a$, —SR$^a$, —SOR$^a$, —SO$_2$R$^a$, —NR$^b$R$^c$, —CH$_2$NR$^b$R$^c$, —NR$^c$COR$^d$, —CH$_2$NR$^c$COR$^d$, —NR$^c$CO$_2$R$^d$, —NHCONR$^b$R$^c$, —NR$^c$SO$_2$R$^e$, —N(SO$_2$R$^e$)$_2$, —NHSO$_2$NR$^b$R$^c$, —COR$^d$, —CO$_2$R$^d$, —CONR$^b$R$^c$, —CON(OR$^a$)R$^b$ or —SO$_2$NR$^b$R$^c$; or C$_{1-6}$ alkyl, C$_{3-7}$ cycloalkyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$)alkyl, any of which groups may be optionally substituted by one or more substituents;

R$^3$ and R$^4$ independently represent hydrogen; or C$_{1-6}$ alkyl, optionally substituted by one or more substituents independently selected from —OR$^a$ and —NR$^b$R$^c$;

R$^a$ represents hydrogen; or R$^a$ represents C$_{1-6}$ alkyl, aryl, aryl(C$_{1-6}$)alkyl, heteroaryl or heteroaryl(C$_{1-6}$)alkyl, any of which groups may be optionally substituted by one or more substituents;

R$^b$ and R$^c$ independently represent hydrogen or trifluoromethyl; or C$_{1-6}$ alkyl, C$_{3-7}$ cycloalkyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$)alkyl, any of which groups may be optionally substituted by one or more substituents; or R$^b$ and R$^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more sub stituents;

R$^d$ represents hydrogen; or C$_{1-6}$ alkyl, C$_{3-7}$ cycloalkyl, aryl, C$_{3-7}$ heterocycloalkyl or heteroaryl, any of which groups may be optionally substituted by one or more sub stituents; and $R^e$ represents $C_{1-6}$ alkyl, aryl or heteroaryl, any of which groups may be optionally substituted by one or more substituents.

2. The compound as claimed in claim 1 wherein $R^2$ represents cyano, hydroxy, trifluoromethyl, —$NR^cCO_2R^d$, —$CO_2R^d$, —$CONR^bR^c$ or —$CON(OR^a)R^b$; or $R^2$ represents $C_{1-6}$ alkyl, $C_{3-7}$ cycloalkyl, aryl or heteroaryl, any of which groups may be optionally substituted by one or two substituents independently selected from halogen, $C_{1-6}$ alkyl, hydroxy and $C_{1-6}$ alkoxy.

3. The compound as claimed in claim 1 represented by formula (IIA), or a pharmaceutically acceptable salt or solvate thereof:

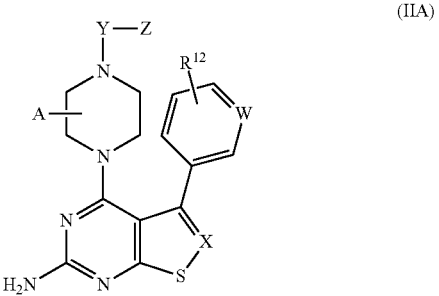

(IIA)

wherein
W represents C—$R^{11}$ or N;
$R^{11}$ represents hydrogen, halogen, cyano, $C_{1-6}$ alkyl, trifluoromethyl, hydroxy, $C^{1-6}$ alkoxy, trifluoromethoxy or $C_{1-6}$ alkylaminosulphonyl; and
$R^{12}$ represents hydrogen, halogen, cyano, nitro, $C_{1-6}$ alkyl, trifluoromethyl, hydroxy, $C_{1-6}$ alkoxy, trifluoromethoxy, $C_{1-6}$ alkylthio, $C_{1-6}$ alkylsulphonyl, amino or di($C_{1-6}$)alkylamino.

4. The compound as claimed in claim 1 represented by formula (IIB), or a pharmaceutically acceptable salt or solvate thereof:

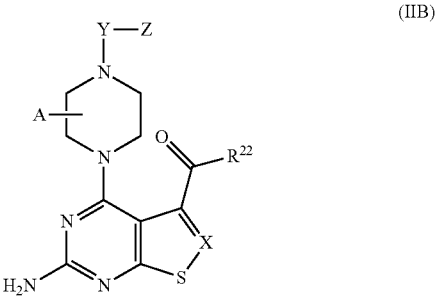

(IIB)

wherein
$R^{22}$ represents —$R^d$, —$OR^d$, —$NR^bR^c$ or —$N(OR^a)R^b$.

5. The compound as claimed in claim 1 wherein Z represents $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or two substituents independently selected from halogen, cyano, $C_{1-6}$ alkyl, aryl, ($C_{1-6}$)alkoxyaryl, ($C_{1-6}$)alkyl($C_{3-7}$)-heterocycloalkyl, ($C_{3-7}$)heterocycloalkyl($C_{1-6}$)alkyl, hydroxy, hydroxy($C_{1-6}$)alkyl, $C_{1-6}$ alkoxy, difluoromethoxy, trifluoromethoxy, aryloxy, haloaryloxy, ($C_{1-6}$)alkoxyaryloxy, ($C_{1-3}$)alkylenedioxy, $C_{1-6}$ alkylamino, di($C_{1-6}$)alkylamino, N—[($C_{2-6}$)-alkoxycarbonyl]-N—[($C_{1-6}$)alkyl]amino and $C_{2-6}$ alkoxycarbonyl.

6. The compound as claimed in claim 1 wherein A represents hydrogen; or A represents $C_{1-6}$ alkyl, optionally substituted by —$OR^a$.

7. The compound as claimed in claim 1 represented by formula (IIC), or a pharmaceutically acceptable salt or solvate thereof:

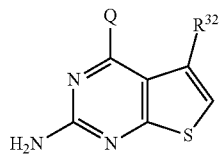

(IIC)

wherein
$R^{32}$ represents cyano or —$CO_2R^d$.

8. The compound as claimed in claim 7 wherein Q represents a group of formula (Qa-1):

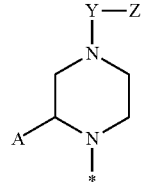

(Qa-1)

in which the asterisk (*) represents the point of attachment to the remainder of the molecule.

9. A compound that is
1  2-Amino-5-(4-fluorophenyl)-4-(piperazin-1-yl)thieno[2,3-d]pyrimidine,
2  1{4-[2-amino-5-(4-fluorophenyl)thieno[2,3-d]pyrimidin-4-yl]piperazin-1-y}-2-(4-chlorophenoxy)ethanone,
3  {4-[2-Amino-5-(4-fluorophenyl)thieno[2,3-d]pyrimidin-4-yl]piperazin-1-yl}-(cyclopropyl)methanone,
4  4-[2-Amino-5-(4-fluorophenyl)thieno[2,3-d]pyrimidin-4-yl]-N-(m-tolyl)piperazine-1-carboxamide,
5  4-[2-Amino-5-(4-fluorophenyl)thieno[2,3-d]pyrimidin-4-yl]-N-(4-methoxyphenyl)-piperazine-1-carboxamide,
6  4-[2-Amino-5-(4-fluorophenyl)thieno[2,3-d]pyrimidin-4-yl]-N-(4-isopropylphenyl)-piperazine-1-carboxamide,
7  4-[2-Amino-5-(4-fluorophenyl)thieno[2,3-d]pyrimidin-4-yl]-N-(4-cyanophenyl)-piperazine-1-carboxamide,
8  4-[2-Amino-5-(4-fluorophenyl)thieno[2,3-d]pyrimidin-4-yl]-N-(4-chlorophenyl)-piperazine-1-carboxamide,
9  4-[2-Amino-5-(4-fluorophenyl)thieno[2,3-d]pyrimidin-4-yl]-N-[4-(dimethylamino)-phenyl]piperazine-1-carboxamide,
10  2-Amino-4-(piperazin-1-yl)-5-(pyridin-3-yl)thieno[2,3d]pyrimidine,
11  2-Amino-6-methyl-5-phenyl-4-(piperazin-1-yl)thieno[2,3-d]pyrimidine,
12  4-[2-Amino-5-(pyridin-3-yl)thieno[2,3-d]pyrimidin-4-yl]-N-(2-methoxyphenyl)-piperazine-1-carboxamide,
13  4-(2-Amino-6-methyl-5-phenylthieno[2,3-d]pyrimidin-4-yl)-N-(4-methoxyphenyl)-piperazine-1-carboxamide, 14  3-(4-Fluorophenyl)-4-(4-methylpiperazin-1-yl)isothiazolo[5,4-d]pyrimidine,
15  3-(4-Fluorophenyl)-4-(piperazin-1-yl)isothiazolo[5,4-d]pyrimidin-6-amine,
16  3-(4-Fluorophenyl)-4-(4-methylpiperazin-1-yl)isothiazolo[5,4-d]pyrimidin-6-amine,
17  4-[6-Amino-3-(4-fluorophenyl)isothiazolo[5,4-d]pyrimidin-4-yl]-N-(p-tolyl)piperazine-1-carboxamide,
18  4-[6-Amino-3-(4-fluorophenyl)isothiazolo[5,4-d]pyrimidin-4-yl]-N-(4-isopropylphenyl)-piperazine-1-carboxamide,
19  1-{4-[6-Amino-3-(4-fluorophenyl)isothiazolo[5,4-d]pyrimidin-4-yl]piperazin-1-yl}-2-(4-chlorophenoxy)ethanone,
20  2-Amino-5-(ethoxycarbonyl)-4-(piperazin-1-yl)thieno[2,3-d]pyrimidine,
21  4-[2-Amino-5-(ethoxycarbonyl)thieno[2,3-d]pyrimidin-4-yl]-N-(4-methoxyphenyl)-piperazine-1-carboxamide,
22  2-Amino-5-methyl-4-(piperazin-1-yl)thieno[2,3-d]pyrimidine,
23  2-Amino-5-isobutyl-4-(piperazin-1-yl)thieno[2,3-d]pyrimidine,
24  4-[2-Amino-5-methylthieno[2,3-d]pyrimidin-4-yl]-N-[4-(dimethylamino)phenyl]-piperazine-1-carboxamide,
25  4-[2-Amino-5-isobutylthieno[2,3-d]pyrimidin-4-yl]-N-[4-dimethylamino)phenyl]-piperazine-1-carboxamide,
26  2-Amino-4-[4-(4-methoxyphenylcarbamoyl)piperazin-1-yl]thieno[2,3-d]pyrimidine-5-carboxylic acid,
27  2-Amino-4-[4-(4-methoxyphenylcarbamoyl)piperazin-1-yl]thieno[2,3-d]pyrimidine-5-carboxylic acid methylamide,
28  2-Amino-4-[4-(4-methoxyphenylcarbamoyl)piperazin-1-yl]thieno[2,3-d]pyrimidine-5-carboxylic acid N-methoxy-N-methylamide,
29  2-Amino-4-[4-(4-methoxyphenylcarbamoyl)piperazin-1-yl]thieno[2,3-d]pyrimidine-5-carboxylic acid amide,
30  Benzyl 4-[2-amino-5-(4-fluorophenyl)thieno[2,3-d]pyrimidin-4-yl]piperazine-1-carboxylate,
31  4-Methoxyphenyl 4-[2-amino-5-(4-fluorophenyl)thieno[2,3-d]pyrimidin-4-yl]piperazine-1-carboxylate,
32  5-(4-Fluorophenyl)-4-[4-(3-methylbenzylsulfonyl)piperazin-1-yl]thieno[2,3-d]pyrimidin-2-amine,
33  5-(4-Fluorophenyl)-4-[4-(2-methyl-1H-imidazol-1-ylsulfonyl)piperazin-1-yl]thieno[2,3-d]pyrimidin-2-amine,
34  4-[2-Amino-5-(4-fluorophenyl)thieno[2,3-d]pyrimidin-4-yl]-N-(4-methoxyphenyl)-piperazine-1-sulfonamide,
35  4-[2-Amino-5-(4-fluorophenyl)thieno[2,3-d]pyrimidin-4-yl]-N-[3-(morpholin-4-ylmethyl)phenyl]piperazine-1-carboxamide,
36  4-[2-Amino-5-(4-fluorophenyl)thieno[2,3-d]pyrimidin-4-yl]-N-[4-(4-methylpiperazin-1-yl)phenyl]piperazine-1-carboxamide,
37  4-[2-Amino-5-(4-fluorophenyl)thieno[2,3-d]pyrimidin-4-yl]-N-(4-fluorophenyl)-piperazine-1-carboxamide,
38  4-[2-Amino-5-(4-fluorophenyl)thieno[2,3-d]pyrimidin-4-yl]-N-(2,4-dimethoxyphenyl)-piperazine-1-carboxamide,
39  4-[2-Amino-5-(4-fluorophenyl)thieno[2,3-d]pyrimidin-4-yl]-N-[4-(piperidin-1-ylmethyl)-phenyl]piperazine-1-carboxamide,
40  4-[2-Amino-5-(4-fluorophenyl)thieno[2,3-d]pyrimidin-4-yl]-N-(2,4-difluorophenyl)-piperazine-1-carboxamide,
41  4-[2-Amino-5-(pyridin-3-yl)thieno[2,3-d]pyrimidin-4-yl]-N-[4-(dimethylamino)phenyl]-piperazine-1-carboxamide,
42  4-[2-Amino-5-(pyridin-3-yl)thieno[2,3-d]pyrimidin-4-yl]-N-(4-methoxyphenyl)-piperazine-1-carboxamide,
43  4-[2-Amino-5-(pyridin-3-yl)thieno[2,3-d]pyrimidin-4-yl]-N-(3-methylphenyl)piperazine-1-carboxamide,
44  4-[2-Amino-5-(pyridin-3-yl)thieno[2,3-d]pyrimidin-4-yl]-N-[3-(morpholin-4-ylmethyl)-phenyl]piperazine-1-carboxamide,
45  4-[2-Amino-5-(pyridin-3-yl)thieno[2,3-d]pyrimidin-4-yl]-N-[4-(piperidin-1-ylmethyl)-phenyl]piperazine-1-carboxamide,
46  4-[2-Amino-5-(4-methoxyphenyl)thieno[2,3-d]pyrimidin-4-yl]-N-(4-methoxyphenyl)-piperazine-1-carboxamide,
47  4-[2-Amino-5-(4-methoxyphenyl)thieno[2,3-d]pyrimidin-4-yl]-N-(3-methylphenyl)-piperazine-1-carboxamide,
48  4-[2-Amino-5-(4-methoxyphenyl)thieno[2,3-d]pyrimidin-4-yl]-N-(2-methoxyphenyl)-piperazine-1-carboxamide,
49  4-[2-Amino-5-(4-methoxyphenyl)thieno[2,3-d]pyrimidin-4-yl]-N-[4-(dimethylamino)-phenyl]piperazine-1-carboxamide,
50  4-[2-Amino-5-(4-chlorophenyl)thieno[2,3-d]pyrimidin-4-yl]-N-(4-methoxyphenyl)-piperazine-1-carboxamide,
51  4-[2-Amino-5-(4-chlorophenyl)thieno[2,3-d]pyrimidin-4-yl]-N-[4-(dimethylamino)-phenyl]piperazine-1-carboxamide,
52  4-[2-Amino-5-(4-chlorophenyl)thieno[2,3-d]pyrimidin-4-yl]-N-(2-methoxyphenyl)-piperazine-1-carboxamide,
53  4-[2-Amino-5-(4-chlorophenyl)thieno[2,3-d]pyrimidin-4-yl]-N-(3-methylphenyl)-piperazine-1-carboxamide,
54  4-[2-Amino-5-(3-fluorophenyl)thieno[2,3-d]pyrimidin-4-yl]-N-[4-(dimethylamino)-phenyl]piperazine-1-carboxamide,
55  4-[2-Amino-5-(2-fluorophenyl)thieno[2,3-d]pyrimidin-4-yl]-N-[4-(dimethylamino)-phenyl]piperazine-1-carboxamide,
56  4-[2-Amino-5-(2-fluorophenyl)thieno[2,3-d]pyrimidin-4-yl]-N-[4-(4-methylpiperazin-1-yl)phenyl]piperazine-1-carboxamide,
57  4-[2-Amino-5-(2-fluorophenyl)thieno[2,3-d]pyrimidin-4-yl]-N-(4-methoxyphenyl)-piperazine-1-carboxamide,
58  4-(2-Amino-6-methyl-5-phenylthieno[2,3-d]pyrimidin-4-yl)-N-[4-(dimethylamino)-phenyl]piperazine-1-carboxamide,
59  4-(2-Amino-6-methyl-5-phenylthieno[2,3-d]pyrimidin-4-yl)-N-(2-methoxyphenyl)-piperazine-1-carboxamide,
60  4-(2-Amino-6-methyl-5-phenylthieno[2,3-d]pyrimidin-4-yl)-N-[3-(morpholin-4-yl-methyl)phenyl]piperazine-1-carboxamide,
61  4-(2-Amino-6-methyl-5-phenylthieno[2,3-d]pyrimidin-4-yl)-N-(3-methylphenyl)-piperazine-1-carboxamide,
62  4-[2-Amino-5-(4-fluorophenyl)-6-methylthieno[2,3-d]pyrimidin-4-yl]-N-[4-(4-methyl-piperazin-1-yl)-phenyl]piperazine-1-carboxamide, 63 4-[2-Amino-5-(4-fluorophenyl)-6-methylthieno[2,3-d]pyrimidin-4-yl]-N-[4-(dimethyl-amino)phenyl]piperazine-1-carboxamide, 64 4-[2-Amino-5-(4-fluorophenyl)-6-methylthieno[2,3-d]pyrimidin-4-yl]-N-(4-methoxy-phenyl)piperazine-1-carboxamide, 65 4-(2-Amino-5-methylthieno[2,3-d]pyrimidin-4-yl)-N-(4-methoxy-2-methylphenyl)-piperazine-1-carboxamide, 66 4-(2-Amino-5-methylthieno[2,3-d]pyrimidin-4-yl)-N-(4-methoxyphenyl)piperazine-1-carboxamide, 67 4-(2-Amino-5-cyclohexylthieno[2,3-d]pyrimidin-4-yl)-N-(4-methoxy-2-methylphenyl)-piperazine-1-carboxamide, 68 4-(2-Amino-5-cyclohexylthieno[2,3-d]pyrimidin-4-yl)-N-[4-(dimethylamino)phenyl]-piperazine-1-carboxamide, 69 4-(2-Amino-5-cyclohexylthieno[2,3-d]pyrimidin-4-yl)-N-(4-methoxyphenyl)piperazine-1-carboxamide, 70 4-[2-Amino-5-(3-chloropropyl)thieno[2,3-d]pyrimidin-4-yl]-N-(4-methoxy-2-methyl-phenyl)piperazine-1-carboxamide, 71 4-[2-Amino-5-(3-chloropropyl)thieno[2, 3-d]pyrimidin-4-yl]-N-(4-methoxyphenyl)-piperazine-1-carboxamide, 72 4-(2-Aminothieno[2,3-d]pyrimidin-4-yl)-N-[4-(dimethylamino)phenyl]piperazine-1-carboxamide, 73 4-[2-Amino-5-(ethoxycarbonyl)thieno[2,3-d]pyrimidin-4-yl]-N-[4-(dimethylamino)-phenyl]piperazine-1-carboxamide, 74 4-[2-Amino-5-(ethoxycarbonyl)thieno[2,3-d]pyrimidin-4-yl]-N-(2,4-difluorophenyl)-piperazine-1-carboxamide, 75 Ethyl 2-amino-4-{4-[4-(4-methylpiperazin-1-yl)phenylcarbamoyl]piperazin-1-yl}thieno[2,3-d]pyrimidine-5-carboxylate, 76 4-[2-Amino-5-(ethoxycarbonyl)thieno[2,3-d]pyrimidin-4-yl]-N-(2,4-dimethoxyphenyl)-piperazine-1-carboxamide, 77 4-[2-Amino-5-(ethoxycarbonyl)thieno[2,3-d]pyrimidin-4-yl]-N-(4-methoxy-2-methyl-phenyl)piperazine-1-carboxamide, 78 4-[2-Amino-5-(hydroxymethyl)thieno[2,3-d]pyrimidin-4-yl]-N-[4-(dimethylamino)-phenyl]piperazine-1-carboxamide, 79 Ethyl 2-amino-4-{4-[4-(dimethylamino)phenylcarbamoyl]piperazin-1-yl}thieno[2,3-d]-pyrimidin-5-yl-carbamate, 80 2-Amino-4-[4-(4-methoxy-2-methylphenylcarbamoyl)piperazin-1-yl]thieno[2,3-d]-pyrimidine-5-carboxylic acid (2-hydroxy-1,1-dimethylethyl)amide, 81 4-[2-Amino-5-(trifluoromethyl)thieno[2,3-d]pyrimidin-4-yl]piperazine-1-carboxylic acid (4-methoxyphenyl)amide, 82 4-[2-Amino-5-(trifluoromethyl)thieno[2,3-d]pyrimidin-4-yl]piperazine-1-carboxylic acid (4-methoxy-2-methylphenyl)amide, 83 2-Amino-4-[4-(4-methoxyphenylcarbamoyl)piperazin-1-yl]isothiazolo[5,4-d]pyrimidine, 84 2-Amino-4-[4-(4-methoxy-2-methylphenylcarbamoyl)piperazin-1-yl]isothiazolo[5,4-d]-pyrimidine, 85 2-Amino-4-[4-(4-methoxyphenylcarbamoyl)-2-(S)-methylpiperazin-1-yl]isothiazolo[5,4-d]pyrimidine, 86 2-Amino-4-[4-(4-methoxy-2-methylphenylcarbamoyl)-2-(S)-methylpiperazin-1-yl]-isothiazolo[5,4-d]pyrimidine, 87 4-(2-Amino-5-cyanothieno[2,3-d]pyrimidin-4-yl)piperazine-1-carboxylic acid (4-methoxyphenyl)amide, 88 4-(2-Amino-5-oxo-5,6-dihydrothieno[2,3-d]pyrimidin-4-yl)piperazine-1-carboxylic acid (4-methoxy-2-methylphenyl)amide, 89 Ethyl 2-amino-4-{4-[(3-chloro-4-methoxyphenyl)-carbamoyl]piperazin-1-yl}thieno[2,3-d]pyrimidine-5-carboxylate, 90 Ethyl 2-amino-4-{4-[(4-ethoxyphenyl)carbamoyl]-piperazin-1-yl}thieno[2,3-d]pyrimidine-5-carboxylate, 91 Ethyl 2-amino-4-[4-(o-tolylcarbamoyl)piperazin-1-yl]thieno[2,3-d]pyrimidine-5-carboxylate, 92 Ethyl 2-amino-4-[4-(m-tolylcarbamoyl)piperazin-1-yl]thieno[2,3-d]pyrimidine-5-carboxylate, 93 Ethyl 2-amino-4-[4-(benzo[d][1,3]dioxol-5-yl-carbamoyl)piperazin-1-yl]thieno[2,3-d]pyrimidine-5-carboxylate, 94 Ethyl 2-amino-4-(4-{[4-(trifluoromethoxy)phenyl]-carbamoyl}piperazin-1-yl)thieno[2,3-d]pyrimidine-5-carboxylate, 95 Ethyl 2-amino-4-(4-{[4-(difluoromethoxy)phenyl]-carbamoyl}piperazin-1-yl)thieno[2,3-d]pyrimidine-5-carboxylate, 96 Ethyl 2-amino-4-[4-(phenylcarbamoyl)piperazin-1-yl]thieno[2,3-d]pyrimidine-5-carboxylate, 97 Ethyl 2-amino-4-(4-{2-[4-(dimethylamino)phenyl]-acetyl}piperazin-1-yl)thieno[2,3-d]pyrimidine-5-carboxylate, 98 Ethyl 2-amino-4-[4-(benzylcarbamoyl)piperazin-1-yl]thieno[2,3-d]pyrimidine-5-carboxylate, 99 Ethyl 2-amino-4-{4-[2-(pyridin-4-yl)acetyl]-piperazin-1-yl}thieno[2,3-d]pyrimidine-5-carboxylate, 100 Ethyl 2-amino-4-[4-(pyridin-3-ylmethyl)piperazin-1-yl]thieno[2,3-d]pyrimidine-5-carboxylate, 101 Ethyl 2-amino-4-{4-[(4-methoxybenzyl)-carbamoyl]piperazin-1-yl}thieno[2,3-d]pyrimidine-5-carboxylate, 102 Ethyl 2-amino-4-[4-(5-methyl-1H-pyrazole-3-carbonyl)piperazin-1-yl]thieno[2,3-d]pyrimidine-5-carboxylate, 103 Ethyl 2-amino-4-[4-(2-phenoxyacetyl)piperazin-1-yl]thieno[2,3-d]pyrimidine-5-carboxylate, 104 Ethyl 2-amino-4-[4-(imidazo[1,2-a]pyridine-2-carbonyl)piperazin-1-yl]thieno[2,3-d]pyrimidine-5-carboxylate, 105 Ethyl 2-amino-4-[4-(pyridin-2-ylmethyl)piperazin-1-yl]thieno[2,3-d]pyrimidine-5-carboxylate, 106 Ethyl 2-amino-4-(4-nicotinoylpiperazin-1-yl)-thieno[2,3-d]pyrimidine-5-carboxylate, 107 Ethyl 2-amino-4-{4-[2-(3,4-dimethoxyphenyl)-acetyl]piperazin-1-yl}thieno[2,3-d]pyrimidine-5-carboxylate, 108 (S)-Ethyl 2-amino-4-[4-(1,2,3,4-tetrahydro-isoquinoline-3-carbonyl)piperazin-1-yl]thieno[2,3-d]pyrimidine-5-carboxylate, 109 Ethyl 2-amino-4-[4-(1-methyl-1H-imidazole-5-carbonyl)piperazin-1-yl]thieno[2,3-d]pyrimidine-5-carboxylate, 110 Ethyl 4-[4-(1H-indazole-3-carbonyl)piperazin-1-yl]-2-aminothieno[2,3-d]pyrimidine-5-carboxylate, 111 Ethyl 2-amino-4-{4-[6-(hydroxymethyl)picolinoyl]-piperazin-1-yl}thieno[2,3-d]pyrimidine-5-carboxylate, 112 Ethyl 2-amino-4-[4-(quinoxaline-2-carbonyl)-piperazin-1-yl]thieno[2,3-d]pyrimidine-5-carboxylate, 113 Ethyl 2-amino-4-[4-(isoquinoline-3-carbonyl)-piperazin-1-yl]thieno[2,3-d]pyrimidine-5-carboxylate, 114

Ethyl 2-amino-4-{4-[3-(2-methyl-1H-imidazol-1-yl)propanoyl]piperazin-1-yl}thieno[2,3-d]-pyrimidine-5-carboxylate,
115 Ethyl 2-amino-4-{4-[1-(tert-butoxycarbonyl)-piperidine-4-carbonyl]piperazin-1-yl}thieno[2,3-d]-pyrimidine-5-carboxylate,
116 Ethyl 2-amino-4-{4-[(1-phenylethyl)carbamoyl]-piperazin-1-yl}thieno[2,3-d]pyrimidine-5-carboxylate,
117 rac-(R)- Ethyl 2-amino-4-[4-(3-hydroxy-3-phenylpropanoyl)piperazin-1-yl]thieno[2,3-d]pyrimidine-5-carboxylate,
118 Ethyl 4-[4-(1H-pyrazole-3-carbonyl)piperazin-1-yl]-2-aminothieno[2,3-d]pyrimidine-5-carboxylate,
119 Ethyl 2-amino-4-{4-[2-(morpholin-4-yl)acetyl]-piperazin-1-yl}thieno[2,3-d]pyrimidine-5-carboxylate,
120 Ethyl 2-amino-4-[4-(1-methyl-1H-imidazole-2-carbonyl)piperazin-1-yl]thieno[2,3-d]pyrimidine-5-carboxylate,
121 Ethyl 2-amino-4-{4-[2-(thien-3-yl)acetyl]piperazin-1-yl}thieno[2,3-d]pyrimidine-5-carboxylate,
122 Ethyl 2-amino-4-{4-(pyrazine-2-carbonyl)piperazin-1-yl]thieno[2,3-d]pyrimidine-5-carboxylate,
123 Ethyl 2-amino-4-(4-picolinoylpiperazin-1-yl)-thieno[2,3-d]pyrimidine-5-carboxylate,
124 Ethyl 2-amino-4-{4-[3-(pyridin-3-yl)propanoyl]-piperazin-1-yl}thieno[2,3-d]pyrimidine-5-carboxylate,
125 Ethyl 2-amino-4-(4-benzylpiperazin-1-yl)-thieno[2,3-d]pyrimidine-5-carboxylate,
126 Ethyl 2-amino-4-[4-(imidazo[1,2-a]pyridine-3-carbonyl)piperazin-1-yl]thieno[2,3-d]pyrimidine-5-carboxylate,
127 Ethyl 2-amino-4-{4-[3-(morpholin-4-yl)propanoyl]-piperazin-1-yl}thieno[2,3-d]pyrimidine-5-carboxylate,
128 Ethyl 2-amino-4-{4-[3-(4-methoxyphenyl)-propanoyl]piperazin-1-yl}thieno[2,3-d]pyrimidine-5-carboxylate,
129 Ethyl 2-amino-4-{4-[3-(3-methoxyphenyl)-propanoyl]piperazin-1-yl}thieno[2,3-d]pyrimidine-5-carboxylate,
130 Ethyl 4-4-{4-[3-(1H-benzo [d]imidazol-2 -yl)-propanoyl]piperazin-1-yl}-2-aminothieno[2,3-d]-pyrimidine-5-carboxylate,
131 Ethyl 2-amino-4-[4-(2-phenylethyl)piperazin-1-yl]-thieno[2,3-d]pyrimidine-5-carboxylate,
132 Ethyl 2-amino-4-{4-[3-(2-methoxyphenyl)-propanoyl]piperazin-1-yl}thieno[2,3-d]pyrimidine-5-carboxylate,
133 Ethyl 2-amino-4-[4-(1,2,3,4-tetrahydronaphthalene-2-carbonyl)piperazin-1-yl]thieno[2,3-d]pyrimidine-5-carboxylate,
134 Ethyl 2-amino-4-{4-[3-(furan-2-yl)propanoyl]-piperazin-1-yl}thieno[2,3-d]pyrimidine-5-carboxylate,
135 Ethyl 2-amino-4-(4-benzoylpiperazin-1-yl)-thieno[2,3-d]pyrimidine-5-carboxylate,
136 Ethyl 2-amino-4-[4-(3-cyclopentylpropanoyl)-piperazin-1-yl]thieno[2,3-d]pyrimidine-5-carboxylate,
137 Ethyl 2-amino-4-[4-(isoquinoline-1-carbonyl)-piperazin-1-yl]thieno[2,3-d]pyrimidine-5-carboxylate,
138 Ethyl 2-amino-4-{4-[3-(3-chloro-4-methoxy-phenyl)propanoyl]piperazin-1-yl}thieno[2,3-d]-pyrimidine-5-carboxylate,
139 Ethyl 2-amino-4-[4-(quinoline-2-carbonyl)-piperazin-1-yl]thieno[2,3-d]pyrimidine-5-carboxylate,
140 Ethyl 2-amino-4-[4-[3-(4-fluorophenyl)propanoyl]-piperazin-1-yl]thieno[2,3-d]pyrimidine-5-carboxylate,
141 Ethyl 2-amino-4-{4-[3-(p-tolyl)propanoyl]-piperazin-1-yl}thieno[2,3-d]pyrimidine-5-carboxylate,
142 Ethyl 4-[4-(1H-benzo [d]imidazole-2-carbonyl)-piperazin-1-yl]-2-aminothieno[2,3-d]pyrimidine-5-carboxylate,
143 Ethyl 2-amino-4-{4-[3-(4-methylpiperazin-1-yl)-propanoyl]piperazin-1-yl}thieno[2,3-d]pyrimidine-5-carboxylate,
144 Ethyl 2-amino-4-{4-[2-(dimethylamino)acetyl]-piperazin-1-yl}thieno[2,3-d]pyrimidine-5-carboxylate,
145 Ethyl 2-amino-4-{4-[3-(o-tolyl)propanoyl]-piperazin-1-yl}thieno[2,3-d]pyrimidine-5-carboxylate,
146 Ethyl 4-[4-(1H-indole-2-carbonyl)piperazin-1-yl]-2-aminothieno[2,3-d]pyrimidine-5-carboxylate,
147 (S)-Ethyl 2-amino-4-{4-[2-(methylamino)-2-phenylacetyl]piperazin-1-yl}thieno[2,3-d]-pyrimidine-5-carboxylate,
148 Ethyl 2-amino-4-{4-[1-(4-methoxyphenyl)-cyclopropanecarbonyl]piperazin-1-yl}thieno[2,3-d]pyrimidine-5-carboxylate,
149 Ethyl 2-amino-4-[4-(2-methyl-3-phenylpropanoyl)-piperazin-1-yl]thieno[2,3-d]pyrimidine-5-carboxylate,
150 Ethyl 2-amino-4-[4-(2-phenylcyclopropane-carbonyl)piperazin-1-yl]thieno[2,3-d]pyrimidine-5-carboxylate,
151 Ethyl 2-amino-4-[4-(3-phenylbutyl)piperazin-1-yl]-thieno[2,3-d]pyrimidine-5-carboxylate,
152 (S)-Ethyl 2-amino-4-[4-(1-methylpyrrolidine-2-carbonyl)piperazin-1-yl]thieno[2,3-d]pyrimidine-5-carboxylate,
153 Ethyl 4-{4-[3-(1H-indol-3-yl)propanoyl]piperazin-1-yl}2-aminothieno[2,3-d]pyrimidine-5-carboxylate,
154 Ethyl 2-amino-4-[4-(3-phenylpropanoyl)piperazin-1-yl]thieno[2,3-d]pyrimidine-5-carboxylate,
155 Ethyl 2-amino-4-[4-(3-phenylpropyl)piperazin-1-yl]thieno[2,3-d]pyrimidine-5-carboxylate,
156 Ethyl 2-amino-4-{4-[(4-methoxyphenyl)-carbamoyl]-3-methylpiperazin-1-yl}thieno[2,3-d]-pyrimidine-5-carboxylate,
157 Ethyl 2-amino-4-{4-[(4-methoxyphenyl)-carbamoyl]-2-methylpiperazin-1-yl}thieno[2,3-d]-pyrimidine-5-carboxylate,
158 Ethyl 2-amino-4-{4-[2-(3-methoxyphenoxy)acetyl]-3-methylpiperazin-1-yl}thieno[2,3-d]$_p$yrimidine-5-carboxylate,
159 Ethyl 2-amino-4-{4-[2-(4-methoxyphenoxy)acetyl]-3-methylpiperazin-1-yl}thieno[2,3-d]pyrimidine-5-carboxylate,
160 Ethyl 2-amino-4-[2-methyl-4-(p-tolylcarbamoyl)-piperazin-1-yl]thieno[2,3-d]pyrimidine-5-carboxylate,
161 Ethyl 2-amino-4-4-{4-[(3-methoxyphenyl)-carbamoyl]-2-methylpiperazin-1-yl}thieno[2,3-d]-pyrimidine-5-carboxylate,
162 Ethyl 2-amino-4-4-{4-[(3-methoxyphenyl)-carbamoyl]-3-methylpiperazin-1-yl}thieno[2,3-d]-pyrimidine-5-carboxylate,
163 Ethyl 2-amino-4-[3-methyl-4-(p-tolylcarbamoyl)-piperazin-1-yl]thieno[2,3-d]pyrimidine-5-carboxylate,
164 Ethyl 2-amino-4-4-{4-[2-(3-methoxyphenoxy)acetyl]-2-methylpiperazin-1-yl}thieno[2,3-d]pyrimidine-5-carboxylate, 165 Ethyl 2-amino-4-{4-[2-(4-methoxyphenoxy)acetyl]-2-methylpiperazin-1-yl}thieno[2,3-d]pyrimidine-5-carboxylate,
166 Ethyl 2-amino-4-4-{4-[3-(4-methoxyphenyl)-propanoyl]-3-methylpiperazin-1-yl}thieno[2,3-d]-pyrimidine-5-carboxylate,
167 Ethyl 2-amino-4-4-{4-[3-(4-methoxyphenyl)-propanoyl]-2-methylpiperazin-1-yl}thieno[2,3-d]-pyrimidine-5-carboxylate, 168 Ethyl 2-amino-4-4-{5-[2-(3-methoxyphenoxy) acetyl]-2,5-diazabicyclo[2.2.1]heptan-2-yl}thieno[2,3-d]-pyrimidine-5-carboxylate, 169 Ethyl 2-amino-4-4-{5-[(3-methoxyphenyl)-carbamoyl]-2,5-diazabicyclo[2.2.1]heptan-2-yl}-thieno[2,3-d] pyrimidine-5-carboxylate, 170 Ethyl 2-amino-4-[5-(p-tolylcarbamoyl)-2,5-diazabicyclo[2.2.1]heptan-2-yl]thieno[2,3-d]-pyrimidine-5-carboxylate, 171 Ethyl 2-amino-4-{5-[(4-methoxyphenyl)-carbamoyl]-2,5-diazabicyclo[2.2.1]heptan-2-yl}-thieno[2,3-d] pyrimidine-5-carboxylate, 172 Ethyl 2-amino-4-{5-[3-(4-methoxyphenyl)-propanoyl]-2,5-diazabicyclo [2.2.1]heptan-2-yl}-thieno[2,3-d]pyrimidine-5-carboxylate, 173 Ethyl 2-amino-4-{5-[2-(4-methoxyphenoxy)acetyl]-2,5-diazabicyclo[2.2.1]heptan-2-yl}thieno[2,3-d]-pyrimidine-5-carboxylate, 174 Ethyl 2-amino-4-{4-[(4-methoxy-2-methylphenyl)-carbamoyl]-2-methylpiperazin-1-yl}thieno[2,3-d]-pyrimidine-5-carboxylate, 175 Ethyl 2-amino-4-{(2S)-4-[(4-methoxy-2-methyl-phenyl)carbamoyl]-2-methylpiperazin-1-yl]-thieno[2,3-d]pyrimidine-5-carboxylate, 176 4-(2-Aminothieno[2,3-d]pyrimidin-4-yl)-N-(3-chloro-4-methoxyphenyl)piperazine-1-carboxamide, 177 4-(2-Aminothieno[2,3-d]pyrimidin-4-yl)-N-(o-tolyl)piperazine-1-carboxamide, 178 4-(2-Aminothieno[2,3-d]pyrimidin-4-yl)-N-(4-methoxyphenyl)piperazine-1-carboxamide, 179 4-(2-Aminothieno[2,3-d]pyrimidin-4-yl)-N-(4-ethoxyphenyl)piperazine-1-carboxamide, 180 4-(2-Aminothieno[2,3-d]pyrimidin-4-yl)-N-(benzo[d][1,3]dioxo1-5-yl)piperazine-1-carboxamide, 181 4-(2-Aminothieno[2,3-d]pyrimidin-4-yl)-N-[4-(trifluoromethoxy)phenyl]piperazine-1-carboxamide, 182 4-(2-Aminothieno[2,3-d]pyrimidin-4-yl)-N-(m-tolyl)piperazine-1-carboxamide, 183 4-(2-Aminothieno[2,3-d]pyrimidin-4-yl)-N-[4-(difluoromethoxy)phenyl]piperazine-1-carboxamide, 184 1-[4-(2-Aminothieno[2,3-d]pyrimidin-4-yl)-piperazin-1-yl]-2-phenoxyethanone, 185 [4-(2-Aminothieno[2,3-d]pyrimidin-4-yl)piperazin-1-yl](1H-pyrazol-3-yl)methanone, 186 4-(2-Aminothieno[2,3-d]pyrimidin-4-yl)-N-phenyl-piperazine-1-carboxamide, 187 [4-(2-Aminothieno[2,3-d]pyrimidin-4-yl)piperazin-1-yl](5-methyl-1H-pyrazol-3-yl)methanone, 188 [4-(2-Aminothieno[2,3-d]pyrimidin-4-yl)piperazin-1-yl](imidazo[1,2-a]pyridin-2-yl)methanone, 189 [4-(2-Aminothieno[2,3-d]pyrimidin-4-yl)piperazin-1-yl](isoquinolin-3-yl)methanone, 190 4-(2-Aminothieno[2,3-d]pyrimidin-4-yl)-N-benzyl-piperazine-1-carboxamide, 191 1-[4-(2-Aminothieno[2,3-d]pyrimidin-4-yl)-piperazin-1-yl]-3-(4-methoxyphenyl)propan-1-one, 192 4-(2-Aminothieno[2,3-d]pyrimidin-4-yl)-N-(4-methoxybenzyl)piperazine-1-carboxamide, 193 [4-(2-Aminothieno[2,3-d]pyrimidin-4-yl)piperazin-1-yl](pyrazin-2-yl)methanone, 194 1-[4-(2-Aminothieno[2,3-d]pyrimidin-4-yl)-piperazin-1-yl]-2-[4-(dimethylamino)phenyl]-ethanone, 195 1-[4-(2-Aminothieno[2,3-d]pyrimidin-4-yl)-piperazin-1-yl]-3-(1H-benzo[d]imidazol-2-yl)-propan-1-one, 196 [4-(2-Aminothieno[2,3-d]pyrimidin-4-yl)piperazin-1-yl](1-methyl-1H-imidazol-2-yl)methanone, 197 1-[4-(2-Aminothieno[2,3-d]pyrimidin-4-yl)-piperazin-1-yl]-2-(pyridin-4-yl)ethanone, 198 (S)-1-[4-(2-Aminothieno[2,3-d]pyrimidin-4-yl)-piperazin-1-yl]-3-hydroxy-3-phenylpropan-1-one, 199 1-[4-(2-Aminothieno[2,3-d]pyrimidin-4-yl)-piperazin-1-yl]-2-(thien-3-yl)ethanone, 200 4-[4-(Pyridin-3-ylmethyl)piperazin-1-yl]thieno[2,3-d]pyrimidin-2-amine, 201 [4-(2-Aminothieno[2,3-d]pyrimidin-4-yl)piperazin-1-yl](1-methyl-1H-imidazol-5-yl)methanone, 202 1-[4-(2-Aminothieno[2,3-d]pyrimidin-4-yl)-piperazin-1-yl]-2-(3,4-dimethoxyphenyl)ethanone, 203 [4-(2-Aminothieno[2,3-d]pyrimidin-4-yl)piperazin-1-yl](quinoxalin-2-yl)methanone, 204 [4-(2-Aminothieno[2,3-d]pyrimidin-4-yl)piperazin-1-yl](1H-indazol-3-yl)methanone, 205 4-(2-Aminothieno[2,3-d]pyrimidin-4-yl)-N-(1-phenylethyl)piperazine-1-carboxamide, 206 1-[4-(2-Aminothieno[2,3-d]pyrimidin-4-yl)-piperazin-1-yl]-3-phenylpropan-1-one 207 [4-(2-Aminothieno[2,3-d]pyrimidin-4-yl)piperazin-1-yl](pyridin-3-yl)methanone, 208 1-[4-(2-Aminothieno[2,3-d]pyrimidin-4-yl)-piperazin-1-yl]-3-(furan-2-yl)propan-1-one, 209 [4-(2-Aminothieno[2,3-d]pyrimidin-4-yl)piperazin-1-yl][6-(hydroxymethyl)pyridin-2-yl]methanone, 210 [4-(2-Aminothieno[2,3-d]pyrimidin-4-yl)piperazin-1-yl](phenyl)methanone, 211 1-[4-(2-Aminothieno[2,3-d]pyrimidin-4-yl)-piperazin-1-yl]-3-cyclopentylpropan-1-one, 212 1-[4-(2-Aminothieno[2,3-d]pyrimidin-4-yl)-piperazin-1-yl]-3-(4-methylpiperazin-1-yl)propan-1-one, 213 [4-(2-Aminothieno[2,3-d]pyrimidin-4-yl)piperazin-1-yl](quinolin-2-yl)methanone, 214 4-[4-(Pyridin-2-ylmethyl)piperazin-1-yl]thieno[2,3-d]pyrimidin-2-amine, 215 1-[4-(2-Aminothieno[2,3-d]pyrimidin-4-yl)-piperazin-1-yl]-3-(3-methoxyphenyl)propan-1-one, 216 1-[4-(2-Aminothieno[2,3-d]pyrimidin-4-yl)-piperazin-1-yl]-3-(o-tolyl)propan-1-one 217 1-[4-(2-Aminothieno[2,3-d]pyrimidin-4-yl)-piperazin-1-yl]-2-(morpholin-4-yl)ethanone, 218 4-[4-(3-Phenylbutyl)piperazin-1-yl]thieno[2,3-d]-pyrimidin-2-amine, 219 4-(4-Benzylpiperazin-1-yl)thieno[2,3-d]pyrimidin-2-amine, 220 4-[4-(2-Phenylethyl)piperazin-1-yl]thieno[2,3-d]-pyrimidin-2-amine, 221 4-[4-(3-Phenylpropyl)piperazin-1-yl]thieno[2,3-d]-pyrimidin-2-amine, 222 tert-Butyl 4-[4-(2-aminothieno[2,3-d]pyrimidin-4-yl)piperazine-1-carbonyl]piperidine-1-carboxylate, 223 1-[4-(2-Aminothieno[2,3-d]pyrimidin-4-yl)-piperazin-1-yl]-2-(dimethylamino)ethanone, 224 1-[4-(2-Aminothieno[2,3-d]pyrimidin-4-yl)-piperazin-1-yl]-2-methyl-3-phenylpropan-1-one, 225 1-[4-(2-Aminothieno[2,3-d]pyrimidin-4-yl)-piperazin-1-yl]-3-(4-fluorophenyl)propan-1-one, 226 1-[4-(2-Aminothieno[2,3-d]pyrimidin-4-yl)-piperazin-1-yl]-3-(p-tolyl)propan-1-one 227 1-[4-(2-Aminothieno[2,3-d]pyrimidin-4-yl)-piperazin-1-yl]-3-(1H-indol-3-yl)propan-1-one, 228 (S)-[4-(2-Aminothieno[2,3-d]pyrimidin-4-yl)-piperazin-1-yl](1-methylpyrrolidin-2-yl)methanone, 229 [4-(2-Aminothieno[2,3-d]pyrimidin-4-yl)piperazin-1-yl](1H-benzo[d]imidazol-2-yl)methanone, 230 (S)-1-[4-(2-Aminothieno[2,3-d]pyrimidin-4-yl)-piperazin-1-yl]-2-(methylamino)-2-phenylethanone, 231 [4-(2-Aminothieno[2,3-d]pyrimidin-4-yl)piperazin-1-yl][1-(4-methoxyphenyl)cyclopropl]methanone, 232 1-[4-(2-Aminothieno[2,3-d]pyrimidin-4-yl)-piperazin-1-yl]-3-(2-methyl-1H-imidazol-1-yl)-propan-1-one, 233 (S)-tert-Butyl N-{2-[4-(2-aminothieno[2,3-d]-pyrimidin-4-yl)piperazin-1-yl]-2-oxo-1-phenyl-ethal}-N-(methyl)carbamate, 234 (S)-tert-Butyl 3-[4-(2-aminothieno[2,3-d]pyrimidin-4-yl)piperazine-1-carbonyl]-3,4-dihydro-isoquinoline-2(1H)-carboxylate, 235 [4-(2-Aminothieno[2,3-d]pyrimidin-4-yl)piperazin-1-yl](pyridin-2-yl)methanone, 236 1-[4-(2-Aminothieno[2,3-d]pyrimidin-4-yl)-piperazin-1-yl]-3-(morpholin-4-yl)propan-1-one, 237 1-[4-(2-Aminothieno[2,3-d]pyrimidin-4-yl)-piperazin-1-yl]-2-(4-methylpiperazin-1-yl)ethanone, 238 [4-(2-Aminothieno[2,3-d]pyrimidin-4-yl)piperazin-1-yl](2-phenylcyclopropyl)methanone, 239 1-[4-(2-Aminothieno[2,3-d]pyrimidin-4-yl)-piperazin-1-yl]-3-(3-chloro-4-methoxyphenyl)-propan-1-one, 240 1-[4-(2-Aminothieno[2,3-d]pyrimidin-4-yl)-piperazin-1-yl]-3-(pyridin-3-yl)propan-1-one, 241 1-[4-(2-Aminothieno[2,3-d]pyrimidin-4-yl)-piperazin-1-yl]-3-(2-methoxyphenyl)propan-1-one, 242 [4-(2-Aminothieno[2,3-d]pyrimidin-4-yl)piperazin-1-yl](1H-indol-2-yl)methanone, 243 [4-(2-Aminothieno[2,3-d]pyrimidin-4-yl)piperazin-1-yl](isoquinolin-1-yl)methanone, 244 [4-(2-Aminothieno[2,3-d]pyrimidin-4-yl)piperazin-1-yl](1,2,3,4-tetrahydronaphthalen-2-yl)methanone, 245 [4-(2-Aminothieno[2,3-d]pyrimidin-4-yl)piperazin-1-yl](imidazo[1,2-α]pyridin-3-yl)methanone, 246 4-(2-Aminothieno[2,3-d]pyrimidin-4-yl)-N-(4-methoxyphenyl)-3-methylpiperazine-1-carboxamide, 247 4-(2-Aminothieno[2,3-d]pyrimidin-4-yl)-N-(4-methoxy-2-methylphenyl)-3-methylpiperazine-1-carboxamide, 248 4-(2-Aminothieno[2,3-d]pyrimidin-4-yl)-N-(3-methoxyphenyl)-3-methylpiperazine-1-carboxamide, 249 1-[4-(2-Aminothieno[2,3-d]pyrimidin-4-yl)-3-methylpiperazin-1-yl]-2-(3-methoxyphenoxy)-ethanone, 250 1-[4-(2-Aminothieno[2,3-d]pyrimidin-4-yl)-3-methylpiperazin-1-yl]-2-(4-methoxyphenoxy)-ethanone, 251 4-(2-Aminothieno[2,3-d]pyrimidin-4-yl)-3-(hydroxymethyl)-N-(p-tolyl)piperazine-1-carboxamide, 252 4-(2-Aminothieno[2,3-d]pyrimidin-4-yl)-3-(hydroxymethyl)-N-(4-methoxyphenyl)piperazine-1-carboxamide, 253 1-[4-(2-Aminothieno[2,3-d]pyrimidin-4-yl)-3-(hydroxymethyl)piperazin-1-yl]-2-(3-methoxy-phenoxy)ethanone, 254 (3S)-4-(2-Aminothieno[2,3-d]pyrimidin-4-yl)-N-(4-methoxyphenyl)-3methylpiperazine-1-carboxamide, 255 (3S)-4-(2-Aminothieno[2,3-d]pyrimidin-4-yl)-N-(4-methoxy-2-methylphenyl)-3-methylpiperazine-1-carboxamide, 256 (3R)-4-(2-Aminothieno[2,3-d]pyrimidin-4-yl)-N-(4-methoxyphenyl)-3-methylpiperazine-1-carboxamide, 257 (3R)-4-(2-Aminothieno[2,3-d]pyrimidin-4-yl)-N-(4-methoxy-2-methylphenyl)-3-methylpiperazine-1-carboxamide, 258 4-(2-Amino-5-cyanothieno[2,3-d]pyrimidin-4-yl)-N-(4-methoxyphenyl)-3-methyl-piperazine-1-carboxamide, 259 4-(2-Amino-5-cyanothieno[2,3-d]pyrimidin-4-yl)-N-(4-methoxy-2-methylphenyl)-3-methylpiperazine-1-carboxamide, 260 4-[2-Amino-5-(3-methyl-1,2,4-oxadiazol-5-yl)thieno[2,3-d]pyrimidin-4-yl]-N-(4-methoxyphenyl)piperazine-1-carboxamide, 261 4-[2-Amino-5-(3-isopropyl-1,2,4-oxadiazol-5-yl)thieno[2,3-d]pyrimidin-4-yl]-N-(4-methoxyphenyl)piperazine-1-carboxamide, or 262 4-[2-Amino-5-(3-tert-butyl-1,2,4-oxadiazol-5-yl)thieno[2,3-d]pyrimidin-4-yl]-N-(4-methoxyphenyl)piperazine-1-carboxamide, or a pharmaceutically acceptable salt thereof.

10. A pharmaceutical composition comprising a compound of formula (I) as defined in claim 1, or a pharmaceutically acceptable salt or solvate thereof, in association with a pharmaceutically acceptable carrier.

11. A method for the treatment of a viral disease, or organ or cell transplant rejection, which comprises administering to a patient in need of such treatment an effective amount of a compound of formula (I) as defined in claim 1, or a pharmaceutically acceptable salt or solvate thereof.

* * * * *